United States Patent [19]
Misawa et al.

[11] Patent Number: 5,972,690
[45] Date of Patent: Oct. 26, 1999

[54] DNA STRANDS USEFUL FOR THE SYNTHESIS OF XANTHOPHYLLS AND THE PROCESS FOR PRODUCING THE XANTHOPHYLLS

[75] Inventors: Norihiko Misawa; Keiji Kondo; Susumu Kajiwara, all of Yokohama; Akihiro Yokoyama, Shimizu, all of Japan

[73] Assignees: Kirin Beer Kabushiki Kaisha; Marine Biotechnology Institute Co., Ltd, both of Tokyo-to, Japan

[21] Appl. No.: 09/006,491

[22] Filed: Jan. 13, 1998

Related U.S. Application Data

[62] Division of application No. 08/663,310, filed as application No. PCT/JP94/02220, Dec. 26, 1994, Pat. No. 5,811,273.

[30] Foreign Application Priority Data

Dec. 27, 1993 [JP] Japan ................................ 5-348737
Sep. 5, 1994 [JP] Japan ................................ 6-235917

[51] Int. Cl.⁶ ........................... C12N 1/20; C07H 21/04
[52] U.S. Cl. .............................. 435/252.33; 435/252.3; 435/254.11; 435/320.1; 435/189; 536/23.2; 536/23.1
[58] Field of Search ................. 435/189, 252.3, 435/252.33, 320.1, 148; 536/23.1, 23.2, 23.7

[56] References Cited

FOREIGN PATENT DOCUMENTS

| | | |
|---|---|---|
| 0 393 690 | 10/1990 | European Pat. Off. . |
| 0 725 137 | 8/1996 | European Pat. Off. . |
| 94/06918 | 3/1994 | WIPO . |

OTHER PUBLICATIONS

A. Yokoyama et al., "Marine Bacteria Produced Astaxanthin", 10th International Symposium on Carotenoids, abstract, CL11–3 (1993).

Yokoyama, et al., "Production of Astaxanthin and 4–Ketozeaxanthin by the Marine Bacterium, *Agro–bacterium aurantiacum*," *Biosci. Biotech. Biochem.* 58(10): 1842–44 (1994).

Misawa, et al., "Elucidation of the *Erwinia unredovora* Carotenoid Biosynthetic Pathway by Functional Analysis of Gene Products Expressed in *Escherichia coli*," *J. Bacteriology* 172(12): 6704–12 (Dec. 1990).

Misawa, et al., "Production of β–Carotene in *Zymomonas mobilis* and *Agrobacterium tumefaciens* by Introduction of the Biosynthesis Genes from *Erwinia uredovora*," *Applied and Environmental Microbiology* 57(6): 1847–49 (Jun. 1991).

Misawa et al., "Structure and Functional Analysis of a Marine Bacterial Carotenoid Biosynthesis Gene Cluster And Astaxanthin Biosynthetic Pathway Proposed at The Gene Level" *J. Bacteriol.*, 177(22):6575–6584 (1995).

N. Misawa et al., "Elucidation of an Astaxanthin Biosynthetic Pathway at the Level of the Biosynthesis Genes", Chemical Abstracts, vol. 123, No. 11, Sep. 1995.

E. Johnson, "Astaxanthin from Microbial Sources", Critical Reviews in Biotechnology, vol. 11, No. 4, 1991, pp. 297–326.

Czeczuga, B. Chemical Abstracts, vol. 98, No. 21 (May 23, 1983).

*Primary Examiner*—Robert A. Wax
*Assistant Examiner*—Nashaat T. Nashed
*Attorney, Agent, or Firm*—Foley & Lardner

[57] ABSTRACT

Disclosed are the following DNA strands relating to the synthesis of keto group-containing xanthophylls such as astaxanthin and the like, and the techniques relating to the production of xanthophylls by genetic engineering:

A DNA strand having a nucleotide sequence which encodes a polypeptides having and enzyme activity for converting a methylene group at the 4-position of a β-ionone ring into a keto group.

A DNA strand having a nucleotide sequence which encodes a polypeptide having an enzyme activity for converting a methylene group at the 4-position of a 3-hydroxy-β-ionone ring into a keto group.

A DNA strand having a nucleotide sequence which encodes a polypeptide having an enzyme activity for adding a hydroxyl group to the 3-carbon of a 4-keto-β-ionone ring.

It is possible to produce a variety of xanthophylls such as canthaxanthin, astaxanthin and the like by introducing the DNA strands into an appropriate microorganism such as *Escherichia coli* and the like.

19 Claims, 20 Drawing Sheets

A
↓

```
          237         246         255         264         273         282
      GTG CAT GCG CTG TGG TTT CTG GAC GCA GCG GCG CAT CCC ATC CTG GCG ATC GCA
      Met His Ala Leu Trp Phe Leu Asp Ala Ala Ala His Pro Ile Leu Ala Ile Ala 291         300         309         318         327         336
      AAT TTC CTG GGG CTG ACC TGG CTG TCG GTC GGA TTG TTC ATC ATC GCG CAT GAC
      Asn Phe Leu Gly Leu Thr Trp Leu Ser Val Gly Leu Phe Ile Ile Ala His Asp 345         354         363         372         381         390
      GCG ATG CAC GGG TCG GTG GTG CCG GGG CGT CCG CGC GCC AAT GCG GCG ATG GGC
      Ala Met His Gly Ser Val Val Pro Gly Arg Pro Arg Ala Asn Ala Ala Met Gly 399         408         417         426         435         444
      CAG CTT GTC CTG TGG CTG TAT GCC GGA TTT TCG TGG CGC AAG ATG ATC GTC AAG
      Gln Leu Val Leu Trp Leu Tyr Ala Gly Phe Ser Trp Arg Lys Met Ile Val Lys 453         462         471         480         489         498
      CAC ATG GCC CAT CAC CGC CAT GCC GGA ACC GAC GAC GAC CCC GAT TTC GAC CAT
      His Met Ala His His Arg His Ala Gly Thr Asp Asp Asp Pro Asp Phe Asp His 507         516         525         534         543         552
      GGC GGC CCG GTC CGC TGG TAC GCC CGC TTC ATC GGC ACC TAT TTC GGC TGG CGC
      Gly Gly Pro Val Arg Trp Tyr Ala Arg Phe Ile Gly Thr Tyr Phe Gly Trp Arg 561         570         579         588         597         606
      GAG GGG CTG CTG CTG CCC GTC ATC GTG ACG GTC TAT GCG CTG ATC CTT GGG GAT
      Glu Gly Leu Leu Leu Pro Val Ile Val Thr Val Tyr Ala Leu Ile Leu Gly Asp 615         624         633         642         651         660
      CGC TGG ATG TAC GTG GTC TTC TGG CCG CTG CCG TCG ATC CTG GCG TCG ATC CAG
      Arg Trp Met Tyr Val Val Phe Trp Pro Leu Pro Ser Ile Leu Ala Ser Ile Gln 669         678         687         696         705         714
      CTG TTC GTG TTC GGC ACC TGG CTG CCG CAC CGC CCC GGC CAC GAC GCG TTC CCG
      Leu Phe Val Phe Gly Thr Trp Leu Pro His Arg Pro Gly His Asp Ala Phe Pro 723         732         741         750         759         768
      GAC CGC CAC AAT GCG CGG TCG TCG CGG ATC AGC GAC CCC GTG TCG CTG CTG ACC
      Asp Arg His Asn Ala Arg Ser Ser Arg Ile Ser Asp Pro Val Ser Leu Leu Thr 777         786         795         804         813         822
      TGC TTT CAC TTT GGC GGT TAT CAT CAC GAA CAC CAC CTG CAC CCG ACG GTG CCG
      Cys Phe His Phe Gly Gly Tyr His His Glu His His Leu His Pro Thr Val Pro 831         840         849         858         867
      TGG TGG CGC CTG CCC AGC ACC CGC ACC AAG GGG GAC ACC GCA TGA
      Trp Trp Arg Leu Pro Ser Thr Arg Thr Lys Gly Asp Thr Ala ***
                                                              ↑
                                                              B
```

|  |  |  |  |  |  |
|---|---|---|---|---|---|
| 872 | 881 | 890 | 899 | 908 | 917 |
| ATG ACC AAT | TTC CTG ATC | GTC GTC GCC | ACC GTG CTG | GTG ATG GAG | TTG ACG GCC |
| Met Thr Asn | Phe Leu Ile | Val Val Ala | Thr Val Leu | Val Met Glu | Leu Thr Ala |
| 926 | 935 | 944 | 953 | 962 | 971 |
| TAT TCC GTC | CAC CGC TGG | ATC ATG CAC | GGC CCC CTG | GGC TGG GGC | TGG CAC AAG |
| Tyr Ser Val | His Arg Trp | Ile Met His | Gly Pro Leu | Gly Trp Gly | Trp His Lys |
| 980 | 989 | 998 | 1007 | 1016 | 1025 |
| TCC CAC CAC | GAG GAA CAC | GAC CAC GCG | CTG GAA AAG | AAC GAC CTG | TAC GGC CTG |
| Ser His His | Glu Glu His | Asp His Ala | Leu Glu Lys | Asn Asp Leu | Tyr Gly Leu |
| 1034 | 1043 | 1052 | 1061 | 1070 | 1079 |
| GTC TTT GCG | GTG ATC GCC | ACG GTG CTG | TTC ACG GTG | GGC TGG ATC | TGG GCG CCG |
| Val Phe Ala | Val Ile Ala | Thr Val Leu | Phe Thr Val | Gly Trp Ile | Trp Ala Pro |
| 1088 | 1097 | 1106 | 1115 | 1124 | 1133 |
| GTC CTG TGG | TGG ATC GCC | TTG GGC ATG | ACT GTC TAT | GGG CTG ATC | TAT TTC GTC |
| Val Leu Trp | Trp Ile Ala | Leu Gly Met | Thr Val Tyr | Gly Leu Ile | Tyr Phe Val |
| 1142 | 1151 | 1160 | 1169 | 1178 | 1187 |
| CTG CAT GAC | GGG CTG GTG | CAT CAG CGC | TGG CCG TTC | CGT TAT ATC | CCG CGC AAG |
| Leu His Asp | Gly Leu Val | His Gln Arg | Trp Pro Phe | Arg Tyr Ile | Pro Arg Lys |
| 1196 | 1205 | 1214 | 1223 | 1232 | 1241 |
| GGC TAT GCC | AGA CGC CTG | TAT CAG GCC | CAC CGC CTG | CAC CAT GCG | GTC GAG GGG |
| Gly Tyr Ala | Arg Arg Leu | Tyr Gln Ala | His Arg Leu | His His Ala | Val Glu Gly |
| 1250 | 1259 | 1268 | 1277 | 1286 | 1295 |
| CGC GAC CAT | TGC GTC AGC | TTC GGC TTC | ATC TAT GCG | CCC CCG GTC | GAC AAG CTG |
| Arg Asp His | Cys Val Ser | Phe Gly Phe | Ile Tyr Ala | Pro Pro Val | Asp Lys Leu |
| 1304 | 1313 | 1322 | 1331 | 1340 | 1349 |
| AAG CAG GAC | CTG AAG ATG | TCG GGC GTG | CTG CGG GCC | GAG GCG CAG | GAG CGC ACG |
| Lys Gln Asp | Leu Lys Met | Ser Gly Val | Leu Arg Ala | Glu Ala Gln | Glu Arg Thr |

TGA
---
...

```
        1357          1366          1375          1384          1393          1402
GTG ACC CAT GAC GTG CTG CTG GCA GGG GCG GGC CTT GCC AAC GGG CTG ATC GCC
Met Thr His Asp Val Leu Leu Ala Gly Ala Gly Leu Ala Asn Gly Leu Ile Ala 1411          1420          1429          1438          1447          1456
CTG GCG CTG CGC GCG GCG CGG CCC GAC CTG CGC GTG CTG CTG CTG GAC CAT GCC
Leu Ala Leu Arg Ala Ala Arg Pro Asp Leu Arg Val Leu Leu Leu Asp His Ala 1465          1474          1483          1492          1501          1510
GCA GGA CCG TCA GAC GGC CAC ACC TGG TCC TGC CAC GAC CCC GAC CTG TCG CCG
Ala Gly Pro Ser Asp Gly His Thr Trp Ser Cys His Asp Pro Asp Leu Ser Pro 1519          1528          1537          1546          1555          1564
GAC TGG CTG GCG CGG CTG AAG CCC CTG CGC CGC GCC AAC TGG CCC GAC CAG GAG
Asp Trp Leu Ala Arg Leu Lys Pro Leu Arg Arg Ala Asn Trp Pro Asp Gln Glu 1573          1582          1591          1600          1609          1618
GTG CGC TTT CCC CGC CAT GCC CGG CGG CTG GCC ACC GGT TAC GGG TCG CTG GAC
Val Arg Phe Pro Arg His Ala Arg Arg Leu Ala Thr Gly Tyr Gly Ser Leu Asp 1627          1636          1645          1654          1663          1672
GGG GCG GCG CTG GCG GAT GCG GTG GTC CGG TCG GGC GCC GAG ATC CGC TGG GAC
Gly Ala Ala Leu Ala Asp Ala Val Val Arg Ser Gly Ala Glu Ile Arg Trp Asp 1681          1690          1699          1708          1717          1726
AGC GAC ATC GCC CTG CTG GAT GCG CAG GGG GCG ACG CTG TCC TGC GGC ACC CGG
Ser Asp Ile Ala Leu Leu Asp Ala Gln Gly Ala Thr Leu Ser Cys Gly Thr Arg 1735          1744          1753          1762          1771          1780
ATC GAG GCG GGC GCG GTC CTG GAC GGG CGG GGC GCG CAG CCG TCG CGG CAT CTG
Ile Glu Ala Gly Ala Val Leu Asp Gly Arg Gly Ala Gln Pro Ser Arg His Leu 1789          1798          1807          1816          1825          1834
ACC GTG GGT TTC CAG AAA TTC GTG GGT GTC GAG ATC GAG ACC GAC CGC CCC CAC
Thr Val Gly Phe Gln Lys Phe Val Gly Val Glu Ile Glu Thr Asp Arg Pro His 1843          1852          1861          1870          1879          1888
GGC GTG CCC CGC CCG ATG ATC ATG GAC GCG ACC GTC ACC CAG CAG GAC GGG TAC
Gly Val Pro Arg Pro Met Ile Met Asp Ala Thr Val Thr Gln Gln Asp Gly Tyr 1897          1906          1915          1924          1933          1942
CGC TTC ATC TAT CTG CTG CCC TTC TCT CCG ACG CGC ATC CTG ATC GAG GAC ACG
Arg Phe Ile Tyr Leu Leu Pro Phe Ser Pro Thr Arg Ile Leu Ile Glu Asp Thr 1951          1960          1969          1978          1987          1996
CGC TAT TCC GAT GGC GGC GAT CTG GAC GAC GAC GCG CTG GCG GCG GCG TCC CAC
Arg Tyr Ser Asp Gly Gly Asp Leu Asp Asp Asp Ala Leu Ala Ala Ala Ser His
```

FIG. 3

```
          2005            2014            2023            2032            2041            2050
GAC TAT GCC CGC CAG CAG GGC TGG ACC GGG GCC GAG GTC CGG CGC GAA CGC GGC
Asp Tyr Ala Arg Gln Gln Gly Trp Thr Gly Ala Glu Val Arg Arg Glu Arg Gly 2059            2068            2077            2086            2095            2104
ATC CTT CCC ATC GCG CTG GCC CAT GAT GCG GCG GGC TTC TGG GCC GAT CAC GCG
Ile Leu Pro Ile Ala Leu Ala His Asp Ala Ala Gly Phe Trp Ala Asp His Ala 2113            2122            2131            2140            2149            2158
GCG GGG CCT GTT CCC GTG GGA CTG CGC GCG GGG TTC TTT CAT CCG GTC ACC GGC
Ala Gly Pro Val Pro Val Gly Leu Arg Ala Gly Phe Phe His Pro Val Thr Gly 2167            2176            2185            2194            2203            2212
TAT TCG CTG CCC TAT GCG GCA CAG GTG GCG GAC GTG GTG GCG GGT CTG TCC GGG
Tyr Ser Leu Pro Tyr Ala Ala Gln Val Ala Asp Val Val Ala Gly Leu Ser Gly 2221            2230            2239            2248            2257            2266
CCG CCC GGC ACC GAC GCG CTG CGC GGC GCC ATC CGC GAT TAC GCG ATC GAC CGG
Pro Pro Gly Thr Asp Ala Leu Arg Gly Ala Ile Arg Asp Tyr Ala Ile Asp Arg 2275            2284            2293            2302            2311            2320
GCG CGC CGC GAC CGC TTT CTG CGC CTT TTG AAC CGG ATG CTG TTC CGC GGC TGC
Ala Arg Arg Asp Arg Phe Leu Arg Leu Leu Asn Arg Met Leu Phe Arg Gly Cys 2329            2338            2347            2356            2365            2374
GCG CCC GAC CGG CGC TAT ACC CTG CTG CAG CGG TTC TAC CGC ATG CCG CAT GGA
Ala Pro Asp Arg Arg Tyr Thr Leu Leu Gln Arg Phe Tyr Arg Met Pro His Gly 2383            2392            2401            2410            2419            2428
CTG ATC GAA CGG TTC TAT GCC GGC CGG CTG AGC GTG GCG GAT CAG CTG CGC ATC
Leu Ile Glu Arg Phe Tyr Ala Gly Arg Leu Ser Val Ala Asp Gln Leu Arg Ile 2437            2446            2455            2464            2473            2482
GTG ACC GGC AAG CCT CCC ATT CCC CTT GGC ACG GCC ATC CGC TGC CTG CCC GAA
Val Thr Gly Lys Pro Pro Ile Pro Leu Gly Thr Ala Ile Arg Cys Leu Pro Glu 2491            2500            2509
CGT CCC CTG CTG AAG GAA AAC GCA TGA
Arg Pro Leu Leu Lys Glu Asn Ala ***
                              ↑
                              F
```

F I G. 4

```
              10         20         30         40         50         60
               •          •          •          •          •          •
           GGATC CGGCG ACCTT GCGGC GCTGC GCCGC GCGCC TTTGC TGGTG CCTGG GCCGG GTGGC
           CCTAG GCCGC TGGAA CGCCG CGACG CGGCG CGCGG AAACG ACCAC GGACC CGGCC CACCG 70         80         90        100        110        120
               •          •          •          •          •          •
           CAATG GTCGC AAGCA ACGGG GATGG AAACC GGCGA TGCGG GACTG TAGTC TGCGC GGATC
           GTTAC CAGCG TTCGT TGCCC CTACC TTTGG CCGCT ACGCC CTGAC ATCAG ACGCG CCTAG 130        140        150        160        170        180
               •          •          •          •          •          •
           GCCGG TCCGG GGGAC AAGAT GAGCG CACAT GCCCT GCCCA AGGCA GATCT GACCG CCACC
           CGGCC AGGCC CCCTG TTCTA CTCGC GTGTA CGGGA CGGGT TCCGT CTAGA CTGGC GGTGG 190        200        210        220      A 230        240
               •          •          •          •         ▼ •         •
           AGCCT GATCG TCTCG GGCGG CATCA TCGCC GCTTG GCTGG CCCTG CATGT GCATG CGCTG
           TCGGA CTAGC AGAGC CCGCC GTAGT AGCGG CGAAC CGACC GGGAC GTACA CGTAC GCGAC 250        260        270        280        290        300
               •          •          •          •          •          •
           TGGTT TCTGG ACGCA GCGGC GCATC CCATC CTGGC GATCG CAAAT TTCCT GGGGC TGACC
           ACCAA AGACC TGCGT CGCCG CGTAG GGTAG GACCG CTAGC GTTTA AAGGA CCCCG ACTGG 310        320        330        340        350        360
               •          •          •          •          •          •
           TGGCT GTCGG TCGGA TTGTT CATCA TCGCG CATGA CGCGA TGCAC GGGTC GGTGG TGCCG
           ACCGA CAGCC AGCCT AACAA GTAGT AGCGC GTACT GCGCt ACGTG CCCAG CCACC ACGGC 370        380        390        400        410        420
               •          •          •          •          •          •
           GGGCG TCCGC GCGCC AATGC GGCGA TGGGC CAGCT TGTCC TGTGG CTGTA TGCCG GATTT
           CCCGC AGGCG CGCGG TTACG CCGCT ACCCG GTCGA ACAGG ACACC GACAT ACGGC CTAAA 430        440        450        460        470        480
               •          •          •          •          •          •
           TCGTG GCGCA AGATG ATCGT CAAGC ACATG GCCCA TCACC GCCAT GCCGG AACCG ACGAC
           AGCAC CGCGT TCTAC TAGCA GTTCG TGTAC CGGGT AGTGG CGGTA CGGCC TTGGC TGCTG 490        500        510        520        530        540
               •          •          •          •          •          •
           GACCC CGATT TCGAC CATGG CGGCC CGGTC CGCTG GTACG CCCGC TTCAT CGGCA CCTAT
           CTGGG GCTAA AGCTG GTACC GCCGG GCCAG GCGAC CATGC GGGCG AAGTA GCCGT GGATA 550        560        570        580        590        600
               •          •          •          •          •          •
           TTCGG CTGGC GCGAG GGGCT GCTGC TGCCC GTCAT CGTGA CGGTC TATGC GCTGA TCCTT
           AAGCC GACCG CGCTC CCCGA CGACG ACGGG CAGTA GCACT GCCAG ATACG CGACT AGGAA 610        620        630        640        650        660
               •          •          •          •          •          •
           GGGGA TCGCT GGATG TACGT GGTCT TCTGG CCGCT GCCGT CGATC CTGGC GTCGA TCCAG
           CCCCT AGCGA CCTAC ATGCA CCAGA AGACC GGCGA CGGCA GCTAG GACCG CAGCT AGGTC
```

FIG. 5

```
         670        680        690        700        710        720
           .          .          .          .          .          .
CTGTT CGTGT TCGGC ACCTG GCTGC CGCAC CGCCC CGGCC ACGAC GCGTT CCCGG ACCGC
GACAA GCACA AGCCG TGGAC CGACG GCGTG GCGGG GCCGG TGCTG CGCAA GGGCC TGGCG 730        740        750        760        770        780
           .          .          .          .          .          .
CACAA TGCGC GGTCG TCGCG GATCA GCGAC CCCGT GTCGC TGCTG ACCTG CTTTC ACTTT
GTGTT ACGCG CCAGC AGCGC CTAGT CGCTG GGGCA CAGCG ACGAC TGGAC GAAAG TGAAA 790        800        810        820        830        840
           .          .          .          .          .          .
GGCGG TTATC ATCAC GAACA CCACC TGCAC CCGAC GGTGC CGTGG TGGCG CCTGC CCAGC
CCGCC AATAG TAGTG CTTGT GGTGG ACGTG GGCTG GGACG GCACC ACCGC GGACG GGTCG 850        860   C    870        880        890        900
           .          .   ↓      .          .          .          .
ACCCG CACCA AGGGG GACAC CGCAT GACCA ATTTC CTGAT CGTCG TCGCC ACCGT GCTGG
TGGGC GTGGT TCCCC CTGTG GCGTA CTGGT TAAAG GACTA GCAGC AGCGG TGGCA CGACC
                              ↑
         910        920      B 930        940        950        960
           .          .          .          .          .          .
TGATG GAGTT GACGG CCTAT TCCGT CCACC GCTGG ATCAT GCACG GCCCC TGGG CTGGG
ACTAC CTCAA CTGCC GGATA AGGCA GGTGG CGACC TAGTA CGTGC CGGGG GACCC GACCC 970        980        990        1000       1010       1020
           .          .          .          .          .          .
GCTGG CACAA GTCCC ACCAC GAGGA ACACG ACCAC GCGCT GGAAA AGAAC GACCT GTACG
CGACC GTGTT CAGGG TGGTG CTCCT TGTGG TGGTG CGCGA CCTTT TCTTG CTGGA CATGC 1030       1040       1050       1060       1070       1080
           .          .          .          .          .          .
GCCTG GTCTT TGCGG TGATC GCCAC GGTGC TGTTC ACGGT GGGCT GGATC TGGGC GCCGG
CGGAC CAGAA ACGCC ACTAG CGGTG CCACG ACAAG TGCCA CCCGA CCTAG ACCCG CGGCC 1090       1100       1110       1120       1130       1140
           .          .          .          .          .          .
TCCTG TGGTG GATCG CCTTG GGCAT GACTG TCTAT GGGCT GATCT ATTTC GTCCT GCATG
AGGAC ACCAC CTAGC GGAAC CCGTA CTGAC AGATA CCCGA CTAGA TAAAG CAGGA CGTAC 1150       1160       1170       1180       1190       1200
           .          .          .          .          .          .
ACGGG CTGGT GCATC AGCGC TGGCC GTTCC GTTAT ATCCC GCGCA AGGGC TATGC CAGAC
TGCCC GACCA CGTAG TCGCG ACCGG CAAGG CAATA TAGGG CGCGT TCCCG ATACG GTCTG 1210       1220       1230       1240       1250       1260
           .          .          .          .          .          .
GCCTG TATCA GGCCC ACCGC CTGCA CCATG CGGTC GAGGG GCGCG ACCAT TGCGT CAGCT
CGGAC ATAGT CCGGG TGGCG GACGT GGTAC GCCAG CTCCC CGCGC TGGTA ACGCA GTCGA 1270       1280       1290       1300       1310       1320
           .          .          .          .          .          .
TCGGC TTCAT CTATG CGCCC CCGGT CGACA AGCTG AAGCA GGACC TGAAG ATGTC GGGCG
AGCCG AAGTA GATAC GCGGG GGCCA GCTGT TCGAC TTCGT CCTGG ACTTC TACAG CCCGC
```

FIG. 6

```
         1330           1340       E 1350          1360          1370          1380
           .              .           ▼ .            .              .              .
       TGCTG  CGGGC  CGAGG  CGCAG  GAGCG  CACGT  GACCC  ATGAC  GTGCT  GCTGG  CAGGG  GCGGG
       ACGAC  GCCCG  GCTCC  GCGTC  CTCGC  GTGCA  CTGGG  TACTG  CACGA  CGACC  GTCCC  CGCCC
                                           ▲ D
         1390           1400          1410          1420          1430          1440
           .              .             .            .              .              .
       CCTTG  CCAAC  GGGCT  GATCG  CCCTG  GCGCT  GCGCG  CGGCG  CGGCC  CGACC  TGCGC  GTGCT
       GGAAC  GGTTG  CCCGA  CTAGC  GGGAC  CGCGA  CGCGC  GCCGC  GCCGG  GCTGG  ACGCG  CACGA 1450           1460          1470          1480          1490          1500
           .              .             .            .              .              .
       GCTGC  TGGAC  CATGC  CGCAG  GACCG  TCAGA  CGGCC  ACACC  TGGTC  CTGCC  ACGAC  CCCGA
       CGACG  ACCTG  GTACG  GCGTC  CTGGC  AGTCT  GCCGG  TGTGG  ACCAG  GACGG  TGCTG  GGGCT 1510           1520          1530          1540          1550          1560
           .              .             .            .              .              .
       CCTGT  CGCCG  GACTG  GCTGG  CGCGG  CTGAA  GCCCC  TGCGC  CGCGC  CAACT  GGCCC  GACCA
       GGACA  GCGGC  CTGAC  CGACC  GCGCC  GACTT  CGGGG  ACGCG  GCGCG  GTTGA  CCGGG  CTGGT 1570           1580          1590          1600          1610          1620
           .              .             .            .              .              .
       GGAGG  TGCGC  TTTCC  CCGCC  ATGCC  CGGCG  GCTGG  CCACC  GGTTA  CGGGT  CGCTG  GACGG
       CCTCC  ACGCG  AAAGG  GGCGG  TACGG  GCCGC  CGACC  GGTGG  CCAAT  GCCCA  GCGAC  CTGCC 1630           1640          1650          1660          1670          1680
           .              .             .            .              .              .
       GGCGG  CGCTG  GCGGA  TGCGG  TGGTC  CGGTC  GGGCG  CCGAG  ATCCG  CTGGG  ACAGC  GACAT
       CCGCC  GCGAC  CGCCT  ACGCC  ACCAG  GCCAG  CCCGC  GGCTC  TAGGC  GACCC  TGTCG  CTGTA 1690           1700          1710          1720          1730          1740
           .              .             .            .              .              .
       CGCCC  TGCTG  GATGC  GCAGG  GGGCG  ACGCT  GTCCT  GCGGC  ACCCG  GATCG  AGGCG  GGCGC
       GCGGG  ACGAC  CTACG  CGTCC  CCCGC  TGCGA  CAGGA  CGCCG  TGGGC  CTAGC  TCCGC  CCGCG 1750           1760          1770          1780          1790          1800
           .              .             .            .              .              .
       GGTCC  TGGAC  GGGCG  GGGCG  CGCAG  CCGTC  GCGGC  ATCTG  ACCGT  GGGTT  TCCAG  AAATT
       CCAGG  ACCTG  CCCGC  CCCGC  GCGTC  GGCAG  CGCCG  TAGAC  TGGCA  CCCAA  AGGTC  TTTAA 1810           1820          1830          1840          1850          1860
           .              .             .            .              .              .
       CGTGG  GTGTC  GAGAT  CGAGA  CCGAC  CGCCC  CCACG  GCGTG  CCCCG  CCCGA  TGATC  ATGGA
       GCACC  CACAG  CTCTA  GCTCT  GGCTG  GCGGG  GGTGC  CGCAC  GGGGC  GGGCT  ACTAG  TACCT 1870           1880          1890          1900          1910          1920
           .              .             .            .              .              .
       CGCGA  CCGTC  ACCCA  GCAGG  ACGGG  TACCG  CTTCA  TCTAT  CTGCT  GCCCT  TCTCT  CCGAC
       GCGCT  GGCAG  TGGGT  CGTCC  TGCCC  ATGGC  GAAGT  AGATA  GACGA  CGGGA  AGAGA  GGCTG 1930           1940          1950          1960          1970          1980
           .              .             .            .              .              .
       GCGCA  TCCTG  ATCGA  GGACA  CGCGC  TATTC  CGATG  GCGGC  GATCT  GGACG  ACGAC  GCGCT
       CGCGT  AGGAC  TAGCT  CCTGT  GCGCG  ATAAG  GCTAC  CGCCG  CTAGA  CCTGC  TGCTG  CGCGA
```

FIG. 7

```
         1990       2000       2010       2020       2030       2040
           .          .          .          .          .          .
GGCGG CGGCG TCCCA CGACT ATGCC CGCCA GCAGG GCTGG ACCGG GGCCG AGGTC CGGCG
CCGCC GCCGC AGGGT GCTGA TACGG CGGGT CGTCC CGACC TGGCC CCGGC TCCAG GCCGC 2050       2060       2070       2080       2090       2100
           .          .          .          .          .          .
CGAAC GCGGC ATCCT TCCCA TCGCG CTGGC CCATG ATGCG GCGGG CTTCT GGGCC GATCA
GCTTG CGCCG TAGGA AGGGT AGCGC GACCG GGTAC TACGC CGCCC GAAGA CCCGG CTAGT 2110       2120       2130       2140       2150       2160
           .          .          .          .          .          .
CGCGG CGGGG CCTGT TCCCG TGGGA CTGCG CGCGG GGTTC TTTCA TCCGG TCACC GGCTA
GCGCC GCCCC GGACA AGGGC ACCCT GACGC GCGCC CCAAG AAAGT AGGCC AGTGG CCGAT 2170       2180       2190       2200       2210       2220
           .          .          .          .          .          .
TTCGC TGCCC TATGC GGCAC AGGTG GCGGA CGTGG TGGCG GGTCT GTCCG GGCCG CCCGG
AAGCG ACGGG ATACG CCGTG TCCAC CGCCT GCACC ACCGC CCAGA CAGGC CCGGC GGGCC 2230       2240       2250       2260       2270       2280
           .          .          .          .          .          .
CACCG ACGCG CTGCG CGGCG CCATC CGCGA TTACG CGATC GACCG GGCGC GCCGC GACCG
GTGGC TGCGC GACGC GCCGC GGTAG GCGCT AATGC GCTAG CTGGC CCGCG CGGCG CTGGC 2290       2300       2310       2320       2330       2340
           .          .          .          .          .          .
CTTTC TGCGC CTTTT GAACC GGATG CTGTT CCGCG GCTGC GCGCC CGACC GGCGC TATAC
GAAAG ACGCG GAAAA CTTGG CCTAC GACAA GGCGC CGACG CGCGG GCTGG CCGCG ATATG 2350       2360       2370       2380       2390       2400
           .          .          .          .          .          .
CCTGC TGCAG CGGTT CTACC GCATG CCGCA TGGAC TGATC GAACG GTTCT ATGCC GGCCG
GGACG ACGTC GCCAA GATGG CGTAC GGCGT ACCTG ACTAG CTTGC CAAGA TACGG CCGGC 2410       2420       2430       2440       2450       2460
           .          .          .          .          .          .
GCTGA GCGTG GCGGA TCAGC TGCGC ATCGT GACCG GCAAG CCTCC CATTC CCCTT GGCAC
CGACT CGCAC CGCCT AGTCG ACGCG TAGCA CTGGC CGTTC GGAGG GTAAG GGGAA CCGTG 2470       2480       2490       2500       2510       2520
           .          .          .          .          .          .
GGCCA TCCGC TGCCT GCCCG AACGT CCCCT GCTGA AGGAA AACGC ATGAA CGCCC ATTCG
CCGGT AGGCG ACGGA CGGGC TTGCA GGGGA CGACT TCCTT TTGCG TACTT GCGGG TAAGC 2530       2540       2550       2560       2570       2580
           .          .          .          .          .          .
CCCGC GGCCA AGACC GCCAT CGTGA TCGGC GCAGG CTTTG GCGGG CTGGC CCTGG CCATC
GGGCG CCGGT TCTGG CGGTA GCACT AGCCG CGTCC GAAAC CGCCC GACCG GGACC GGTAG 2590       2600       2610       2620       2630       2640
           .          .          .          .          .          .
CGCCT GCAGT CCGCG GGCAT CGCCA CCACC CTGGT CGAGG CCCGG GACAA GCCCG GCGGG
GCGGA CGTCA GGCGC CCGTA GCGGT GGTGG GACCA GCTCC GGGCC CTGTT CGGGC CGCCC
```

FIG. 8

```
           2650        2660        2670        2680        2690        2700
             .           .           .           .           .           .
CGCGC CTATG TCTGG CACGA TCAGG GCCAT CTCTT CGACG CGGGC CCGAC CGTCA TCACC
GCGCG GATAC AGACC GTGCT AGTCC CGGTA GAGAA GCTGC GCCCG GGCTG GCAGT AGTGG 2710        2720        2730        2740        2750        2760
             .           .           .           .           .           .
GACCC CGATG CGCTG AAAGA GCTGT GGGCC CTGAC CGGGC AGGAC ATGGC GCGCG ACGTG
CTGGG GCTAC GCGAC TTTCT CGACA CCCGG GACTG GCCCG TCCTG TACCG CGCGC TGCAC 2770        2780        2790        2800        2810        2820
             .           .           .           .           .           .
ACGCT GATGC CGGTC TCGCC CTTCT ATCGG CTGAT GTGGC CGGGC GGGAA GGTCT TCGAT
TGCGA CTACG GCCAG AGCGG GAAGA TAGCC GACTA CACCG GCCCG CCCTT CCAGA AGCTA 2830        2840        2850        2860        2870        2880
             .           .           .           .           .           .
TACGT GAACG AGGCC GATCC AGGGT CTGGG TCTTG CCGTG CCAGG TGAAG CTGTT GCCGT
ATGCA CTTGC TCCGG CTAGG TCCCA GACCC AGAAC GGCAC GGTCC ACTTC GACAA CGGCA

2886
    .
GGATC C
CCTAG G
```

FIG. 9

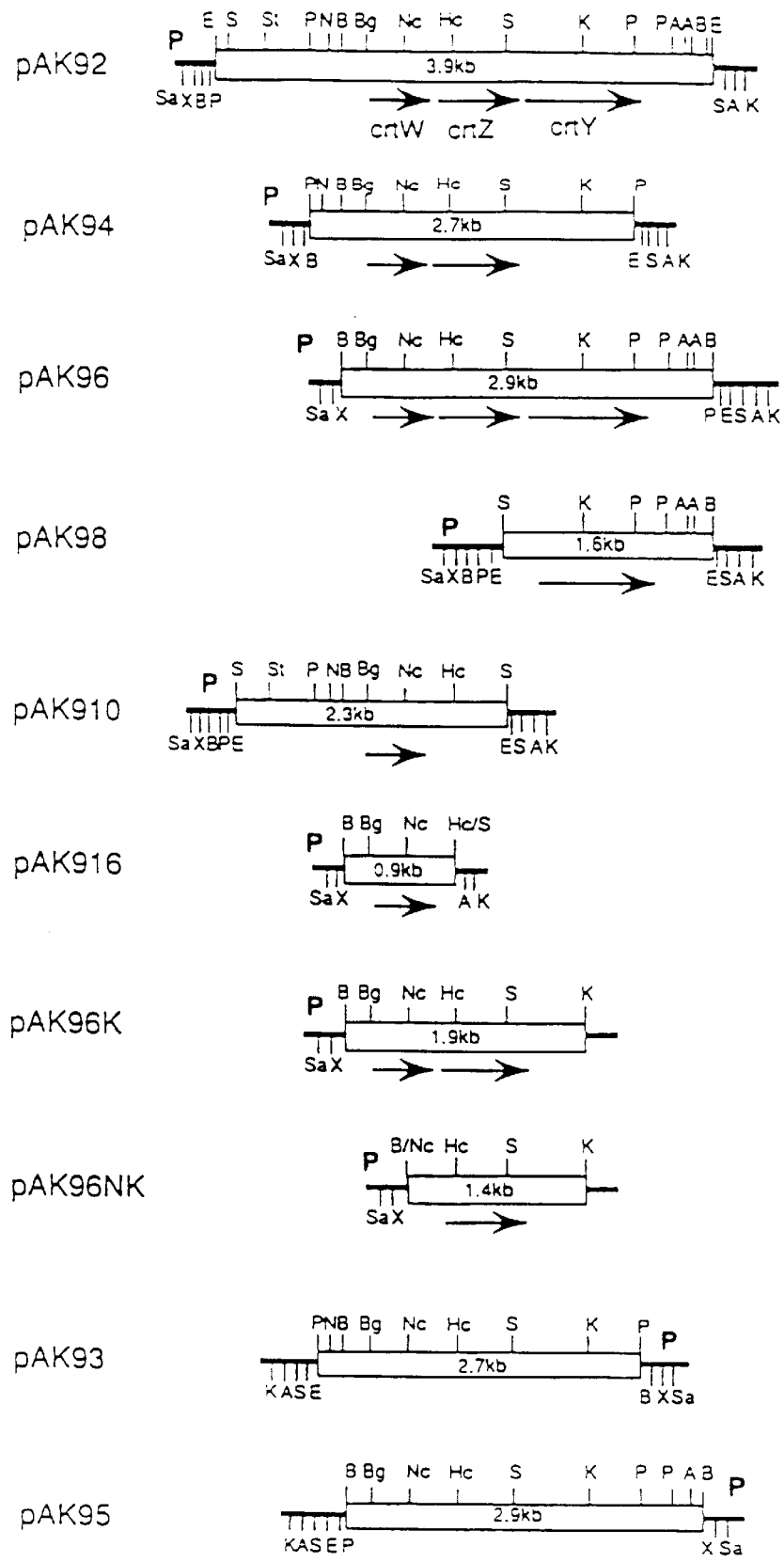
F I G. 12

A↓
```
         110       120       130       140       150
    ATGTCCGGACGGAAGCCTGGCACAACTGGCGACACGATCGTCAATCTCGGTCTGACCGCC
  1 MetSerGlyArgLysProGlyThrThrGlyAspThrIleValAsnLeuGlyLeuThrAla 160       170       180       190       200       210
    GCGATCCTGCTGTGCTGGCTGGTCCTGCACGCCTTTACGCTATGGTTGCTAGATGCGGCC
 21 AlaIleLeuLeuCysTrpLeuValLeuHisAlaPheThrLeuTrpLeuLeuAspAlaAla 220       230       240       250       260       270
    GCGCATCCGCTGCTTGCCGTGCTGTGCCTGGCTGGGCTGACCTGGCTGTCGGTCGGGCTG
 41 AlaHisProLeuLeuAlaValLeuCysLeuAlaGlyLeuThrTrpLeuSerValGlyLeu 280       290       300       310       320       330
    TTCATCATCGCGCATGACGCAATGCACGGGTCCGTGGTGCCGGGGCGGCCGCGCGCCAAT
 61 PheIleIleAlaHisAspAlaMetHisGlySerValValProGlyArgProArgAlaAsn 340       350       360       370       380       390
    GCGGCGATCGGGCAACTGGCGCTGTGGCTCTATGCGGGGTTCTCGTGGCCCAAGCTGATC
 81 AlaAlaIleGlyGlnLeuAlaLeuTrpLeuTyrAlaGlyPheSerTrpProLysLeuIle 400       410       420       430       440       450
    GCCAAGCACATGACGCATCACCGGCACGCCGGCACCGACAACGATCCCGATTTCGGTCAC
101 AlaLysHisMetThrHisHisArgHisAlaGlyThrAspAsnAspProAspPheGlyHis 460       470       480       490       500       510
    GGAGGGCCCGTGCGCTGGTACGGCAGCTTCGTCTCCACCTATTTCGGCTGGCGAGAGGGA
121 GlyGlyProValArgTrpTyrGlySerPheValSerThrTyrPheGlyTrpArgGluGly 520       530       540       550       560       570
    CTGCTGCTACCGGTGATCGTCACCACCTATGCGCTGATCCTGGGCGATCGCTGGATGTAT
141 LeuLeuLeuProValIleValThrThrTyrAlaLeuIleLeuGlyAspArgTrpMetTyr 580       590       600       610       620       630
    GTCATCTTCTGGCCGGTCCCGGCCGTTCTGGCGTCGATCCAGATTTTCGTCTTCGGAACT
161 ValIlePheTrpProValProAlaValLeuAlaSerIleGlnIlePheValPheGlyThr 640       650       660       670       680       690
    TGGCTGCCCCACCGCCCGGGACATGACGATTTTCCCGACCGGCACAACGCGAGGTCGACC
181 TrpLeuProHisArgProGlyHisAspAspPheProAspArgHisAsnAlaArgSerThr 700       710       720       730       740       750
    GGCATCGGCGACCCGTTGTCACTACTGACCTGCTTCCATTTCGGCGGCTATCACCACGAA
201 GlyIleGlyAspProLeuSerLeuLeuThrCysPheHisPheGlyGlyTyrHisHisGlu
```

FIG. 13

```
      760       770       780       790       800       810
    CATCACCTGCATCCGCATGTGCCGTGGTGGCGCCTGCCTCGTACACGCAAGACCGGAGGC
221 HisHisLeuHisProHisValProTrpTrpArgLeuProArgThrArgLysThrGlyGly 820   827
    CGCGCATGA
241 ArgAla***
         ↑B
```

FIG. 14

C↓
```
      330       840       850       860       870       880
ATGACGCAATTCCTCATTGTCGTGGCGACAGTCCTCGTGATGGAGCTGACCGCCTATTCC
  1 MetThrGlnPheLeuIleValValAlaThrValLeuValMetGluLeuThrAlaTyrSer 890       900       910       920       930       940
GTCCACCGCTGGATTATGCACGGCCCCCTAGGCTGGGGCTGGCACAAGTCCCATCACGAA
 21 ValHisArgTrpIleMetHisGlyProLeuGlyTrpGlyTrpHisLysSerHisHisGlu 950       960       970       980       990      1000
GAGCACGACCACGCGTTGGAGAAGAACGACCTCTACGGCGTCGTCTTCGCGGTGCTGGCG
 41 GluHisAspHisAlaLeuGluLysAsnAspLeuTyrGlyValValPheAlaValLeuAla 1010      1020      1030      1040      1050      1060
ACGATCCTCTTCACCGTGGGCGCCTATTGGTGGCCGGTGCTGTGGTGGATCGCCCTGGGC
 61 ThrIleLeuPheThrValGlyAlaTyrTrpTrpProValLeuTrpTrpIleAlaLeuGly 1070      1080      1090      1100      1110      1120
ATGACGGTCTATGGGTTGATCTATTTCATCCTGCACGACGGGCTTGTGCATCAACGCTGG
 81 MetThrValTyrGlyLeuIleTyrPheIleLeuHisAspGlyLeuValHisGlnArgTrp 1130      1140      1150      1160      1170      1180
CCGTTTCGGTATATTCCGCGGCGGGGCTATTTCCGCAGGCTCTACCAAGCTCATCGCCTG
101 ProPheArgTyrIleProArgArgGlyTyrPheArgArgLeuTyrGlnAlaHisArgLeu 1190      1200      1210      1220      1230      1240
CACCACGCGGTCGAGGGGCGGGACCACTGCGTCAGCTTCGGCTTCATCTATGCCCCACCC
121 HisHisAlaValGluGlyArgAspHisCysValSerPheGlyPheIleTyrAlaProPro 1250      1260      1270      1280      1290      1300
GTGGACAAGCTGAAGCAGGATCTGAAGCGGTCGGGTGTCCTGCGCCCCAGGACGAGCGT
141 ValAspLysLeuLysGlnAspLeuLysArgSerGlyValLeuArgProGlnAspGluArg

1312
      CCGTCGTGA
161 ProSer***
         ↑D
```

FIG. 15

```
             10         20         30         40         50         60
      CTGCA GGCCG GGCCC GGTGG CCAAT GGTCG CAACC GGCAG GACTG GAACA GGACG GCGGG
      GACGT CCGGC CCGGG CCACC GGTTA CCAGC GTTGG CCGTC CTGAC CTTGT CCTGC CGCCC
                                                     A↓
             70         80         90                    110        120
      CCGGT CTAGG CTGTC GCCCT ACGCA GCAGG AGTTT CGGAT GTCCG GACGG AAGCC TGGCA
      GGCCA GATCC GACAG CGGGA TGCGT CGTCC TCAAA GCCTA CAGGC CTGCC TTCGG ACCGT 130        140        150        160        170        180
      CAACT GGCGA CACGA TCGTC AATCT CGGTC TGACC GCCGC GATCC TGCTG TGCTG GCTGG
      GTTGA CCGCT GTGCT AGCAG TTAGA GCCAG ACTGG CGGCG CTAGG ACGAC ACGAC CGACC 190        200        210        220        230        240
      TCCTG CACGC CTTTA CGCTA TGGTT GCTAG ATGCG GCCGC GCATC CGCTG CTTGC CGTGC
      AGGAC GTGCG GAAAT GCGAT ACCAA CGATC TACGC CGGCG CGTAG GCGAC GAACG GCACG 250        260        270        280        290        300
      TGTGC CTGGC TGGGC TGACC TGGCT GTCGG TCGGG CTGTT CATCA TCGCG CATGA CGCAA
      ACACG GACCG ACCCG ACTGG ACCGA CAGCC AGCCC GACAA GTAGT AGCGC GTACT GCGTT 310        320        330        340        350        360
      TGCAC GGGTC CGTGG TGCCG GGGCG GCCGC GCGCC AATGC GGCGA TCGGG CAACT GGCGC
      ACGTG CCCAG GCACC ACGGC CCCGC CGGCG CGCGG TTACG CCGCT AGCCC GTTGA CCGCG 370        380        390        400        410        420
      TGTGG CTCTA TGCGG GGTTC TCGTG GCCCA AGCTG ATCGC CAAGC ACATG ACGCA TCACC
      ACACC GAGAT ACGCC CCAAG AGCAC CGGGT TCGAC TAGCG GTTCG TGTAC TGCGT AGTGG 430        440        450        460        470        480
      GGCAC GCCGG CACCG ACAAC GATCC CGATT TCGGT CACGG AGGGC CCGTG CGCTG GTACG
      CCGTG CGGCC GTGGC TGTTG CTAGG GCTAA AGCCA GTGCC TCCCG GGCAC GCGAC CATGC 490        500        510        520        530        540
      GCAGC TTCGT CTCCA CCTAT TTCGG CTGGC GAGAG GGACT GCTGC TACCG GTGAT CGTCA
      CGTCG AAGCA GAGGT GGATA AAGCC GACCG CTCTC CCTGA CGACG ATGGC CACTA GCAGT 550        560        570        580        590        600
      CCACC TATGC GCTGA TCCTG GGCGA TCGCT GGATG TATGT CATCT TCTGG CCGGT CCCGG
      GGTGG ATACG CGACT AGGAC CCGCT AGCGA CCTAC ATACA GTAGA AGACC GGCCA GGGCC 610        620        630        640        650        660
      CCGTT CTGGC GTCGA TCCAG ATTTT CGTCT TCGGA ACTTG GCTGC CCCAC CGCCC GGGAC
      GGCAA GACCG CAGCT AGGTC TAAAA GCAGA AGCCT TGAAC CGACG GGGTG GCGGG CCCTG 670        680        690        700        710        720
      ATGAC GATTT TCCCG ACCGG CACAA CGCGA GGTCG ACCGG CATCG GCGAC CCGTT GTCAC
      TACTG CTAAA AGGGC TGGCC GTGTT GCGCT CCAGC TGGCC GTAGC CGCTG GGCAA CAGTG
```

F I G. 16

```
         730        740        750        760        770        780
    TACTG ACCTG CTTCC ATTTC GGCGG CTATC ACCAC GAACA TCACC TGCAT CCGCA TGTGC
    ATGAC TGGAC GAAGG TAAAG CCGCC GATAG TGGTG CTTGT AGTGG ACGTA GGCGT ACACG 790        800        810        820  C↓    830        840
    CGTGG TGGCG CCTGC CTCGT ACACG CAAGA CCGGA GGCCG CGCAT GACGC AATTC CTCAT
    GCACC ACCGC GGACG GAGCA TGTGC GTTCT GGCCT CCGGC GCGTA CTGCG TTAAG GAGTA
                                                    ↑B
         850        860        870        880        890        900
    TGTCG TGGCG ACAGT CCTCG TGATG GAGCT GACCG CCTAT TCCGT CCACC GCTGG ATTAT
    ACAGC ACCGC TGTCA GGAGC ACTAC CTCGA CTGGC GGATA AGGCA GGTGG CGACC TAATA 910        920        930        940        950        960
    GCACG GCCCC CTAGG CTGGG GCTGG CACAA GTCCC ATCAC GAAGA GCACG ACCAC GCGTT
    CGTGC CGGGG GATCC GACCC CGACC GTGTT CAGGG TAGTG CTTCT CGTGC TGGTG CGCAA 970        980        990       1000       1010       1020
    GGAGA AGAAC GACCT CTACG GCGTC GTCTT CGCGG TGCTG GCGAC GATCC TCTTC ACCGT
    CCTCT TCTTG CTGGA GATGC CGCAG CAGAA GCGCC ACGAC CGCTG CTAGG AGAAG TGGCA 1030       1040       1050       1060       1070       1080
    GGGCG CCTAT TGGTG GCCGG TGCTG TGGTG GATCG CCCTG GGCAT GACGG TCTAT GGGTT
    CCCGC GGATA ACCAC CGGCC ACGAC ACCAC CTAGC GGGAC CCGTA CTGCC AGATA CCCAA 1090       1100       1110       1120       1130       1140
    GATCT ATTTC ATCCT GCACG ACGGG CTTGT GCATC AACGC TGGCC GTTTC GGTAT ATTCC
    CTAGA TAAAG TAGGA CGTGC TGCCC GAACA CGTAG TTGCG ACCGG CAAAG CCATA TAAGG 1150       1160       1170       1180       1190       1200
    GCGGC GGGGC TATTT CCGCA GGCTC TACCA AGCTC ATCGC CTGCA CCACG CGGTC GAGGG
    CGCCG CCCCG ATAAA GGCGT CCGAG ATGGT TCGAG TAGCG GACGT GGTGC GCCAG CTCCC 1210       1220       1230       1240       1250       1260
    GCGGG ACCAC TGCGT CAGCT TCGGC TTCAT CTATG CCCCA CCCGT GGACA AGCTG AAGCA
    CGCCC TGGTG ACGCA GTCGA AGCCG AAGTA GATAC GGGGT GGGCA CCTGT TCGAC TTCGT 1270       1280       1290       1300       1310       1320
    GGATC TGAAG CGGTC GGGTG TCCTG CGCCC CCAGG ACGAG CGTCC GTCGT GATCT CTGAT
    CCTAG ACTTC GCCAG CCCAC AGGAC GCGGG GGTCC TGCTC GCAGG CAGCA CTAGA GACTA
                                                              ↑D
        1330       1340       1350       1360       1370       1380
    CCCGG CGTGG CCGCA TGAAA TCCGA CGTGC TGCTG GCAGG GGCCG GCCTT GCCAA CGGAC
    GGGCC GCACC GGCGT ACTTT AGGCT GCACG ACGAC CGTCC CCGGC CGGAA CGGTT GCCTG 1390       1400       1410       1420       1430       1440
    TGATC GCGCT GGCGA TCCGC AAGGC GCGGC CCGAC CTTCG CGTGC TGCTG CTGGA CCGTG
    ACTAG CGCGA CCGCT AGGCG TTCCG CGCCG GGCTG GAAGC GCACG ACGAC GACCT GGCAC
```

FIG. 17

```
          1450      1460      1470      1480      1490      1500
CGGCG GGCGC CTCGG ACGGG CATAC TTGGT CCTGC CACGA CACCG ATTTG GCGCC GCACT
GCCGC CCGCG GAGCC TGCCC GTATG AACCA GGACG GTGCT GTGGC TAAAC CGCGG CGTGA 1510      1520      1530      1540      1550      1560
GGCTG GACCG CCTGA AGCCG ATCAG GCGTG GCGAC TGGCC CGATC AGGAG GTGCG GTTCC
CCGAC CTGGC GGACT TCGGC TAGTC CGCAC CGCTG ACCGG GCTAG TCCTC CACGC CAAGG 1570      1580      1590      1600      1610      1620
CAGAC CATTC GCGAA GGCTC CGGGC CGGAT ATGGC TCGAT CGACG GGCGG GGGCT GATGC
GTCTG GTAAG CGCTT CCGAG GCCCG GCCTA TACCG AGCTA GCTGC CCGCC CCCGA CTACG

1631
GTGCG GTGAC C
CACGC CACTG G
```

FIG. 18 pPC11
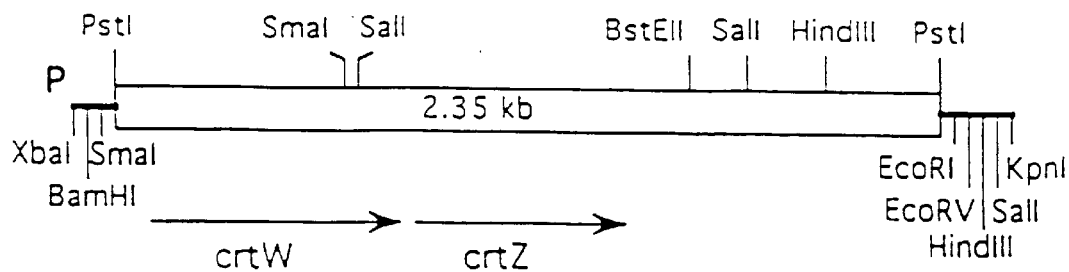
pPC13
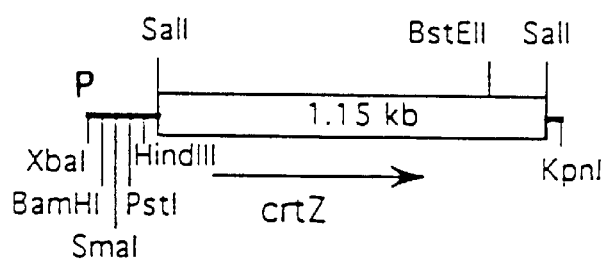
pPC17
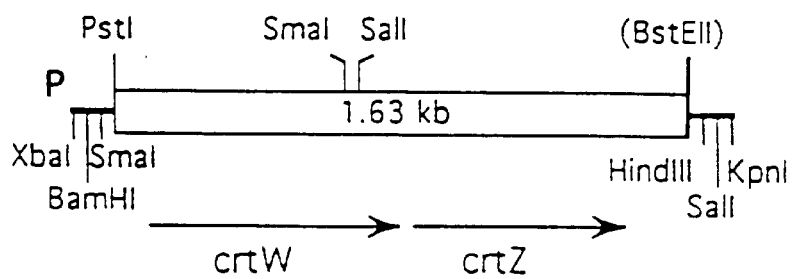
pPC17-3
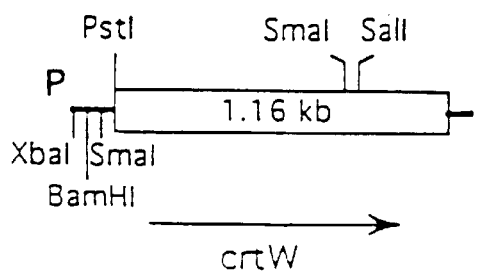
F I G. 19

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 639 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: 1..636

(ix) FEATURE:
      (A) NAME/KEY: mat_peptide
      (B) LOCATION: 1..636

(xi) SEQUENCE DESCRIPTION: SEQ ID NO:1:

```
GTG CAT GCG CTG TGG TTT CTG GAC GCA GCG GCG CAT CCC ATC CTG GCG        48
Val His Ala Leu Trp Phe Leu Asp Ala Ala Ala His Pro Ile Leu Ala
 1               5                  10                  15

ATC GCA AAT TTC CTG GGG CTG ACC TGG CTG TCG GTC GGA TTG TTC ATC        96
Ile Ala Asn Phe Leu Gly Leu Thr Trp Leu Ser Val Gly Leu Phe Ile
                20                  25                  30

ATC GCG CAT GAC GCG ATG CAC GGG TCG GTG GTG CCG GGG CGT CCG CGC       144
Ile Ala His Asp Ala Met His Gly Ser Val Val Pro Gly Arg Pro Arg
            35                  40                  45

GCC AAT GCG GCG ATG GGC CAG CTT GTC CTG TGG CTG TAT GCC GGA TTT       192
Ala Asn Ala Ala Met Gly Gln Leu Val Leu Trp Leu Tyr Ala Gly Phe
        50                  55                  60

TCG TGG CGC AAG ATG ATC GTC AAG CAC ATG GCC CAT CAC CGC CAT GCC       240
Ser Trp Arg Lys Met Ile Val Lys His Met Ala His His Arg His Ala
 65                 70                  75                  80

GGA ACC GAC GAC GAC CCC GAT TTC GAC CAT GGC GGC CCG GTC CGC TGG       288
Gly Thr Asp Asp Asp Pro Asp Phe Asp His Gly Gly Pro Val Arg Trp
                85                  90                  95

TAC GCC CGC TTC ATC GGC ACC TAT TTC GGC TGG CGC GAG GGG CTG CTG       336
Tyr Ala Arg Phe Ile Gly Thr Tyr Phe Gly Trp Arg Glu Gly Leu Leu
               100                 105                 110

CTG CCC GTC ATC GTG ACG GTC TAT GCG CTG ATC CTT GGG GAT CGC TGG       384
Leu Pro Val Ile Val Thr Val Tyr Ala Leu Ile Leu Gly Asp Arg Trp
           115                 120                 125

ATG TAC GTG GTC TTC TGG CCG CTG CCG TCG ATC CTG GCG TCG ATC CAG       432
Met Tyr Val Val Phe Trp Pro Leu Pro Ser Ile Leu Ala Ser Ile Gln
       130                 135                 140

CTG TTC GTG TTC GGC ACC TGG CTG CCG CAC CGC CCC GGC CAC GAC GCG       480
Leu Phe Val Phe Gly Thr Trp Leu Pro His Arg Pro Gly His Asp Ala
145                 150                 155                 160

TTC CCG GAC CGC CAC AAT GCG CGG TCG TCG CGG ATC AGC GAC CCC GTG       528
Phe Pro Asp Arg His Asn Ala Arg Ser Ser Arg Ile Ser Asp Pro Val
                165                 170                 175

TCG CTG CTG ACC TGC TTT CAC TTT GGC GGT TAT CAT CAC GAA CAC CAC       576
Ser Leu Leu Thr Cys Phe His Phe Gly Gly Tyr His His Glu His His
                180                 185                 190

CTG CAC CCG ACG GTG CCG TGG TGG CGC CTG CCC AGC ACC CGC ACC AAG       624
Leu His Pro Thr Val Pro Trp Trp Arg Leu Pro Ser Thr Arg Thr Lys
            195                 200                 205

GGG GAC ACC GCA TGA                                                   639
Gly Asp Thr Ala
```

(2) INFORMATION FOR SEQ ID NO:2:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:2:

```
Val His Ala Leu Trp Phe Leu Asp Ala Ala His Pro Ile Leu Ala
 1               5                  10                  15

Ile Ala Asn Phe Leu Gly Leu Thr Trp Leu Ser Val Gly Leu Phe Ile
             20                  25                  30

Ile Ala His Asp Ala Met His Gly Ser Val Val Pro Gly Arg Pro Arg
             35                  40                  45

Ala Asn Ala Ala Met Gly Gln Leu Val Leu Trp Leu Tyr Ala Gly Phe
         50                  55                  60

Ser Trp Arg Lys Met Ile Val Lys His Met Ala His His Arg His Ala
 65                  70                  75                  80

Gly Thr Asp Asp Pro Asp Phe Asp His Gly Gly Pro Val Arg Trp
                 85                  90                  95

Tyr Ala Arg Phe Ile Gly Thr Tyr Phe Gly Trp Arg Glu Gly Leu Leu
                100                 105                 110

Leu Pro Val Ile Val Thr Val Tyr Ala Leu Ile Leu Gly Asp Arg Trp
                115                 120                 125

Met Tyr Val Val Phe Trp Pro Leu Pro Ser Ile Leu Ala Ser Ile Gln
130                 135                 140

Leu Phe Val Phe Gly Thr Trp Leu Pro His Arg Pro Gly His Asp Ala
145                 150                 155                 160

Phe Pro Asp Arg His Asn Ala Arg Ser Ser Arg Ile Ser Asp Pro Val
                165                 170                 175

Ser Leu Leu Thr Cys Phe His Phe Gly Gly Tyr His His Glu His His
                180                 185                 190

Leu His Pro Thr Val Pro Trp Trp Arg Leu Pro Ser Thr Arg Thr Lys
                195                 200                 205

Gly Asp Thr Ala
                210
```

(2) INFORMATION FOR SEQ ID NO:3:

(i) SEQUENCE CHARACTERISTICS:
        (A) LENGTH: 489 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..486

(ix) FEATURE:
        (A) NAME/KEY: mat_peptide
        (B) LOCATION: 1..486

(xi) SEQUENCE DESCRIPTION: SEQ ID NO:3:

```
ATG ACC AAT TTC CTG ATC GTC GTC GCC ACC GTG CTG GTG ATG GAG TTG      48
Met Thr Asn Phe Leu Ile Val Val Ala Thr Val Leu Val Met Glu Leu
 1               5                  10                  15

ACG GCC TAT TCC GTC CAC CGC TGG ATC ATG CAC GGC CCC CTG GGC TGG      96
```

```
Thr Ala Tyr Ser Val His Arg Trp Ile Met His Gly Pro Leu Gly Trp
            20                  25                  30

GGC TGG CAC AAG TCC CAC CAC GAG GAA CAC GAC CAC GCG CTG GAA AAG        144
Gly Trp His Lys Ser His His Glu Glu His Asp His Ala Leu Glu Lys
        35                  40                  45

AAC GAC CTG TAC GGC CTG GTC TTT GCG GTG ATC GCC ACG GTG CTG TTC        192
Asn Asp Leu Tyr Gly Leu Val Phe Ala Val Ile Ala Thr Val Leu Phe
    50                  55                  60

ACG GTG GGC TGG ATC TGG GCG CCG GTC CTG TGG TGG ATC GCC TTG GGC        240
Thr Val Gly Trp Ile Trp Ala Pro Val Leu Trp Trp Ile Ala Leu Gly
65                  70                  75                  80

ATG ACT GTC TAT GGG CTG ATC TAT TTC GTC CTG CAT GAC GGG CTG GTG        288
Met Thr Val Tyr Gly Leu Ile Tyr Phe Val Leu His Asp Gly Leu Val
                85                  90                  95

CAT CAG CGC TGG CCG TTC CGT TAT ATC CCG CGC AAG GGC TAT GCC AGA        336
His Gln Arg Trp Pro Phe Arg Tyr Ile Pro Arg Lys Gly Tyr Ala Arg
            100                 105                 110

CGC CTG TAT CAG GCC CAC CGC CTG CAC CAT GCG GTC GAG GGG CGC GAC        384
Arg Leu Tyr Gln Ala His Arg Leu His His Ala Val Glu Gly Arg Asp
        115                 120                 125

CAT TGC GTC AGC TTC GGC TTC ATC TAT GCG CCC CCG GTC GAC AAG CTG        432
His Cys Val Ser Phe Gly Phe Ile Tyr Ala Pro Pro Val Asp Lys Leu
    130                 135                 140

AAG CAG GAC CTG AAG ATG TCG GGC GTG CTG CGG GCC GAG GCG CAG GAG        480
Lys Gln Asp Leu Lys Met Ser Gly Val Leu Arg Ala Glu Ala Gln Glu
145                 150                 155                 160

CGC ACG TGA                                                             489
Arg Thr
```

(2) INFORMATION FOR SEQ ID NO:4:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Leu Val Phe Ala Val Ile Ala Thr Val Leu Phe
    50                  55                  60

Thr Val Gly Trp Ile Trp Ala Pro Val Leu Trp Trp Ile Ala Leu Gly
65                  70                  75                  80

Met Thr Val Tyr Gly Leu Ile Tyr Phe Val Leu His Asp Gly Leu Val
                85                  90                  95

His Gln Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Met Ser Gly Val Leu Arg Ala Glu Ala Gln Glu
145                 150                 155                 160
```

Arg Thr (2) INFORMATION FOR SEQ ID NO:5:

(i) SEQUENCE CHARACTERISTICS:
        (A) LENGTH: 1161 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1158

(ix) FEATURE:
        (A) NAME/KEY: mat_peptide
        (B) LOCATION: 1..1158

(xi) SEQUENCE DESCRIPTION: SEQ ID NO:5:

```
GTG ACC CAT GAC GTG CTG CTG GCA GGG GCG GGC CTT GCC AAC GGG CTG        48
Val Thr His Asp Val Leu Leu Ala Gly Ala Gly Leu Ala Asn Gly Leu
 1               5                  10                  15

ATC GCC CTG GCG CTG CGC GCG GCG CGG CCC GAC CTG CGC GTG CTG CTG        96
Ile Ala Leu Ala Leu Arg Ala Ala Arg Pro Asp Leu Arg Val Leu Leu
             20                  25                  30

CTG GAC CAT GCC GCA GGA CCG TCA GAC GGC CAC ACC TGG TCC TGC CAC       144
Leu Asp His Ala Ala Gly Pro Ser Asp Gly His Thr Trp Ser Cys His
         35                  40                  45

GAC CCC GAC CTG TCG CCG GAC TGG CTG GCG CGG CTG AAG CCC CTG CGC       192
Asp Pro Asp Leu Ser Pro Asp Trp Leu Ala Arg Leu Lys Pro Leu Arg
 50                  55                  60

CGC GCC AAC TGG CCC GAC CAG GAG GTG CGC TTT CCC CGC CAT GCC CGG       240
Arg Ala Asn Trp Pro Asp Gln Glu Val Arg Phe Pro Arg His Ala Arg
 65                  70                  75                  80

CGG CTG GCC ACC GGT TAC GGG TCG CTG GAC GGG GCG GCG CTG GCG GAT       288
Arg Leu Ala Thr Gly Tyr Gly Ser Leu Asp Gly Ala Ala Leu Ala Asp
                 85                  90                  95

GCG GTG GTC CGG TCG GGC GCC GAG ATC CGC TGG GAC AGC GAC ATC GCC       336
Ala Val Val Arg Ser Gly Ala Glu Ile Arg Trp Asp Ser Asp Ile Ala
            100                 105                 110

CTG CTG GAT GCG CAG GGG GCG ACG CTG TCC TGC GGC ACC CGG ATC GAG       384
Leu Leu Asp Ala Gln Gly Ala Thr Leu Ser Cys Gly Thr Arg Ile Glu
        115                 120                 125

GCG GGC GCG GTC CTG GAC GGG CGG GGC GCG CAG CCG TCG CGG CAT CTG       432
Ala Gly Ala Val Leu Asp Gly Arg Gly Ala Gln Pro Ser Arg His Leu
    130                 135                 140

ACC GTG GGT TTC CAG AAA TTC GTG GGT GTC GAG ATC GAG ACC GAC CGC       480
Thr Val Gly Phe Gln Lys Phe Val Gly Val Glu Ile Glu Thr Asp Arg
145                 150                 155                 160

CCC CAC GGC GTG CCC CGC CCG ATG ATC ATG GAC GCG ACC GTC ACC CAG       528
Pro His Gly Val Pro Arg Pro Met Ile Met Asp Ala Thr Val Thr Gln
                165                 170                 175

CAG GAC GGG TAC CGC TTC ATC TAT CTG CTG CCC TTC TCT CCG ACG CGC       576
Gln Asp Gly Tyr Arg Phe Ile Tyr Leu Leu Pro Phe Ser Pro Thr Arg
            180                 185                 190

ATC CTG ATC GAG GAC ACG CGC TAT TCC GAT GGC GGC GAT CTG GAC GAC       624
Ile Leu Ile Glu Asp Thr Arg Tyr Ser Asp Gly Gly Asp Leu Asp Asp
        195                 200                 205

GAC GCG CTG GCG GCG GCG TCC CAC GAC TAT GCC CGC CAG CAG GGC TGG       672
Asp Ala Leu Ala Ala Ala Ser His Asp Tyr Ala Arg Gln Gln Gly Trp
    210                 215                 220

ACC GGG GCC GAG GTC CGG CGC GAA CGC GGC ATC CTT CCC ATC GCG CTG       720
Thr Gly Ala Glu Val Arg Arg Glu Arg Gly Ile Leu Pro Ile Ala Leu
225                 230                 235                 240
```

```
GCC CAT GAT GCG GCG GGC TTC TGG GCC GAT CAC GCG GCG GGG CCT GTT        768
Ala His Asp Ala Ala Gly Phe Trp Ala Asp His Ala Ala Gly Pro Val
        245                 250                 255

CCC GTG GGA CTG CGC GCG GGG TTC TTT CAT CCG GTC ACC GGC TAT TCG        816
Pro Val Gly Leu Arg Ala Gly Phe Phe His Pro Val Thr Gly Tyr Ser
        260                 265                 270

CTG CCC TAT GCG GCA CAG GTG GCG GAC GTG GTG GCG GGT CTG TCC GGG        864
Leu Pro Tyr Ala Ala Gln Val Ala Asp Val Val Ala Gly Leu Ser Gly
        275                 280                 285

CCG CCC GGC ACC GAC GCG CTG CGC GGC GCC ATC CGC GAT TAC GCG ATC        912
Pro Pro Gly Thr Asp Ala Leu Arg Gly Ala Ile Arg Asp Tyr Ala Ile
        290                 295                 300

GAC CGG GCG CGC CGC GAC CGC TTT CTG CGC CTT TTG AAC CGG ATG CTG        960
Asp Arg Ala Arg Arg Asp Arg Phe Leu Arg Leu Leu Asn Arg Met Leu
305                 310                 315                 320

TTC CGC GGC TGC GCG CCC GAC CGG CGC TAT ACC CTG CTG CAG CGG TTC       1008
Phe Arg Gly Cys Ala Pro Asp Arg Arg Tyr Thr Leu Leu Gln Arg Phe
                325                 330                 335

TAC CGC ATG CCG CAT GGA CTG ATC GAA CGG TTC TAT GCC GGC CGG CTG       1056
Tyr Arg Met Pro His Gly Leu Ile Glu Arg Phe Tyr Ala Gly Arg Leu
                340                 345                 350

AGC GTG GCG GAT CAG CTG CGC ATC GTG ACC GGC AAG CCT CCC ATT CCC       1104
Ser Val Ala Asp Gln Leu Arg Ile Val Thr Gly Lys Pro Pro Ile Pro
        355                 360                 365

CTT GGC ACG GCC ATC CGC TGC CTG CCC GAA CGT CCC CTG CTG AAG GAA       1152
Leu Gly Thr Ala Ile Arg Cys Leu Pro Glu Arg Pro Leu Leu Lys Glu
370                 375                 380

AAC GCA TGA                                                           1161
Asn Ala
385
```

(2) INFORMATION FOR SEQ ID NO:6:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:6:

```
Val Thr His Asp Val Leu Leu Ala Gly Ala Gly Leu Ala Asn Gly Leu
1               5                   10                  15

Ile Ala Leu Ala Leu Arg Ala Ala Arg Pro Asp Leu Arg Val Leu Leu
                20                  25                  30

Leu Asp His Ala Ala Gly Pro Ser Asp Gly His Thr Trp Ser Cys His
            35                  40                  45

Asp Pro Asp Leu Ser Pro Asp Trp Leu Ala Arg Leu Lys Pro Leu Arg
        50                  55                  60

Arg Ala Asn Trp Pro Asp Gln Glu Val Arg Phe Pro Arg His Ala Arg
65                  70                  75                  80

Arg Leu Ala Thr Gly Tyr Gly Ser Leu Asp Gly Ala Leu Ala Asp
                85                  90                  95

Ala Val Val Arg Ser Gly Ala Glu Ile Arg Trp Asp Ser Asp Ile Ala
                100                 105                 110

Leu Leu Asp Ala Gln Gly Ala Thr Leu Ser Cys Gly Thr Arg Ile Glu
            115                 120                 125

Ala Gly Ala Val Leu Asp Gly Arg Gly Ala Gln Pro Ser Arg His Leu
        130                 135                 140
```

```
Thr Val Gly Phe Gln Lys Phe Val Gly Val Glu Ile Glu Thr Asp Arg
145                 150                 155                 160

Pro His Gly Val Pro Arg Pro Met Ile Met Asp Ala Thr Val Thr Gln
                165                 170                 175

Gln Asp Gly Tyr Arg Phe Ile Tyr Leu Leu Pro Phe Ser Pro Thr Arg
            180                 185                 190

Ile Leu Ile Glu Asp Thr Arg Tyr Ser Asp Gly Gly Asp Leu Asp Asp
        195                 200                 205

Asp Ala Leu Ala Ala Ala Ser His Asp Tyr Ala Arg Gln Gln Gly Trp
    210                 215                 220

Thr Gly Ala Glu Val Arg Arg Glu Arg Gly Ile Leu Pro Ile Ala Leu
225                 230                 235                 240

Ala His Asp Ala Ala Gly Phe Trp Ala Asp His Ala Ala Gly Pro Val
                245                 250                 255

Pro Val Gly Leu Arg Ala Gly Phe Phe His Pro Val Thr Gly Tyr Ser
                260                 265                 270

Leu Pro Tyr Ala Ala Gln Val Ala Asp Val Val Ala Gly Leu Ser Gly
            275                 280                 285

Pro Pro Gly Thr Asp Ala Leu Arg Gly Ala Ile Arg Asp Tyr Ala Ile
        290                 295                 300

Asp Arg Ala Arg Arg Asp Arg Phe Leu Arg Leu Leu Asn Arg Met Leu
305                 310                 315                 320

Phe Arg Gly Cys Ala Pro Asp Arg Arg Tyr Thr Leu Leu Gln Arg Phe
                325                 330                 335

Tyr Arg Met Pro His Gly Leu Ile Glu Arg Phe Tyr Ala Gly Arg Leu
                340                 345                 350

Ser Val Ala Asp Gln Leu Arg Ile Val Thr Gly Lys Pro Pro Ile Pro
            355                 360                 365

Leu Gly Thr Ala Ile Arg Cys Leu Pro Glu Arg Pro Leu Leu Lys Glu
        370                 375                 380

Asn Ala
385

(2) INFORMATION FOR SEQ ID NO:7:

(i) SEQUENCE CHARACTERISTICS:
        (A) LENGTH: 2886 base pairs
        (B) TYPE: nucleic acid
        (C) STRANDEDNESS: double
        (D) TOPOLOGY: linear (xi) SEQUENCE DESCRIPTION: SEQ ID NO:7:

GGATCCGGCG ACCTTGCGGC GCTGCGCCGC GCGCCTTTGC TGGTGCCTGG GCCGGGTGGC      60

CAATGGTCGC AAGCAACGGG GATGGAAACC GGCGATGCGG GACTGTAGTC TGCGCGGATC     120

GCCGGTCCGG GGGACAAGAT GAGCGCACAT GCCCTGCCCA AGGCAGATCT GACCGCCACC     180

AGCCTGATCG TCTCGGGCGG CATCATCGCC GCTTGGCTGG CCCTGCATGT GCATGCGCTG     240

TGGTTTCTGG ACGCAGCGGC GCATCCCATC CTGGCGATCG CAAATTTCCT GGGGCTGACC     300

TGGCTGTCGG TCGGATTGTT CATCATCGCG CATGACGCGA TGCACGGGTC GGTGGTGCCG     360

GGGCGTCCGC GCGCCAATGC GGCGATGGGC CAGCTTGTCC TGTGGCTGTA TGCCGGATTT     420

TCGTGGCGCA AGATGATCGT CAAGCACATG GCCCATCACC GCCATGCCGG AACCGACGAC     480

GACCCCGATT TCGACCATGG CGGCCCGGTC CGCTGGTACG CCCGCTTCAT CGGCACCTAT     540

TTCGGCTGGC GCGAGGGGCT GCTGCTGCCC GTCATCGTGA CGGTCTATGC GCTGATCCTT     600

GGGGATCGCT GGATGTACGT GGTCTTCTGG CCGCTGCCGT CGATCCTGGC GTCGATCCAG     660
```

```
CTGTTCGTGT TCGGCACCTG GCTGCCGCAC CGCCCCGGCC ACGACGCGTT CCCGGACCGC    720

CACAATGCGC GGTCGTCGCG GATCAGCGAC CCCGTGTCGC TGCTGACCTG CTTTCACTTT    780

GGCGGTTATC ATCACGAACA CCACCTGCAC CCGACGGTGC CGTGGTGGCG CCTGCCCAGC    840

ACCCGCACCA AGGGGACAC CGCATGACCA ATTTCCTGAT CGTCGTCGCC ACCGTGCTGG     900

TGATGGAGTT GACGGCCTAT TCCGTCCACC GCTGGATCAT GCACGGCCCC CTGGGCTGGG    960

GCTGGCACAA GTCCCACCAC GAGGAACACG ACCACGCGCT GGAAAAGAAC GACCTGTACG   1020

GCCTGGTCTT TGCGGTGATC GCCACGGTGC TGTTCACGGT GGGCTGGATC TGGGCGCCGG   1080

TCCTGTGGTG GATCGCCTTG GGCATGACTG TCTATGGGCT GATCTATTTC GTCCTGCATG   1140

ACGGGCTGGT GCATCAGCGC TGGCCGTTCC GTTATATCCC GCGCAAGGGC TATGCCAGAC   1200

GCCTGTATCA GGCCCACCGC CTGCACCATG CGGTCGAGGG GCGCGACCAT TGCGTCAGCT   1260

TCGGCTTCAT CTATGCGCCC CCGGTCGACA AGCTGAAGCA GGACCTGAAG ATGTCGGGCG   1320

TGCTGCGGGC CGAGGCGCAG GAGCGCACGT GACCCATGAC GTGCTGCTGG CAGGGGCGGG   1380

CCTTGCCAAC GGGCTGATCG CCCTGGCGCT GCGCGCGGCG CGGCCCGACC TGCGCGTGCT   1440

GCTGCTGGAC CATGCCGCAG GACCGTCAGA CGGCCACACC TGGTCCTGCC ACGACCCCGA   1500

CCTGTCGCCG GACTGGCTGG CGCGGCTGAA GCCCCTGCGC CGCGCCAACT GGCCCGACCA   1560

GGAGGTGCGC TTTCCCCGCC ATGCCCGGCG GCTGGCCACC GGTTACGGGT CGCTGGACGG   1620

GGCGGCGCTG GCGGATGCGG TGGTCCGGTC GGGCGCCGAG ATCCGCTGGG ACAGCGACAT   1680

CGCCCTGCTG GATGCGCAGG GGGCGACGCT GTCCTGCGGC ACCCGGATCG AGGCGGGCGC   1740

GGTCCTGGAC GGGCGGGGCG CGCAGCCGTC GCGGCATCTG ACCGTGGGTT TCCAGAAATT   1800

CGTGGGTGTC GAGATCGAGA CCGACCGCCC CCACGGCGTG CCCCGCCCGA TGATCATGGA   1860

CGCGACCGTC ACCCAGCAGG ACGGGTACCG CTTCATCTAT CTGCTGCCCT TCTCTCCGAC   1920

GCGCATCCTG ATCGAGGACA CGCGCTATTC CGATGGCGGC GATCTGGACG ACGACGCGCT   1980

GGCGGCGGCG TCCCACGACT ATGCCCGCCA GCAGGGCTGG ACCGGGGCCG AGGTCCGGCG   2040

CGAACGCGGC ATCCTTCCCA TCGCGCTGGC CCATGATGCG GCGGGCTTCT GGGCCGATCA   2100

CGCGGCGGGG CCTGTTCCCG TGGGACTGCG CGCGGGGTTC TTTCATCCGG TCACCGGCTA   2160

TTCGCTGCCC TATGCGGCAC AGGTGGCGGA CGTGGTGGCG GGTCTGTCCG GGCCGCCCGG   2220

CACCGACGCG CTGCGCGGCG CCATCCGCGA TTACGCGATC GACCGGGCGC GCCGCGACCG   2280

CTTTCTGCGC CTTTTGAACC GGATGCTGTT CCGCGGCTGC GCGCCCGACC GGCGCTATAC   2340

CCTGCTGCAG CGGTTCTACC GCATGCCGCA TGGACTGATC GAACGGTTCT ATGCCGGCCG   2400

GCTGAGCGTG GCGGATCAGC TGCGCATCGT GACCGGCAAG CCTCCCATTC CCCTTGGCAC   2460

GGCCATCCGC TGCCTGCCCG AACGTCCCCT GCTGAAGGAA AACGCATGAA CGCCCATTCG   2520

CCCGCGGCCA AGACCGCCAT CGTGATCGGC GCAGGCTTTG GCGGGCTGGC CCTGGCCATC   2580

CGCCTGCAGT CCGCGGGCAT CGCCACCACC CTGGTCGAGG CCCGGGACAA GCCCGGCGGG   2640

CGCGCCTATG TCTGGCACGA TCAGGGCCAT CTCTTCGACG CGGGCCCGAC CGTCATCACC   2700

GACCCCGATG CGCTGAAAGA GCTGTGGGCC CTGACCGGGC AGGACATGGC GCGCGACGTG   2760

ACGCTGATGC CGGTCTCGCC CTTCTATCGG CTGATGTGGC CGGGCGGGAA GGTCTTCGAT   2820

TACGTGAACG AGGCCGATCC AGGGTCTGGG TCTTGCCGTG CCAGGTGAAG CTGTTGCCGT   2880

GGATCC                                                              2886
```

(2) INFORMATION FOR SEQ ID NO:8:

```
     (i) SEQUENCE CHARACTERISTICS:
         (A) LENGTH: 729 base pairs
         (B) TYPE: nucleic acid
         (C) STRANDEDNESS: double
         (D) TOPOLOGY: linear (ix) FEATURE:
         (A) NAME/KEY: CDS
         (B) LOCATION: 1..726

(ix) FEATURE:
         (A) NAME/KEY: mat_peptide
         (B) LOCATION: 1..726

(xi) SEQUENCE DESCRIPTION: SEQ ID NO:8:

ATG TCC GGA CGG AAG CCT GGC ACA ACT GGC GAC ACG ATC GTC AAT CTC        48
Met Ser Gly Arg Lys Pro Gly Thr Thr Gly Asp Thr Ile Val Asn Leu
 1               5                  10                  15

GGT CTG ACC GCC GCG ATC CTG CTG TGC TGG CTG GTC CTG CAC GCC TTT        96
Gly Leu Thr Ala Ala Ile Leu Leu Cys Trp Leu Val Leu His Ala Phe
             20                  25                  30

ACG CTA TGG TTG CTA GAT GCG GCC GCG CAT CCG CTG CTT GCC GTG CTG       144
Thr Leu Trp Leu Leu Asp Ala Ala Ala His Pro Leu Leu Ala Val Leu
         35                  40                  45

TGC CTG GCT GGG CTG ACC TGG CTG TCG GTC GGG CTG TTC ATC ATC GCG       192
Cys Leu Ala Gly Leu Thr Trp Leu Ser Val Gly Leu Phe Ile Ile Ala
 50                  55                  60

CAT GAC GCA ATG CAC GGG TCC GTG GTG CCG GGG CGG CCG CGC GCC AAT       240
His Asp Ala Met His Gly Ser Val Val Pro Gly Arg Pro Arg Ala Asn
 65                  70                  75                  80

GCG GCG ATC GGG CAA CTG GCG CTG TGG CTC TAT GCG GGG TTC TCG TGG       288
Ala Ala Ile Gly Gln Leu Ala Leu Trp Leu Tyr Ala Gly Phe Ser Trp
             85                  90                  95

CCC AAG CTG ATC GCC AAG CAC ATG ACG CAT CAC CGG CAC GCC GGC ACC       336
Pro Lys Leu Ile Ala Lys His Met Thr His His Arg His Ala Gly Thr
            100                 105                 110

GAC AAC GAT CCC GAT TTC GGT CAC GGA GGG CCC GTG CGC TGG TAC GGC       384
Asp Asn Asp Pro Asp Phe Gly His Gly Gly Pro Val Arg Trp Tyr Gly
        115                 120                 125

AGC TTC GTC TCC ACC TAT TTC GGC TGG CGA GAG GGA CTG CTG CTA CCG       432
Ser Phe Val Ser Thr Tyr Phe Gly Trp Arg Glu Gly Leu Leu Leu Pro
    130                 135                 140

GTG ATC GTC ACC ACC TAT GCG CTG ATC CTG GGC GAT CGC TGG ATG TAT       480
Val Ile Val Thr Thr Tyr Ala Leu Ile Leu Gly Asp Arg Trp Met Tyr
145                 150                 155                 160

GTC ATC TTC TGG CCG GTC CCG GCC GTT CTG GCG TCG ATC CAG ATT TTC       528
Val Ile Phe Trp Pro Val Pro Ala Val Leu Ala Ser Ile Gln Ile Phe
                165                 170                 175

GTC TTC GGA ACT TGG CTG CCC CAC CGC CCG GGA CAT GAC GAT TTT CCC       576
Val Phe Gly Thr Trp Leu Pro His Arg Pro Gly His Asp Asp Phe Pro
            180                 185                 190

GAC CGG CAC AAC GCG AGG TCG ACC GGC ATC GGC GAC CCG TTG TCA CTA       624
Asp Arg His Asn Ala Arg Ser Thr Gly Ile Gly Asp Pro Leu Ser Leu
        195                 200                 205

CTG ACC TGC TTC CAT TTC GGC GGC TAT CAC CAC GAA CAT CAC CTG CAT       672
Leu Thr Cys Phe His Phe Gly Gly Tyr His His Glu His His Leu His
    210                 215                 220

CCG CAT GTG CCG TGG TGG CGC CTG CCT CGT ACA CGC AAG ACC GGA GGC       720
Pro His Val Pro Trp Trp Arg Leu Pro Arg Thr Arg Lys Thr Gly Gly
225                 230                 235                 240

CGC GCA TGA                                                           729
Arg Ala
```

(2) INFORMATION FOR SEQ ID NO:9:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:9:

```
Met Ser Gly Arg Lys Pro Gly Thr Thr Gly Asp Thr Ile Val Asn Leu
 1               5                  10                  15

Gly Leu Thr Ala Ala Ile Leu Leu Cys Trp Leu Val Leu His Ala Phe
             20                  25                  30

Thr Leu Trp Leu Leu Asp Ala Ala His Pro Leu Leu Ala Val Leu
         35                  40                  45

Cys Leu Ala Gly Leu Thr Trp Leu Ser Val Gly Leu Phe Ile Ile Ala
     50                  55                  60

His Asp Ala Met His Gly Ser Val Val Pro Gly Arg Pro Arg Ala Asn
 65                  70                  75                  80

Ala Ala Ile Gly Gln Leu Ala Leu Trp Leu Tyr Ala Gly Phe Ser Trp
                 85                  90                  95

Pro Lys Leu Ile Ala Lys His Met Thr His His Arg His Ala Gly Thr
            100                 105                 110

Asp Asn Asp Pro Asp Phe Gly His Gly Gly Pro Val Arg Trp Tyr Gly
            115                 120                 125

Ser Phe Val Ser Thr Tyr Phe Gly Trp Arg Glu Gly Leu Leu Leu Pro
    130                 135                 140

Val Ile Val Thr Thr Tyr Ala Leu Ile Leu Gly Asp Arg Trp Met Tyr
145                 150                 155                 160

Val Ile Phe Trp Pro Val Pro Ala Val Leu Ala Ser Ile Gln Ile Phe
                165                 170                 175

Val Phe Gly Thr Trp Leu Pro His Arg Pro Gly His Asp Asp Phe Pro
            180                 185                 190

Asp Arg His Asn Ala Arg Ser Thr Gly Ile Gly Asp Pro Leu Ser Leu
            195                 200                 205

Leu Thr Cys Phe His Phe Gly Gly Tyr His His Glu His His Leu His
    210                 215                 220

Pro His Val Pro Trp Trp Arg Leu Pro Arg Thr Arg Lys Thr Gly Gly
225                 230                 235                 240

Arg Ala
```

(2) INFORMATION FOR SEQ ID NO:10:

(i) SEQUENCE CHARACTERISTICS:
        (A) LENGTH: 489 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..486

(ix) FEATURE:
        (A) NAME/KEY: mat_peptide
        (B) LOCATION: 1..486

(xi) SEQUENCE DESCRIPTION: SEQ ID NO:10:

```
ATG ACG CAA TTC CTC ATT GTC GTG GCG ACA GTC CTC GTG ATG GAG CTG      48
Met Thr Gln Phe Leu Ile Val Val Ala Thr Val Leu Val Met Glu Leu
 1               5                  10                  15
```

```
ACC GCC TAT TCC GTC CAC CGC TGG ATT ATG CAC GGC CCC CTA GGC TGG        96
Thr Ala Tyr Ser Val His Arg Trp Ile Met His Gly Pro Leu Gly Trp
            20                  25                  30

GGC TGG CAC AAG TCC CAT CAC GAA GAG CAC GAC CAC GCG TTG GAG AAG       144
Gly Trp His Lys Ser His His Glu Glu His Asp His Ala Leu Glu Lys
        35                  40                  45

AAC GAC CTC TAC GGC GTC GTC TTC GCG GTG CTG GCG ACG ATC CTC TTC       192
Asn Asp Leu Tyr Gly Val Val Phe Ala Val Leu Ala Thr Ile Leu Phe
    50                  55                  60

ACC GTG GGC GCC TAT TGG TGG CCG GTG CTG TGG TGG ATC GCC CTG GGC       240
Thr Val Gly Ala Tyr Trp Trp Pro Val Leu Trp Trp Ile Ala Leu Gly
65                  70                  75                  80

ATG ACG GTC TAT GGG TTG ATC TAT TTC ATC CTG CAC GAC GGG CTT GTG       288
Met Thr Val Tyr Gly Leu Ile Tyr Phe Ile Leu His Asp Gly Leu Val
                85                  90                  95

CAT CAA CGC TGG CCG TTT CGG TAT ATT CCG CGG CGG GGC TAT TTC CGC       336
His Gln Arg Trp Pro Phe Arg Tyr Ile Pro Arg Arg Gly Tyr Phe Arg
            100                 105                 110

AGG CTC TAC CAA GCT CAT CGC CTG CAC CAC GCG GTC GAG GGG CGG GAC       384
Arg Leu Tyr Gln Ala His Arg Leu His His Ala Val Glu Gly Arg Asp
        115                 120                 125

CAC TGC GTC AGC TTC GGC TTC ATC TAT GCC CCA CCC GTG GAC AAG CTG       432
His Cys Val Ser Phe Gly Phe Ile Tyr Ala Pro Pro Val Asp Lys Leu
    130                 135                 140

AAG CAG GAT CTG AAG CGG TCG GGT GTC CTG CGC CCC CAG GAC GAG CGT       480
Lys Gln Asp Leu Lys Arg Ser Gly Val Leu Arg Pro Gln Asp Glu Arg
145                 150                 155                 160

CCG TCG TGA                                                           489
Pro Ser
```

(2) INFORMATION FOR SEQ ID NO:11:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:11:

```
Met Thr Gln Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Val Val Phe Ala Val Leu Ala Thr Ile Leu Phe
    50                  55                  60

Thr Val Gly Ala Tyr Trp Trp Pro Val Leu Trp Trp Ile Ala Leu Gly
65                  70                  75                  80

Met Thr Val Tyr Gly Leu Ile Tyr Phe Ile Leu His Asp Gly Leu Val
                85                  90                  95

His Gln Arg Trp Pro Phe Arg Tyr Ile Pro Arg Arg Gly Tyr Phe Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Arg Ser Gly Val Leu Arg Pro Gln Asp Glu Arg
```

145 150 155 160

Pro Ser (2) INFORMATION FOR SEQ ID NO:12:

(i) SEQUENCE CHARACTERISTICS:
       (A) LENGTH: 1631 base pairs
       (B) TYPE: nucleic acid
       (C) STRANDEDNESS: double
       (D) TOPOLOGY: linear (xi) SEQUENCE DESCRIPTION: SEQ ID NO:12:

| | | | | | |
|---|---|---|---|---|---|
| CTGCAGGCCG | GGCCCGGTGG | CCAATGGTCG | CAACCGGCAG | GACTGGAACA | GGACGGCGGG | 60 |
| CCGGTCTAGG | CTGTCGCCCT | ACGCAGCAGG | AGTTTCGGAT | GTCCGGACGG | AAGCCTGGCA | 120 |
| CAACTGGCGA | CACGATCGTC | AATCTCGGTC | TGACCGCCGC | GATCCTGCTG | TGCTGGCTGG | 180 |
| TCCTGCACGC | CTTTACGCTA | TGGTTGCTAG | ATGCGGCCGC | GCATCCGCTG | CTTGCCGTGC | 240 |
| TGTGCCTGGC | TGGGCTGACC | TGGCTGTCGG | TCGGGCTGTT | CATCATCGCG | CATGACGCAA | 300 |
| TGCACGGGTC | CGTGGTGCCG | GGGCGGCCGC | GCGCCAATGC | GGCGATCGGG | CAACTGGCGC | 360 |
| TGTGGCTCTA | TGCGGGGTTC | TCGTGGCCCA | AGCTGATCGC | CAAGCACATG | ACGCATCACC | 420 |
| GGCACGCCGG | CACCGACAAC | GATCCCGATT | TCGGTCACGG | AGGGCCCGTG | CGCTGGTACG | 480 |
| GCAGCTTCGT | CTCCACCTAT | TTCGGCTGGC | GAGAGGGACT | GCTGCTACCG | GTGATCGTCA | 540 |
| CCACCTATGC | GCTGATCCTG | GGCGATCGCT | GGATGTATGT | CATCTTCTGG | CCGGTCCCGG | 600 |
| CCGTTCTGGC | GTCGATCCAG | ATTTTCGTCT | TCGGAACTTG | GCTGCCCCAC | CGCCCGGGAC | 660 |
| ATGACGATTT | TCCCGACCGG | CACAACGCGA | GGTCGACCGG | CATCGGCGAC | CCGTTGTCAC | 720 |
| TACTGACCTG | CTTCCATTTC | GGCGGCTATC | ACCACGAACA | TCACCTGCAT | CCGCATGTGC | 780 |
| CGTGGTGGCG | CCTGCCTCGT | ACACGCAAGA | CCGGAGGCCG | CGCATGACGC | AATTCCTCAT | 840 |
| TGTCGTGGCG | ACAGTCCTCG | TGATGGAGCT | GACCGCCTAT | TCCGTCCACC | GCTGGATTAT | 900 |
| GCACGGCCCC | CTAGGCTGGG | GCTGGCACAA | GTCCCATCAC | GAAGAGCACG | ACCACGCGTT | 960 |
| GGAGAAGAAC | GACCTCTACG | GCGTCGTCTT | CGCGGTGCTG | GCGACGATCC | TCTTCACCGT | 1020 |
| GGGCGCCTAT | TGGTGGCCGG | TGCTGTGGTG | GATCGCCCTG | GGCATGACGG | TCTATGGGTT | 1080 |
| GATCTATTTC | ATCCTGCACG | ACGGGCTTGT | GCATCAACGC | TGGCCGTTTC | GGTATATTCC | 1140 |
| GCGGCGGGGC | TATTTCCGCA | GGCTCTACCA | AGCTCATCGC | CTGCACCACG | CGGTCGAGGG | 1200 |
| GCGGGACCAC | TGCGTCAGCT | TCGGCTTCAT | CTATGCCCCA | CCCGTGGACA | AGCTGAAGCA | 1260 |
| GGATCTGAAG | CGGTCGGGTG | TCCTGCGCCC | CCAGGACGAG | CGTCCGTCGT | GATCTCTGAT | 1320 |
| CCCGGCGTGG | CCGCATGAAA | TCCGACGTGC | TGCTGGCAGG | GGCCGGCCTT | GCCAACGGAC | 1380 |
| TGATCGCGCT | GGCGATCCGC | AAGGCGCGGC | CCGACCTTCG | CGTGCTGCTG | CTGGACCGTG | 1440 |
| CGGCGGGCGC | CTCGGACGGG | CATACTTGGT | CCTGCCACGA | CACCGATTTG | GCGCCGCACT | 1500 |
| GGCTGGACCG | CCTGAAGCCG | ATCAGGCGTG | GCGACTGGCC | CGATCAGGAG | GTGCGGTTCC | 1560 |
| CAGACCATTC | GCGAAGGCTC | CGGGCCGGAT | ATGGCTCGAT | CGACGGGCGG | GGGCTGATGC | 1620 |
| GTGCGGTGAC | C | | | | | 1631 |

DNA STRANDS USEFUL FOR THE SYNTHESIS OF XANTHOPHYLLS AND THE PROCESS FOR PRODUCING THE XANTHOPHYLLS

This application is a divisional of application Ser. No. 08/663,610, filed Sep. 23, 1996 which is national stage of PCT/JP94/02220 filed Dec. 26, 1994, now U.S. Pat. No. 5,811,273.

TECHNICAL FIELD

The present invention relates to DNA strands useful for the synthesis of keto group-containing xanthophylls (ketocarotenoids) such as astaxanthin which are useful for heightening the color of cultured fishes and shellfishes such as sea breams, salmons, lobster and the like and is used for foods as a coloring agent and an antioxidant, and to a process for producing keto group-containing xanthophylls (ketocarotinoids) such as astaxanthin with use of a microorganism into which the DNA strands have been introduced.

BACKGROUND ART

The term xanthophylls means carotenoid pigments having an oxygen-containing group such as a hydroxyl group, a keto group or an epoxy group. Carotenoids are synthesized by the isoprenoid biosynthetic process which is used in common halfway with steroids and other terpenoids with mevalonic acid as a starting material. C15 farnesyl pyrophosphate (FPP) resulting from isoprene basic biosynthetic pathway is condensed with C5 isopentenyl pyrophosphate (IPP) to give C20 geranylgeranyl pyrophosphate (GGPP). Two molecules of GGPP are condensed to synthesize a colorless phytoene as an initial carotenoid. The phytoene is converted into phytofluene, $\zeta$-carotene, neurosporene and then lycopene by a series of desaturation reactions, and lycopene is in turn converted into $\beta$-carotene by the cyclization reaction. It is believed that a variety of xanthophylls are synthesized by introducing a hydroxyl group or a keto group into the $\beta$-carotene (See Britton, G., "Biosynthesis of Carotenoids"; Plant Pigments, Goodwin, T. W. ed., London, Academic Press, 1988, pp. 133–182).

The present inventors have recently made it possible to clone a carotenoid biosynthesis gene cluster from a epiphytic non-photosynthetic bacterium *Erwinia uredovora* in *Escherichia coli* with an index of the yellow tone of the bacterium, a variety of combinations of the genes being expressed in microorganisms such as *Escherichia coli* to produce phytoene, lycopene, $\beta$-carotene, and zeaxanthin which is a derivative of $\beta$-carotene into which hydroxyl groups have been introduced (See FIG. 10; Misawa, N., Nakagawa, M., Kobayashi, K., Yamano, S., Izawa, Y., Nakamura, L., Harashima, K.; "Elucidation of the *Erwinia uredovora* Carotenoid biosynthetic Pathway by Functional Analysis of Gene Products Expressed in *Escherichia coli*", J. Bacteriol., 172, p. 6704–6712, 1990; Misawa, N., Yamano, S., Ikenaga, H., "Production of $\beta$-carotene in *Zymomonas mobilis* and *Agrobacterium tumefaciencs* by Introduction of the Biosynthesis Genes from *Erwinia uredovora*", Appl. environ. Microbiol., 57, p. 1847–1849, 1991; and Japanese Patent Application No. 58786/1991 (Japanese Patent Application No. 53255/1990): "DNA Strands useful for the Synthesis of Carotenoids").

On the other hand, astaxanthin, a red xanthophyll, is a typical animal carotenoid which occurs particularly in a wide variety of marine animals including red fishes such as a sea bream and a salmon, and crustaceans such as a crab and a lobster. In general, animals cannot biosynthesize carotenoids, so that it is necessary for them to ingest carotenoids synthesized by microorganisms or plants from their environments. Thus, astaxanthin hitherto has been used widely for strengthening the color of cultured fishes and shellfishes such as sea bream, salmon, lobster and the like. Moreover, astaxanthin has attracted attention not only as a coloring matter in foods but also as an anti-oxidant for removing active oxygen generated in bodies, which causes carcinoma (see Takao Matsuno ed., "Physiological Functions and Bioactivities of Carotenoids in Animals", Kagaku to Seibutsu, 28, p. 219–227, 1990). As the sources of astaxanthin, there have been known crustaceans such as a krill in the Antarctic Ocean, cultured products of yeast Phaffia, cultured products of a green alga Haematococcus, and products obtained by the organic synthetic methods. However, when crustaceans such as krill in the Antarctic Ocean or the like are used laborious work and much expense is required for the isolation of astaxantin from contaminants such as lipids and the like during harvesting and extraction of the krill. Moreover, in the case of the cultured products from the yeast Phaffia, a great deal of expense is incurred for the gathering and extraction of astaxantin, because yeast has rigid cell walls and produces astaxanthin in a low yield. Also, in the case of the cultured product of the green alga Haematococcus, not only a location for collecting sunlight or an investment of a culturing apparatus for supplying an artificial light is required in order to supply light which is essential to the synthesis of astaxantin, but also it is difficult to separate astaxantin from fatty acid esters as by-products or chlorophylls present in the cultured products. For these reasons, astaxanthin produced from biological sources presently is inferior to that obtained by organic synthetic methods on the basis of cost. The organic synthetic methods however, produce by-products. Thus, in context of its use as a feed for fishes and shellfishes and an additive to foods, the products obtained by these organic synthetic methods are unacceptable due to the consumer's preference for natural products. Accordingly, it is desired to supply an inexpensive astaxanthin that is safe and produced from biological sources and thus presents a good image to consumers, and to develop a process for producing astaxanthin.

DISCLOSURE OF THE INVENTION

It would be very useful to find the genes that play a role in the biosynthesis of astaxanthin, because this advance would allow astaxanthin production from microorganisms to optimize safety for a food and also allow astaxanthin, regardless of the presence of astaxanthin-producing ability of a microorganism, by introducing a gene cluster for astaxanthin biosynthesis into the microorganism. No problem of by-products as contaminants is incurred in this case. Thus, it would be not difficult to increase the production amount of astaxanthin with a recent advanced technique of gene manipulation to a level higher than that accomplished by the organic synthetic methods. However, the groups of genes for synthesizing zeaxanthin, one of the xanthophylls, have already been acquired by the present inventors as described above, while no genes encoding a keto group-introducing enzyme required for the synthesis of astaxanthin have not successfully obtained. The reason for failure in obtaining the genes includes that the keto group-introducing enzyme is a membrane protein and loses its activity when isolated from the membrane, so that it was impossible to purify the enzyme or measure its activity and no information on the enzyme has been obtained. Thus, it has hitherto been impossible to produce astaxanthin in microorganisms by gene manipulation.

The object of the present invention is to provide DNA strands which contain genes required for producing keto group-containing xanthophylls (ketocarotenoids) such as astaxanthin in microorganisms by obtaining such genes coding for enzymes such as a keto group-introducing enzyme required for producing keto group-containing xanthophylls (ketocarotenoids) such as astaxanthin, and to provide a process for producing keto group-containing xanthophylls (ketocarotenoids) such as astaxanthin with the microorganisms into which the DNA strands have been introduced.

The gene cloning method which is often used usually comprising purifying the desired protein, partially determining the amino acid sequence and obtaining genes by a synthetic probe. This however, cannot be used because of the purification of the astaxanthin synthetic enzyme being impossible, as described above. Thus, the present inventors have paid attention to the fact that the cluster of carotenoid synthesis genes in non-photosynthetic bacterium (Erwinia) functions in *Escherichia coli*, in which lycopene and β-carotene which are believed to be intermediates for bio-synthesis of astaxanthin, are allowed to produce with combinations of the genes from the gene cluster, and have used *Escherichia coli* as a host for cloning of astaxanthin synthetic genes. The present inventors also have paid attention to the fact that some marine bacteria have an astaxanthin-producing ability (Yokoyama, A., Izumida, H., Miki, W., "Marine bacteria produced astaxanthin", 10th International Symposium on Carotenoids, Abstract, CL11-3, 1993), that a series of related genes would constituted a cluster in the case of bacteria, and that the gene cluster would be expressed functionally in *Escherichia coli* in the case of bacteria. The present inventors have thus selected marine bacteria as gene sources. They have carried out research with a combination of these two means and successfully obtained the gene group which is required for the biosynthesis of astaxanthin and the other keto group-containing xanthophylls from marine bacteria. They have thus accomplished the present invention. In addition, it has been first elucidated in the present invention that the astaxanthin synthesis gene cluster in marine bacteria constitutes a cluster and expresses its function in *Escherichia coli,* and these gene products can utilize β-carotene or lycopene as a substrate.

The DNA strands according to the present invention are set forth as follows.

(1) A DNA strand having a nucleotide sequence which encodes a polypeptide having an enzyme activity for converting the methylene group at the 4-position of the β-ionone ring into a keto group.

(2) a DNA strand having a nucleotide sequence which encodes a polypeptide having an enzyme activity for converting the methylene group at the 4-position of the β-ionone ring into a keto group and having an amino acid sequence substantially of amino acid Nos. 1–212 which is shown in the SEQ ID NO:2.

(3) A DNA strand hybridizing the DNA strand described in (2) and having a nucleotide sequence which encodes a polypeptide having an enzyme activity described in (2).

(4) A DNA strand having a nucleotide sequence which encodes a polypeptide having an enzyme activity for converting the methylene group at the 4-position of the β-ionone ring into a keto group and having an amino acid sequence substantially of amino acid Nos. 1–242 which is shown in the SEQ ID NO:9.

(5) A DNA strand hybridizing the DNA strand described in (4) and having a nucleotide sequence which encodes a polypeptide having an enzyme activity described in (4).

(6) A DNA strand having a nucleotide sequence which encodes a polypeptide having an enzyme activity for converting β-carotene into canthaxanthin via echinenone and having an amino acid sequence substantially of amino acid Nos. 1–212 which is shown in the SEQ ID NO:2.

(7) A DNA strand hybridizing the DNA strand described in (6) and having a nucleotide sequence which encodes a polypeptide having an enzyme activity described in (6).

(8) A DNA strand having a nucleotide sequence which encodes a polypeptide having an enzyme activity for converting β-carotene into canthaxanthin via echinenone and having an amino acid sequence substantially of amino acid Nos. 1–242 which is shown in the SEQ ID NO:9.

(9) A DNA strand hybridizing the DNA strand described in (8) and having a nucleotide sequence which encodes a polypeptide having an enzyme activity described in (8).

(10) A DNA strand having a nucleotide sequence which encodes a polypeptide having an enzyme activity for converting the methylene group at the 4-position of the 3-hydroxy-β-ionone ring into a keto group.

(11) A DNA strand having a nucleotide sequence which encodes a polypeptide having an enzyme activity for converting the methylene group at the 4-position of the 3-hydroxy-β-ionone ring into a keto group and having an amino acid sequence substantially of amino acid Nos. 1–212 which is shown in the SEQ ID NO:2.

(12) A DNA strand hybridizing the DNA strand described in (11) and having a nucleotide sequence which encodes a polypeptide having an enzyme activity described in (11).

(13) A DNA strand having a nucleotide sequence which encodes a polypeptide having an enzyme activity for converting the methylene group at the 4-position of the 3-hydroxy-β-ionone ring into a keto group and having an amino acid sequence substantially of amino acid Nos. 1–242 which is shown in the SEQ ID NO:9.

(14) A DNA strand hybridizing the DNA strand described in (13) and having a nucleotide sequence which encodes a polypeptide having an enzyme activity described in (13).

(15) A DNA strand having a nucleotide sequence which encodes a polypeptide having an enzyme activity for converting zeaxanthin into astaxanthin by way of 4-ketozeaxanthin and having an amino acid sequence substantially of amino acid Nos. 1–212 which is shown in the SEQ ID NO:2.

(16) A DNA strand hybridizing the DNA strand described in (15) and having a nucleotide sequence which encodes a polypeptide having an enzyme activity described in (15).

(17) A DNA strand having a nucleotide sequence which encodes a polypeptide having an enzyme activity for converting zeaxanthin into astaxanthin by way of 4-ketozeaxanthin and having an amino acid sequence substantially of amino acid Nos. 1–242 which is shown in the SEQ ID NO:9.

(18) A DNA strand hybridizing the DNA strand described in (17) and having a nucleotide sequence which encodes a polypeptide having an enzyme activity described in (17).

(19) A DNA strand having a nucleotide sequence which encodes a polypeptide having an enzyme activity for adding a hydroxyl group to the 3-carbon of the 4-keto-β-ionone ring.

(20) A DNA strand having a nucleotide sequence which encodes a polypeptide having an enzyme activity for adding a hydroxyl group to position 3-carbon of the 4-keto-β-ionone ring and having an amino acid sequence substantially of amino acid Nos. 1–162 which is shown in the SEQ ID NO:4.

(21) A DNA strand hybridizing the DNA strand described in (20) and having a nucleotide sequence which encodes a polypeptide having an enzyme activity described in (20).

(22) A DNA strand having a nucleotide sequence which encodes a polypeptide having an enzyme activity for adding a hydroxyl group to position 3-carbon of the 4-keto-β-ionone ring and having an amino acid sequence substantially of amino acid Nos. 1–162 which is shown in the SEQ ID NO:11.

(23) A DNA strand hybridizing the DNA strand described in (22) and having a nucleotide sequence which encodes a polypeptide having an enzyme activity described in (22).

(24) A DNA strand having a nucleotide sequence which encodes a polypeptide having an enzyme activity for converting canthaxanthin into astaxanthin by way of phoenicoxanthin and having an amino acid sequence substantially of amino acid Nos. 1–162 which is shown in the SEQ ID NO:4.

(25) A DNA strand hybridizing the DNA strand described in (24) and having a nucleotide sequence which encodes a polypeptide having an enzyme activity described in (24).

(26) A DNA strand having a nucleotide sequence which encodes a polypeptide having an enzyme activity for converting canthaxanthin into astaxanthin by way of phoenicoxanthin and having an amino acid sequence substantially of amino acid Nos. 1–162 which is shown in the SEQ ID NO:11.

(27) A DNA strand hybridizing the DNA strand described in (26) and having a nucleotide sequence which encodes a polypeptide having an enzyme activity described in (26).

The present invention also relates to a process for producing xanthophylls.

That is, the process for producing xanthophylls according to the present invention is set forth below.

(1) A process for producing a xanthophyll comprising introducing the DNA strand described in any one of the above mentioned DNA strands (1)–(9) into a microorganism having a β-carotene-synthesizing ability, culturing the transformed microorganism in a culture medium, and obtaining canthaxanthin or echinenone from the cultured cells.

(2) A process for producing a xanthophyll comprising introducing the DNA strand described in any one of the above mentioned DNA strands (10)–(18) into a microorganism having a zeaxanthin-synthesizing ability, culturing the transformed microorganism in a culture medium, and obtaining astaxanthin or 4-ketozeaxanthin from the cultured cells.

(3) A process for producing a xanthophyll comprising introducing the DNA strand described in any one of the above mentioned DNA strands (19)–(27) into a microorganism having a canthaxanthin-synthesizing ability, culturing the transformed microorganism in a culture medium, and obtaining astaxanthin or phoenicoxanthin from the cultured cells.

(4) A process for producing a xanthophyll according to any one of the above mentioned processes (1)–(3), wherein the microorganism is a bacterium or yeast.

BRIEF DESCRIPTION OF THE DRAWINGS

FIG. 1 the nucleotide sequence of the keto group-introducing enzyme gene (crtW gene) of the marine bacterium *Agrobacterium aurantiacus* sp. nov. MK1 and the amino acid sequence of a polypeptide to be encoded thereby (SEQ ID NOS:1–2).

FIG. 2 the nucleotide sequence of the hydroxyl group-introducing enzyme gene (crt Z gene) of the marine bacterium *Agrobacterium aurantiacus* sp. nov. MK1 and the amino acid sequence of a polypeptide to be encoded thereby (SEQ ID NOS:3–4).

FIG. 3 the nucleotide sequence of the lycopene-cyclizing enzyme gene (crt Y gene) of the marine bacterium *Agrobacterium aurantiacus* sp. nov. MK1 and the amino acid sequence of a polypeptide to be encoded thereby (SEQ ID NOS:5–6).

FIG. 4 the continuation of the sequence following to those illustrated in FIG. 3 (SEQ ID NOS:5–6).

FIG. 5 the nucleotide sequence of the xanthophyll synthesis gene cluster of the marine bacterium *Agrobacterium aurantiacus* sp. nov. MK1 (SEQ ID NO:7).

The letters A–F in FIG. 5 correspond to those in FIGS. 1–4.

FIG. 6 the continuation of the sequence following to that illustrated in FIG. 5 (SEQ ID NO:7).

FIG. 7 the continuation of the sequence following to that illustrated in FIG. 6 (SEQ ID NO:7).

FIG. 8 the continuation of the sequence following to that illustrated in FIG. 7 (SEQ ID NO:7).

FIG. 9 the continuation of the sequence following to that illustrated in FIG. 8 (SEQ ID NO:7).

Figure 10:
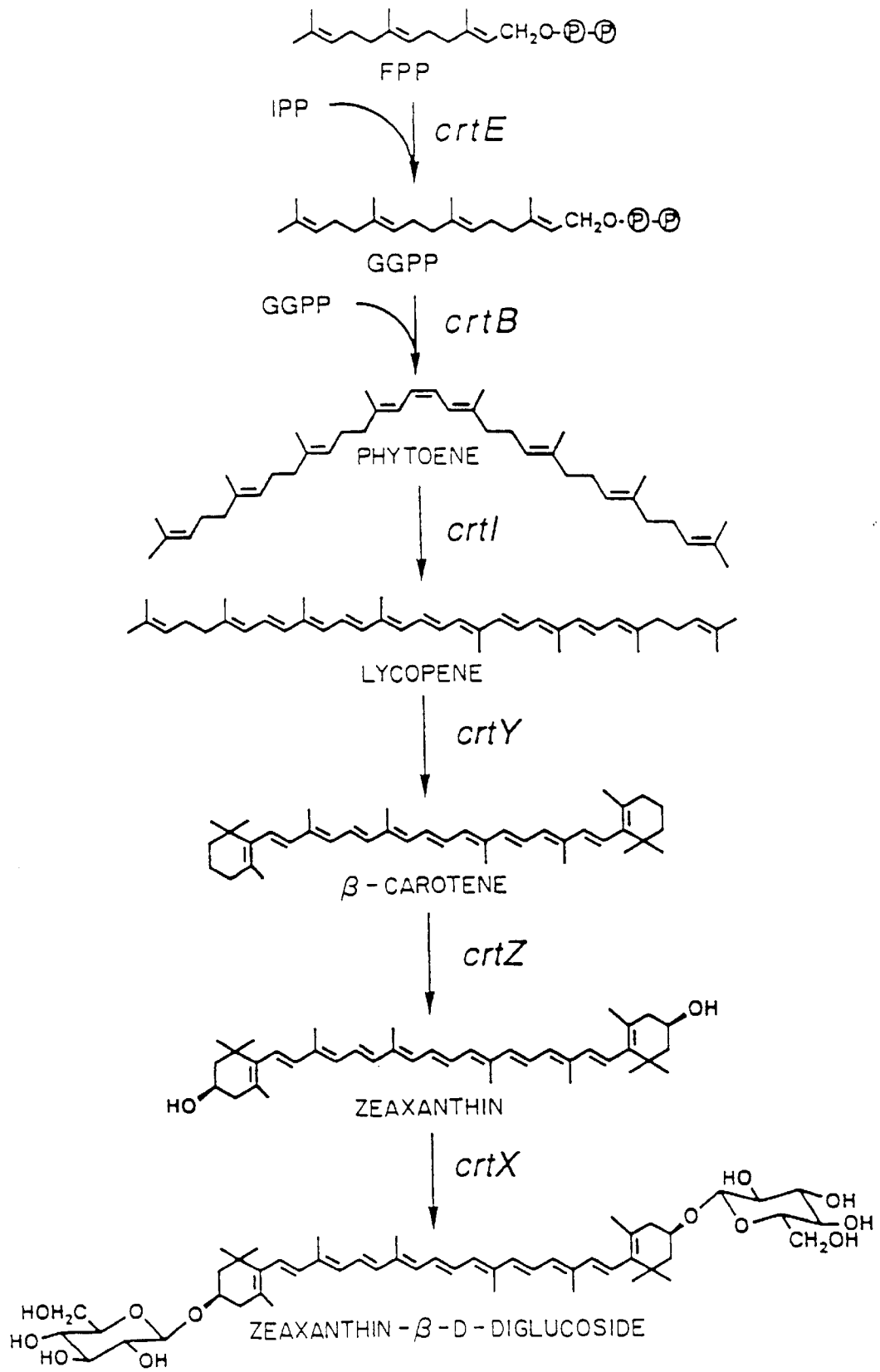

FIG. 10 the carotenoid biosynthetic route of the non-photosynthesis bacterium *Erwinia uredovora* and the functions of the carotenoid synthetic genes.

Figure 11:
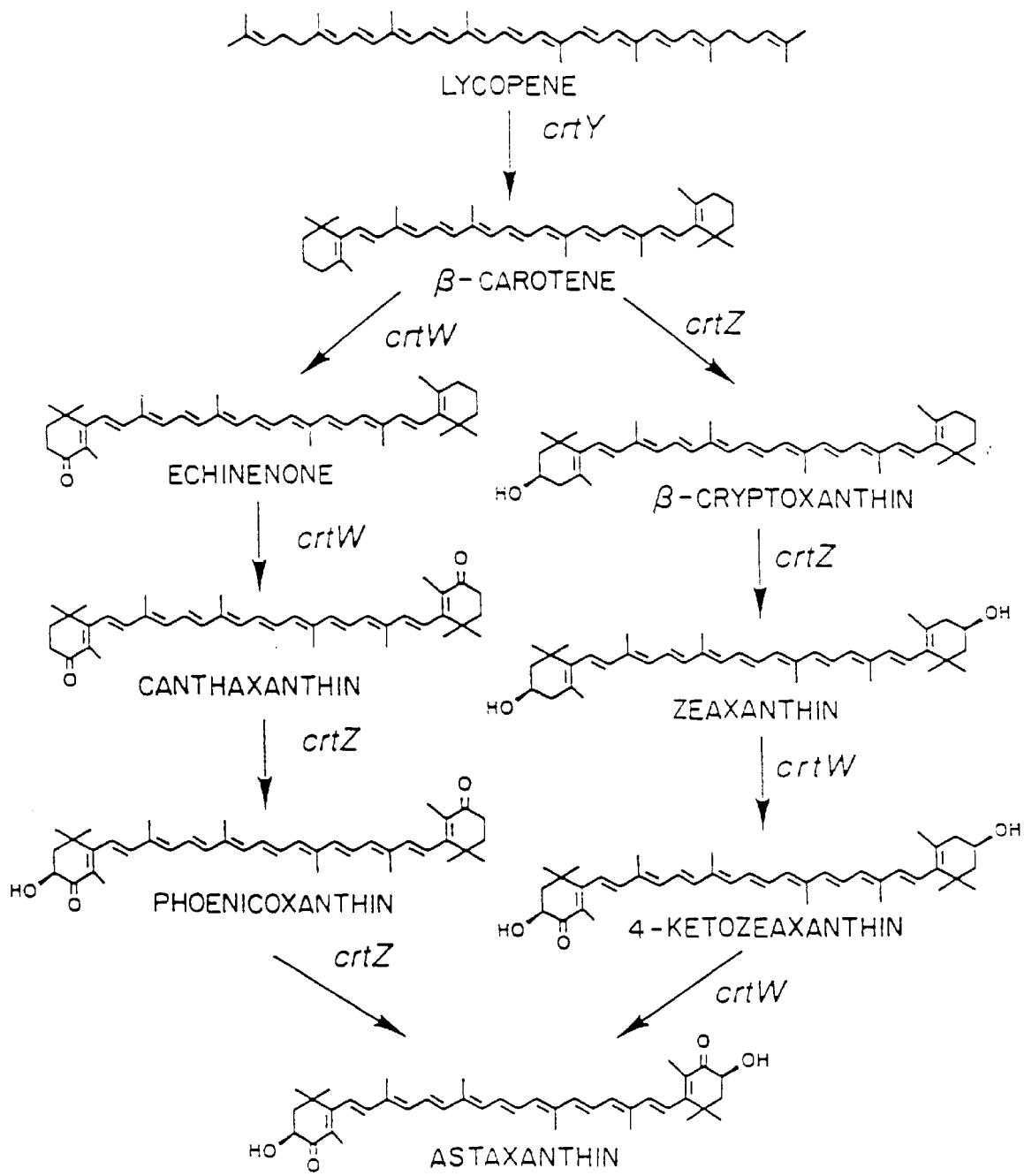

FIG. 11 the main xanthophyll biosynthetic routes of the marine bacteria *Agrobacterium aurantiacus* sp. nov. MK1 and Alcaligenes sp. PC-1 and the functions of the xanthophyll synthesis genes.

The function of crtY gene, however, has been confirmed only in the former bacterium.

FIG. 12 the deletion plasmids containing the xanthophyll synthesis genes (cluster) of the marine bacterium *Agrobacterium aurantiacus* sp. nov. MK1.

The letter P represents the promoter of the lac of the vector pBluescript II SK. The positions of cutting with restriction enzymes are represented by abbreviations as follows: Sa, SacI; X, XbaI; B, BamHI; P, PstI; E, EcoRI: S, SalI; A, ApaI; K, KpnI; St, StuI; N, NruI; Bg, BglII; Nc, NcoI; Hc, HincII.

FIG. 13 the nucleotide sequence of the keto group-introducing enzyme gene (crtW gene) of the marine bacterium Alcaligenes sp. PC-1 and the amino acid sequence of a polypeptide to be encoded thereby (SEQ ID NOS:8–9).

FIG. 14 the continuation of the sequences following to those illustrated in FIG. 13 (SEQ ID NOS:8–9).

FIG. 15 the nucleotide sequence of the hydroxyl group-introducing enzyme gene (crtZ gene) of the marine bacterium Alcaligenes sp. PC-1 and the amino acid sequence of a polypeptide to be encoded thereby (SEQ ID NOS:10–11).

FIG. 16 the nucleotide sequence of the xanthophyll synthetic gene cluster of the marine bacterium Alcaligenes sp. PC-1 and the amino acid sequence of a polypeptide to be encoded thereby (SEQ ID NO:12). The letters A–D in FIG. 16 correspond to those in FIGS. 13–15.

FIG. 17 the continuation of the sequence following to that illustrated in FIG. 16 (SEQ ID NO:12).

FIG. 18 the continuation of the sequence following to that illustrated in FIG. 17 (SEQ ID NO:12).

FIG. 19 a variety of deletion plasmids containing the xanthophyll synthetic genes (cluster) of the marine bacterium Alcaligenes sp. PC-1.

The letter P represents the promoter of the lac of the vector pBluescript II SK+.

Figure 20:
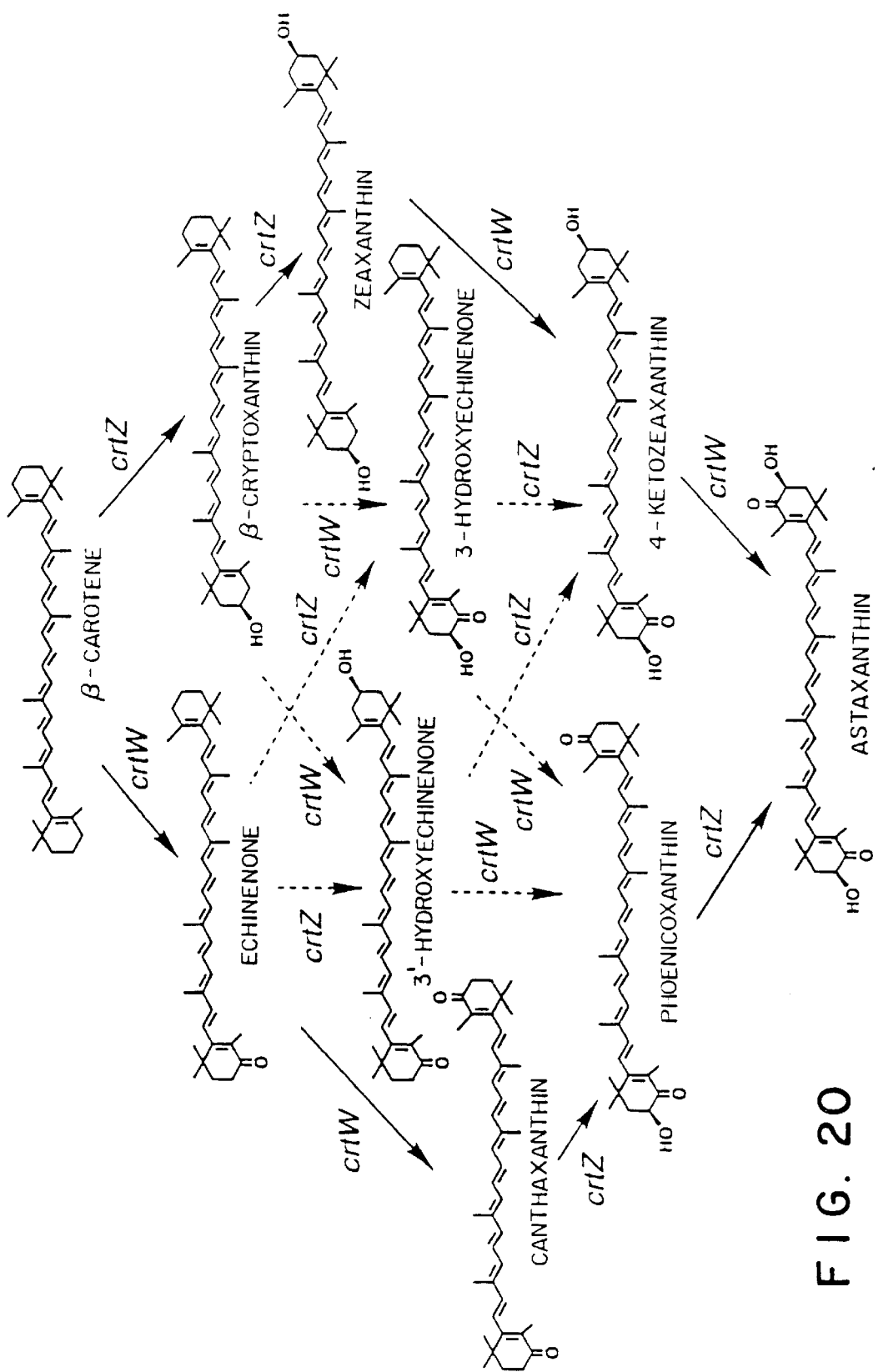

FIG. 20 xanthophyll biosynthetic routes containing miner biosynthetic routes in the marine bacteria *Agrobacterium aurantiacus* sp. no. MK1 and Alcaligenes sp. PC-1 and the functions of the xanthophyll synthesis genes.

Miner biosynthetic routes are represented by dotted arrows.

BEST MODE FOR CARRYING OUT THE INVENTION

The present invention is intended to provide DNA strands which are useful for synthesizing keto group-containing xanthophylls (ketocarotenoids) such as astaxanthin derived from a marine bacteria *Agrobacterium aurantiacus* sp. nov. MK1 and Alcaligenes sp. PC-1, and a process for producing keto group-containing xanthophylls (ketocarotenoids), i.e. astaxanthin, phoenicoxanthin, 4-ketozeaxanthin, canthaxanthin, and echinenone with use of a microorganism into which the DNA strands have been introduced.

The DNA strands according to the present invention are in principle illustrated generally by the aforementioned DNA strands (1), (10) and (19) from the standpoint of the fine chemical-generating reaction, and basically defined by the aforementioned DNA strands (2), (4), (11), (13), (20) and (22). The specific examples of the DNA strands (2) and (4) are the aforementioned DNA strands (6) and (8); the specific examples of the DNA strands (11) and (13) are the aforementioned DNA strands (15) and (17); and the specific examples of the DNA strands (20) and (22) are the aforementioned DNA strands (24) and (26). In this connection, the DNA strands (3), (5), (7), (9), (12), (14), (16), (18), (21), (23), (25) and (27) hybridize the DNA strands (2), (4), (6), (8), (11), (13), (15), (17), (20), (22), (24) and (26), respectively, under a stringent condition.

The polypeptides encoded by the DNA strands according to the present invention have amino acid sequences substantially in a specific range as described above in SEQ ID NOS:2, 4, 9 and 11 (FIGS. 1–2, and 13–15), e.g. an amino acid sequence of amino acid Nos. 1–212 in SEQ ID NO:2 (A–B in FIG. 1). In the present invention, four polypeptides encoded by these DNA strands, that is four enzymes participating in the xanthophyll-producing reaction) may be modified by deletion, substitution or addition in some of the amino acids provided that the polypeptides have the enzyme activities as described above (see Example 13). This corresponds to that "amino acid sequences . . . substantially . . . ". For instance, an enzyme of which amino acid at the first position (Met) has been deleted is also involved in the polypeptide or enzyme obtained by the modification of the amino acid sequence. In this connection, it is needless to say that the DNA strands according to the present invention for encoding the polypeptides also include, in addition to those having nucleotide sequences in a specific range shown in SEQ ID NOS:2, 4, 9 and 11 (FIGS. 1–2, and 13–15), degenerate isomers encoding the same polypeptides as above except degenerate codons.

Keto group-introducing enzyme gene (crtW)

The DNA strands (1)–(18) are genes which encode the keto group-introducing enzymes (referred to hereinafter as crtW). Typical examples of the genes are crtW genes cloned form the marine bacteria *Agrobacterium aurantiacus* sp. nov. MK1 or Alcaligenes sp. PC-1, which are the DNA strands comprising the nucleotide sequences encoding the polypeptides having the amino acid sequences A–B in FIG. 1 (amino acid No. 2–212 in SEQ ID NOS:1) or A–B in FIGS. 13–14 (amino acid Nos. 1–242 in SEQ ID NO:9). The crtW gene product (also referred to hereinafter as CrtW) has an enzyme activity for converting the 4-methylene group of the β-ionone ring into a keto group, and one of the specific examples is an enzyme activity for synthesizing canthaxanthin with β-carotene as a substrate by way of echinenone (see FIG. 11). In addition, the crtW gene product also has an enzyme activity for converting the 4-methylene group of the 3-hydroxy-β-ionone ring into a keto group, and one of the specific examples is an enzyme activity for synthesizing astaxanthin with zeaxanthin as a substrate by way of 4-ketozeaxanthin (see FIG. 11). In this connection, the polypeptides having such enzyme activities and the DNA strands encoding the polypeptides have not hitherto been reported, and the polypeptides or the DNA strands encoding the polypeptides has no overall homology to polypeptides or DNA strands which have hitherto been reported. Moreover, no such information has been reported that one enzyme has an activity to convert directly a methylene group of not only the β-ionone ring and the 3-hydroxy-β-ionone ring but also the other compounds into a keto group. Moreover, a homology of CrtW as high as 83% identity at an amino acid sequence level was shown between Agrobacterium and Alcaligenes.

On the other hand, it is possible to allow a microorganism such as *Escherichia coli* or the like to produce β-carotene or zeaxanthin by using the carotenoid synthesis genes of the non-photosynthetic bacterium Erwinia, that is the crtE, crtB, crtI and crtY genes of Erwinia afford the microorganism such as *Escherichia coli* or the like the β-carotene-producing ability, and the crtE, crtB, crtI, crtY and crtZ genes of Erwinia afford the microorganisms such as *Escherichia coli* or the like the zeaxanthin-producing ability (see FIG. 10 and Laid-Open Publication of WO91/13078). Thus, the substrate of CrtW is supplied by the crt gene cluster of Erwinia, so that when an additional crtW gene is introduced into a microorganism such as *Escherichia coli* or the like which contains the aforementioned crt gene cluster of Erwinia, the β-carotene-producing microorganism will produce canthaxanthin by way of echinenone, and the zeaxanthin-producing microorganism will produce astaxanthin by way of 4-ketozeaxanthin.

Hydroxyl group-introducing enzyme gene (crtZ)

The DNA strands (19)–(27) are genes encoding a hydroxyl group-introducing enzyme (referred to hereinafter as crtZ). Typical examples of the genes are crtZ genes cloned from the marine bacteria *Agrobacterium aurantiacus* sp. nov. MK1 or Alcaligenes sp. PC-1, which are DNA strands comprising nucleotide sequences encoding the polypeptides having the amino acid sequences C–D in FIG. 2 (amino acid Nos. 1–162 in SEQ ID NO:4) or C–D in FIGS. 15 (amino acid Nos. 1–162 in SEQ ID NO:11). The crtZ gene product (also referred to hereinafter as CrtZ) has an enzyme activity for adding a hydroxyl group to the 3-carbon atom of the β-ionone ring, and one of the specific examples is an enzyme activity for synthesizing zeaxanthin with use of β-carotene as a substrate by way of β-cryptoxanthin (see FIG. 11). In addition, the crtZ gene product also has an enzyme activity for adding a hydroxyl group to the 3-carbon atom of the 4-keto-β-ionone ring, and one of the specific examples is an enzyme activity for synthesizing astaxanthin with canthaxanthin as a substrate by way of phoenicoxanthin (see FIG. 11). In this connection, the polypeptide having the latter enzyme activity and the DNA strand encoding the polypeptide have not hitherto been reported. Moreover, CrtZ of Agrobacterium and Alcaligenes showed a high homology with CrtZ of Erwinia uredovora (57% and 58% identity), respectively, at an amino acid sequence level. Also, a high homology of 90% identity at an amino acid sequence level was shown between the CrtZ of Agrobacterium and Alcaligenes.

It has been described above that a microorganism such as Escherichia coli or the like can produce β-carotene by using the carotenoid synthetic genes of the non-photosynthetic bacterium Erwinia. Moreover, it has been described above that a microorganism such as Escherichia coli or the like can produce canthaxanthin by adding crtW thereto. Thus, the substrate CrtZ of Agrobacterium or Alcaligenes is supplied by the crtE, crtB, crtI and crtY genes of Erwinia (production of β-carotene), and the crtW gene of Agrobacterium or Alcaligenes is added thereto, so that when the crtZ gene of Agrobacterium or Alcaligenes is introduced into a microorganism such as Escherichia coli or the like containing the crt gene group, the β-carotene-producing microorganism will produce zeaxanthin by way of β-cryptoxanthin, and the canthaxanthin-producing microorganism will produce astaxanthin by way of phoenicoxanthin.

Lycopene-cyclizing enzyme gene (crtY)

The DNA strand encoding the amino acid sequence substantially from E to F of FIGS. 3 and 4 (amino acid Nos. 1–386 in SEQ ID NO:6) is a gene encoding a lycopene-cyclizing enzyme (referred to hereinafter as crtY). A typical example of the gene is the crtY gene cloned from the marine bacterium Agrobacterium aurantiacus sp. nov. MK1, which is the DNA strand comprising the nucleotide sequence encoding the polypeptide having the amino acid sequence E–F in FIGS. 3 and 4. The crtY gene product (also referred to hereinafter as CrtY) has an enzyme activity for synthesizing β-carotene with lycopene as a substrate (see FIG. 11). It is possible to allow a microorganism such as Escherichia coli or the like to produce lycopene by using a carotenoid biosynthesis genes of an on-photosynthetic bacterium Erwinia, that is the crtE, crtB and crtI genes of Erwinia give a microorganism such as Escherichia coli or the like a lycopene biosynthesis ability (see FIG. 10, and Laid-Open Publication of WO91/13078). Thus, the substrate of the CrtY of Agrobacterium is supplied by the crt gene group of Erwinia, so that when the crtY of Agrobacterium is introduced into a microorganism such as Escherichia coli or the like containing the crt gene group, it is possible to allow the microorganism to produce β-carotene.

In this connection, the CrtY of Agrobacterium has a significant homology of 44.3% identity to the CrtY of Erwinia uredovora at the amino acid sequence level, and these CrtY enzymes also have the same enzymatic function (see FIGS. 10 and 11).

Bacteriological properties of marine bacteria

The marine bacteria Agrobacterium aurantiacus sp. nov. MK1 and Alcaligenes sp. PC-1 as the sources of the xanthophyll synthetic genes show the following bacteriological properties.

<Agrobacterium aurantiacus sp. nov. MK1>
(1) Morphology
Form and size of bacterium: short rod, 0.9 μm×1.2 μm;
Motility: yes;
Flagellum: peripheric flagellum
Polymorphism of cell: none;
Sporogenesis: none;
Gram staining: negative.
(2) Growth in culture media
Broth agar plate culture: non-diffusive circular orange colonies having a gloss are formed.
Broth agar slant culture: a non-diffusive orange band having a gloss is formed.
Broth liquid culture: homogeneous growth all over the culture medium with a color in orange.
Broth gelatin stab culture: growth over the surface around the stab pore.
(3) Physiological properties
Reduction of nitrate: positive;
Denitrification reaction: negative;
Formation of indole: negative;
Utilization of citric acid: negative;
Formation of pigments: fat-soluble reddish orange pigment;
Urease activity: negative;
Oxidase activity: positive;
Catalase activity: positive;
β-Glucosidase activity (esculin degradability): positive;
β-Galactosidase activity: positive;
Growth range: pH, 5–9; temperature, 10–40° C.;
Behavior towards oxygen: aerobic;
Durability to seawater: positive;
O–F test: oxidation;
Anabolic ability of saccharides:
    Positive: D-glucose, D-mannose, D-galactose, D-fructose, lactose, maltose, sucrose, glycogen, N-acetyl-D-glucosamine;
    Negative: L-arabinose, D-mannitol, inositol, L-rhamnose, D-sorbitol;
Anabolic ability of organic acids:
    Positive: lactate;
    Negative: citrate, malate, gluconate, caprinate, succinate, adipate;
Anabolic ability of the other organic materials:
    Positive: inosine, uridine, glucose-1-phosphate, glucose-6-phosphate;
    Negative: gelatin, L-arginine, DNA, casein.
<Alcaligenes sp. PC-1>
(1) Morphology
Form and size of bacterium: short rod, 1.4 μm;
Motility: yes;
Flagellum: peripheric flagellum;
Polymorphism of cell: none;
Sporogenesis: none;
Gram staining: negative.
(2) Growths in culture media
Broth agar plate culture: non-diffusive circular orange colonies having a gloss are formed.
Broth agar slant culture: a non-diffusive orange band having a gloss if formed.

Broth liquid culture: homogeneous growth all over the culture medium with a color in orange.

Broth gelatin stab culture: growth over the surface around the stab pore.

(3) Physiological properties

Formation of pigments: fat-soluble reddish orange pigment;

Oxidase activity: positive;

Catalase activity: positive;

Growth range: pH, 5–9; temperature, 10°–40° C.;

Behavior towards oxygen: aerobic;

Durability to seawater: positive;

O–F test: oxidation;

Degradability of gelatin: negative.

Xanthophyll synthetic gene cluster of the other marine bacteria

It has hitherto been reported that 16 marine bacteria have an ability to synthesize ketocarotenoids such as astaxanthin and the like (Yokoyama, A., Izumida, H., Miki, W., "Marine bacteria produced astaxantin", 10th International Symposium on Carotenoids, Abstract, CL11-3, 1993). If either of the crt genes of the aforementioned marine bacteria *Agrobacterium aurantiacus* sp. nov. MK-1 or Alcaligenes sp. PC-1 is used as a probe, the gene cluster playing a role of the biosynthesis of ketocarotenoids such as astaxanthin and the like should be obtained from the other astaxanthin producing marine bacteria by using the homology of the genes. In fact, the present inventors have successfully obtained the crtW and crtZ genes as the strongly hybridizing DNA fragments from the chromosomal DNA of Alcaligenes PC-1 with use of a DNA fragment containing crtW and crtZ of *Ag. aurantiacus* sp. nov. MK1 as a probe (see Examples as for the details). Furthermore, when Alteromonas SD-402 was selected from the remaining 14 marine bacteria having an astaxanthin synthetic ability and a chromosomal DNA was prepared therewith and subjected to the Southern hybridization experiment with a DNA fragment containing crtW and crtZ of *Ag. aurantiacus* sp. nov. MK1, the probe hybridized with the bands derived from the chromosomal DNA of the marine bacteria. The DNA strands according to the present invention also include a DNA strand which hybridizes with the DNA strands (2), (4), (6), (8), (11), (13), (15), (17), (20), (22), (24) and (26).

Acquisition of DNA strands

Although one of the methods for obtaining the DNA strand having a nucleotide sequence which encodes the amino acid sequence of each enzyme described above is to chemically synthesize at least a part of the strand length according to the method for synthesizing a nucleic acid, it is believed more preferable than the chemical synthetic method to obtain the DNA strand by using the total DNA having been digested with an appropriate restriction enzyme to prepare a library in *Escherichia coli*, from which library the DNA strand is obtained by the methods conventionally used in the art of genetic engineering such as a hybridization method with an appropriate probe (see the xanthophyll synthetic gene cluster of the other marine bacteria).

Transformation of an microorganism such as *Escherichia coli* and gene expression A variety of xanthophylls can be prepared by introducing the present DNA strands described above into an appropriate microorganism such as a bacterium, for example *Escherichia coli, Zymomonas mobilis* and *Agrobacterium tumefaciens,* and yeast, for example *Saccharomyces cerivisiae.*

The outline for introducing a foreign gene into a preferred microorganism is described below.

The procedure or method for introducing and expressing the foreign gene in a microorganism such as *Escherichia coli* or the like comprises the ones usually used in the art of genetic engineering in addition to those described below in the present invention and may be carried out according to the procedure or method (see, e.g., "Vectors for Cloning Genes", Methods in Enzymology, 216, p. 469–631, 1992, Academic Press, and "Other Bacterial Systems", Methods in Enzymology, 204, p. 305–636, 1991, Academic Press).

<*Escherichia coli*>

The method for introducing foreign genes into *Escherichia coli* includes several efficient methods such as the Hanahan's method and the rubidium method, and the foreign genes may be introduced according to these methods (see, for example, Sambrook, J., Fritsch, E. F., Maniatis, T., "Molecular Cloning—A Laboratory Manual", Cold Spring Harbor Laboratory Press, 1989). While foreign genes in *Escherichia coli* may be expressed according to the convention methods (see, for example, "Molecular Cloning—A Laboratory Manual"), the expression can be carried out for example with a vector for *Escherichia coli* having a lac promoter in the pUC or pBluescript series. The present inventors have used a vector pBluescript II SK or KS for *Escherichia coli* having a lac promoter and the like to insert eh crtW, crtZ and crtY genes of *Agrobacterium aurantiacus* sp. nov. MK1 and the crtW and crtZ genes of Alcaligenes sp. PC-1 and allowed to express these genes in *Escherichia coli.*

<Yeast>

The method for introducing foreign genes into yeast *Saccharomyces cerivisiae* includes the methods which have already been established such as the lithium method and the like, and the introduction may be carried out according to these methods (see, for example, Ed. Yichi Akiyama, compiled by Bio-industry Association, "New Biotechnology of Yeast", published by IGAKU SHUPPAN CENTER). Foreign genes can be expressed in yeast by using a promoter and a terminator such as PGK and GPD to construct an expression cassette in which the foreign gene is inserted between the promoter and the terminator so that transcription is led through, and inserting the expression cassette into a vector such as the YRp system which is a multi-copy vector for yeast having the ARS sequence of the yeast chromosome as the replication origin, the YEp system which is a multi-copy vector for yeast having the replication origin of the 2 μm DNA of yeast, and the YIp system which is a vector for integrating a yeast chromosome having no replication origin of yeast (see "New Biotechnology of Yeast", published by IGAKU SHUPPAN CENTER, ibid.; NIPPON NOGEI-KAGAKU KAI ABC Series "Genetic Engineering for Producing Materials", published by ASAKURA SHOTEN; and Yamano, S., Ishii, T., Nakagawa, M., Ikenaga, H., Misawa, N., "Metabolic Engineering for Production of β-carotene and lycopene in *Saccharomyces cerevisiae*", Biosci. Biotech. Biochem., 58, p. 1112–1114, 1994).

<*Zymomonas mobilis*>

Foreign genes can be introduced into an ethanol-producing bacterium *Zymomonas mobilis* by the conjugal transfer method which is common to Gram-negative bacteria, and the foreign genes can be expressed by using a vector pZA22 for *Zymomonas mobilis* (see Katsumi Nakamura, "Molecular Breeding of *Zymomonas mobilis*", Nippon Nogei-Kagaku Kaishi, 63, p. 1016–1018, 1989; and Misawa, N., Yamano, S., Ikanaga, H., "Production of β-Carotene in *Zymomonas mobilis* and *Agrobacterium tumefaciens* by Introduction of the Biosynthesis Genes from *Erwinia uredovora*", Appl. Environ. Microbiol., 57, p. 1847–1849, 1991).

<Agrobacterium tumefaciens>

Foreign genes can be introduced into a plant pathogenic bacterium *Agrobacterium tumefaciens* by the conjugal transfer method which is common to Gram-negative bacteria, and the foreign genes can be expressed by using a vector pBI121 for a bacterium such as *Agrobacterium tumefaciens* (see Misawa, N., Yamano, S., Ikenaga, H., "Production of β-Carotene in *Zymomonas mobilis* and *Agrobacterium tumefaciens* by Introduction of the Biosynthesis Genes from *Erwinia uredovora*", Appl. Environ. Microbiol., 57, p. 1847–1849, 1991).

Production of xanthophylls by microorganisms

The gene cluster for the synthesis of ketocarotenoids such as astaxanthin derived from a marine bacterium can be introduced and expressed by the procedure or method described above for introducing and expressing an foreign gene in a microorganism.

Farnesyl pyrophosphate (FPP) is a substrate which is common not only to carotenoids but also to other terpenoids such as sesquiterpenes, triterpenes, sterole, hopanols and the like. In general, microorganisms synthesize terpenoids even if they cannot synthesize carotenoids, so that all of the microorganisms should basically have FPP as an intermediate metabolite. Furthermore, the carotenoid synthesis gene cluster of a non-photosynthetic bacterium Erwinia has an ability to synthesize the substrates of the crt gene products of *Agrobacterium aurantiacus* sp. nov. MK1 or Alcaligenes sp. PC-1 by using FPP as a substrate (see FIG. 10). The present inventors have already confirmed that when the group of crt genes of Erwinia is introduced into not only *Escherichia coli* but also the aforementioned microorganisms, that is the yeast *Saccharomyces cerevisiae*, the ethanol producing bacterium *Zymomonas mobilis,* or the plant pathogenic bacterium *Agrobacterium tumefaciens*, carotenoids such as β-carotene and the like can be produced, as was expected, by these microorganisms (Yamano, S., Ishii, T., Nakagawa, M. Ikenaga, H., Misawa, N., "Metabolic Engineering for Production of β-Carotene and Lycopene in *Saccharomyces cerevisiae*", Biosci. Biotech. Biochem., 58, p. 1112–1114, 1994; Misawa, N., Yamano, S., Ikenaga, H., "Production of β-Carotene in *Zymomonas mobilis* and *Agrobacterium tumefaciens* by Introduction of the Biosynthetic Genes from *Erwinia uredovora*", Appl. Environ. Microbiol., 57, p. 1847–1849, 1991; and Japanese Patent Application No. 58786/1991 (Japanese Patent Application No. 53255/1990) by the present inventors: "DNA Strands useful for the Synthesis of Carotenoids").

Thus, it should be possible in principle to allow all of the microorganisms, in which the gene introduction and expression system has been established, to produce ketocarotenoids such as astaxanthin and the like by introducing the combination of the carotenoid synthesis gene cluster derived from Erwinia and the DNA strands according to the present invention (typically the carotenoid synthesis gene cluster derived from *Agrobacterium aurantiacus* sp. nov. MK1 or Alcaligenes sp. PC-1) at the same time into the same microorganism. The process for producing a variety of ketocarotenoids in microorganisms are described below.

<Production of canthaxanthin and echinenone>

It is possible to produce canthaxanthin as a final product and echinenone as an intermediate metabolite by introducing into a microorganism such as *Escherichia coli* and expressing the crtE, crtB, crtI and crtY genes of *Erwinia uredovora* required for the synthesis of β-carotene and any one of the DNA strands of the present invention (1)–(9) which is a keto group-introducing enzyme gene (typically, the crtW gene of *Agrobacterium aurantiacus* sp. nov. MK1 or Alcaligenes PC-1). The yields or the ratio of canthaxanthin and echinenone can be changed by controlling the expression level of the DNA strand (crtW gene) or examining the culturing conditions of a microorganism having the DNA strand. Two embodiments in *Escherichia coli* are described below, and more details will be illustrated in Examples.

A plasmid pACCAR16ΔcrtX that a fragment containing the crtE, crtB, crtI and crtY genes of *Erwinia uredovora* has been inserted into the *Escherichia coli* vector pACYC184 and a plasmid pAK916 that a fragment containing the crtW gene of *Agrobacterium aurantiacus* sp. nov. MK1 has been inserted into the *Escherichia coli* vector pBluescript II SK– were introduced into *Escherichia coli* JM101 and cultured to the stationary phase to collect bacterial cells and to extract carotenoid pigments. The extracted pigments comprised 94% of canthaxanthin and 6% of echinenone. Also, canthaxanthin was obtained in a yield of 3 mg starting from 2 liters of the culture solution.

A plasmid pACCAR16ΔcrtX that a fragment containing the crtE, crtB, crtI and crtY genes of *Erwinia uredovora* has been inserted into the *Escherichia coli* vector pACYC184 and a plasmid pPC17-3 that a fragment containing the crtW gene of Alcaligenes PC-1 has been inserted into the *Escherichia coli* vector pBluescript II SK+ were introduced into *Escherichia coli* JM101 and cultured to the stationary phase to collect bacterial cells and to extract carotenoid pigments. The extracted pigments comprised 40% of canthaxanthin and 50% of echinenone. The remainder comprised 10% of unreacted β-carotene. <Production of astaxanthin and 4-ketozeaxanthin>

It is possible to produce astaxanthin as a final product and 4-ketozeaxanthin as an intermediate metabolite by introducing into a microorganism such as *Escherichia coli* or the like and expressing the crtE, crtB, crtI, crtY and crtZ genes of *Erwinia uredovora* required for the synthesis of zeaxanthin and any one of the DNA strands of the present invention (10)–(18) which is a keto group-introducing enzyme gene (typically, the crtW gene of *Agrobacterium aurantiacus* sp. nov. MK1 or Alcaligenes PC-1). The yields or the ratio of astaxanthin and 4-ketozeoxanthin can be changed by controlling the expression level of the DNA strand (crtW gene) or examining the culturing conditions of a microorganism having the DNA strand.

Two embodiments in *Escherichia coli* are described below, and more details will be illustrated in Examples.

A plasmid pACCAR25ΔcrtX that a fragment containing the crtE, crtB, crtI, crtY and crtZ genes of *Erwinia uredovora* has been inserted into the *Escherichia coli* vector pACYC184 and a plasmid pAK916 that a fragment containing the crtW gene of *Ag. aurantiacus* sp. nov. MK1 has been inserted into the *Escherichia coli* vector pBluescript II SK– were introduced into *Escherichia coli* JM101 and cultured to the stationary phase to collect bacterial cells and to extract carotenoid pigments. The yield of the extracted pigments was 1.7 mg of astaxanthin and 1.5 mg of 4-ketozeaxanthin based on 2 liters of the culture solution.

A plasmid pACCAR25ΔcrtX that a fragment containing the crtE, crtB, crtI, crtY and crtZ genes of *Erwinia uredovora* has been inserted into the *Escherichia coli* vector pACYC184 and a plasmid pPC17-3 that a fragment containing the crtW gene of Alcaligenes PC-1 has been inserted into the *Escherichia coli* vector pBluescript II SK+ were introduced into *Escherichia coli* CM101 and cultured to the stationary phase to collect bacterial cells and to extract carotenoid pigments. The yield of the extracted pigments was about 1 mg of astaxanthin and 4-ketozeaxanthin, respectively based on 2 liters of the culture solution. <Production of astaxanthin and phoenicoxanthin>

It is possible to produce astaxanthin as a final product and phoenicoxanthin as an intermediate metabolite by introducing into a microorganism such as *Escherichia coli* or the like and expressing the crtE, crtB, crtI and crtY genes of *Erwinia uredovora* required for the synthesis of β-carotene, any one of the DNA strands of the present invention (1)–(9) which is a keto group-introducing enzyme gene (typically, the crtW gene of *Agrobacterium aurantiacus* sp. nov. MK1 or Alcaligenes PC-1), and any one of the DNA strands of the present invention (19)–(27) which is a hydroxyl group-introducing enzyme gene (typically, the crtZ gene of *Ag. aurantiacus* sp. nov. MK1 or Alcaligenes PC-1). The yields or the ratio of astaxanthin and phoenicoxanthin can be changed by controlling the expression level of the DNA strands (crtW and crtZ genes) or examining the culturing conditions of a microorganism having the DNA strands. An embodiment in *Escherichia coli* are described below, and more details will be illustrated in Examples.

A plasmid pACCAR16ΔcrtX that a fragment containing the crtE, crtB, crtI and crtY genes of *Erwinia uredovora* has been inserted into the *Escherichia coli* vector pACYC184 and a plasmid pAK96K that a fragment containing the crtW and crtZ genes of *Ag. aurantiacus* sp. nov. MK1 has been inserted into the *Escherichia coli* vector pBluescript II SK– were introduced into *Escherichia coli* JM101 and cultured to the stationary phase to collect bacterial cells and to extract carotenoid pigments. The yield of the extracted pigments comprised was 3 mg of astaxanthin and 2 mg of phoenicoxanthin starting from 4 liters of the culture solution.

Deposition of microorganisms

Microorganisms as the gene sources of the DNA strands of the present invention and *Escherichia coli* carrying the isolated genes (the DNA strands of the present invention) have been deposited in the National Institute of Bioscience and Human Technology, Agency of Industrial Science and Technology.

(i) *Agrobacterium aurantiacus* sp. nov. MK1
   Deposition No: FERM BP-4506
   Entrusted Date: Dec. 20, 1993
(ii) *Escherichia coli* JM101 (pAccrt-EIB, pAK92)
   Deposition No: FERM BP-4505
   Entrusted Date: Dec. 20, 1993
(iii) Alcaligenes sp. PC-1
   Deposition No: FERM BP-4760
   Entrusted Date: Jul. 27, 1994
(iv) *Escherichia coli* β: pPC17
   Deposition No: FERM BP-4761
   Entrusted Date: Jul. 27, 1994

EXAMPLES

The present invention is further described more specifically with reference to the following examples without restriction of the invention. In addition, the ordinary experiments of gene manipulation employed herein is based on the standard methods (Sambrook, J., Fritsch, E. F., Maniatis, T., "Molecular Cloning—A Laboratory Manual", Cold Spring Harbor Laboratory Press, 1989), unless otherwise specified.

Example 1

Preparation of Chromosomal DNA

Chromosomal DNAs were prepared from three marine bacterial strains, i.e. *Agrobacterium aurantiacus* sp. nov. MK1, Alcaligenes sp. PC-1, and Alteromonas SD-402 (Yokoyama, A., Izumida, H., Miki, W., "Marine bacteria produced astaxanthin", 10th International Symposium on Carotenoids, Abstract, CL11-3, 1993). After each of these marine bacteria was grown in 200 ml of a culture medium (a culture medium prepared according to the instruction of "Marine Broth" manufactured by DIFCO) at 25° C. for 4 days to the stationary phase, the bacterial cells were collected, washed with a TES buffer (20 mM Tris, 10 mM EDTA, 0.1M NaCl, pH8), subjected to heat treatment at 68° C. for 15 minutes, and suspended into the solution I (50 mM glucose, 25 mM Tris, 10 mM EDTA, pH 8) containing 5 mg/ml of lysozyme (manufactured by SEIKAGAKU KOGYO) and 100 μg/ml of RNase A (manufactured by Sigma). After incubation of the suspension at 37° C. for 1 hour, Proteinase K (manufactured by Boehringer-Mannheim) was added and the mixture was incubated at 37° C. for 10 minutes. After SARCOSIL (N-lauroylsarcosine Na, manufactured by Sigma) was then added at the final concentration of 1% and the mixture was sufficiently mixed, it was incubated at 37° C. for several hours. The mixture was extracted several times with phenol/chloroform, and ethanol in a two-time amount was added slowly. Chromosomal DNA thus deposited was wound around a glass rod, rinsed with 70% ethanol and dissolved in 2 ml of a TE buffer (10 mM Tris, 1 mM EDTA, pH 8) to prepare a chromosomal DNA solution.

Example 2

Preparation of Hosts for a Cosmid Library (1) Preparation of phytoene-producing *Escherichia coli*

After the removal of the BstEII (1235)-Eco521 (4926) fragment from a plasmid pCAR16 having a carotenoid synthesis gene cluster except the crtZ gene of *Erwinia uredovora* (Misawa, N., Nakagawa, M., Kobayashi, K., Yamano, S., Izawa, Y., Nakamura, K., Harashima, K., "Elucidation of the *Erwinia uredovora* Carotenoid Biosynthetic Pathway by Functional Analysis of Gene Products expressed in *Escherichia coli*", J. Bacteriol., 172, p. 6704–6712, 1990; and Japanese Patent Application No. 58786/1991 (Japanese Patent Application No. 53255/1990): "DNA Strands useful for the Synthesis of Carotenoids"), a 2.3 kb Asp718 (KpnI)-EcoRI fragment containing the crtE and crtB genes required from the production of phytoenes was cut out. This fragment was then inserted into the EcoRV site of the *E. coli* vector pACYC184 to give an aimed plasmid (pACCRT-EB). The bacterium *E. coli* containing pACCRT-EB exhibits resistance to an antibiotic chloramphenicol ($Cm^r$) and produces phytoenes (Linden, H., Misawa, N., Chamovitz, D., Pecker, I., Hirschberg, J., Sandmann, G., "Functional Complementation in *Escherichia coli* of Different Phytoene Desaturase Genes and Analysis of Accumulated Carotenes", Z. Naturforsch., 46c, 1045–1051, 1991).

(2) Preparation of lycopene-producing *Escherichia coli*

After the removal of the BstEII (1235)-SnaBI (3497) fragment from a plasmid pCAR16 having a carotenoid synthesis gene cluster except the crtZ gene of *Erwinia uredovora*, a 3.75 kb Asp718 (KpnI)-EcoRI fragment containing the crtE, crtI and crtB genes required for the production of lycopene was cut out. This fragment was then inserted into the EcoRV site of the *E. coli* vector pACYC184 to give an aimed plasmid (pACCRT-EIB). The bacterium *E. coli* containing pACCRT-EIB exhibits $Cm^r$ and produces lycopene (Cunningham Jr, F. X., Chamovitz, D., Misawa, N., Gatt, E., Hirschberg, J., "Cloning and Functional Expression in *Escherichia coli* of Cyanobacterial Gene for Lycopene Cyclase, the Enzyme that catalyzes the Biosynthesis of β-Carotenes", FEBS Lett., 328, 130–138, 1993).

(3) Preparation of β-carotene-producing *Escherichia coli*

17

After the crtX gene was inactivated by subjecting a plasmid pCAR16 having a carotenoid synthesis gene cluster except the crtZ gene of *Erwinia uredovora* to digestion with restriction enzyme BstEII, the Klenow fragment treatment and the ligation reaction, a 6.0 kb Asp718 (KpnI)-EcoRI fragment containing crtE, crtY, crtI and crtB genes required for the production of β-carotene was cut out. This fragment was then inserted into the EcoRV site of the *E. coli* vector pACYC184 to give an aimed plasmid (referred to hereinafter as pACCAR16ΔcrtX). The bacterium *E. coli* containing pACCCAR16ΔcrtX exhibits $Cm^r$ and produces β-carotene. In this connection, the restriction enzyme and enzymes used for genetic manipulation have been purchased from TAKARA SHUZO (K.K.) or Boehringer-Mannheim.

Example 3

Preparation of a Cosmid Library and Acquisition of *Escherichia coli* which Exhibits Orange in Color After the restriction enzyme Sau3AI was added in an amount of one unit to 25 μg of the chromosomal DNA of *Agrobacterium aurantiacus* sp. nov. MK1, the mixture was incubated at 37° C. for 15 minutes and heat treated at 68° C. for 10 minutes to inactivate the restriction enzyme. Under the condition, many partially digested fragments with Sau3AI were obtained at about 40 kb. The cosmid vector pJBB (resistant to ampicillin ($Ap^r$)) which had been subjected to BamHI digestion and alkaline phosphatase treatment and the right arm (shorter fragment) of pJBB which had been digested with SalI/BamHI and then recovered from the gel were mixed with a part of the above Sau3AI partial fragments, and ligated at 12° C. overnight. In this connection, pJBB has been purchased from Amersham.

Phage particles were obtained in an amount sufficient for preparing a cosmid library by the in vitro packaging with a Gigapack Gold (manufactured by Stratagene; available from Funakoshi) using the DNA above ligated.

After *Escherichia coli* DH1 (ATCC33849) and *Escherichia coli* DH1, each of which has one of the three plasmids prepared in Example 2, were infected with the phage particles, these bacteria were diluted so that 100–300 colonies were found on a plate, plated on LB containing appropriate antibiotics (1% trypton, 0.5% yeast extract, 1% NaCl), and cultured at 37° C. or room temperature for a period of overnight to several days.

As a result, in cosmid libraries having the simple *Escherichia coli* (beige) or the phytoene-producing *Escherichia coli* (beige) with pACCRT-EB as a host, no colonies with changed color were obtained notwithstanding the screening of a ten thousand or more of the colonies for respective libraries. On the other hand, in cosmid libraries having the lycopene-producing *Escherichia coli* (light red) with pACCRT-EIB or the β-carotene-producing *Escherichia coli* (yellow) with pACCAR16ΔcrtX as a host, colonies exhibiting orange have appeared in a proportion of one strain to several hundred colonies, respectively. Most of these transformed *Escherichia coli* strains which exhibits orange contained plasmids pJPB8 in which about 40 kb partially digested Sau3AI fragments were cloned. It is also understood from the fact that no colonies with changed color appeared in cosmid libraries having the simple *Escherichia coli* or the phytoene-producing *Escherichia coli* with pACCRT-EB as s host, that *Escherichia coli* having an ability of producing a carotenoid synthetic intermediate of the later steps of at least phytoene should be used as a host for the purpose of expression-cloning the xanthophyll synthesis gene cluster from the chromosomal DNA of *Agrobacterium aurantiacus* sp. nov. MK1.

Example 4

Localization of a Fragment Containing an Orange Pigment Synthesis Gene Cluster

When individual several ten colonies out of the orange colonies obtained in cosmid libraries having the lycopene-producing *Escherichia coli* (light red) with pACCRT-EIB or the β-carotene-producing *Escherichia coli* (yellow) with pACCAR16ΔcrtX as a host were selected to analyze the plasmids, 33 kb–47 kb fragments partially digested with Sau3AI were inserted in vector pJB8 in all of the colonies except one strain. The remaining one strain (lycopene-producing *Escherichia coli* as a host) contains a plasmid, in which a 3.9 kb fragment partially digested with Sau3AI was inserted in pJB8 (referred to hereinafter as plasmid pAK9). This was considered to be the one formed by the in vivo deletion of the inserted fragment after the infection to *Escherichia coli*. The same pigment (identified as astaxanthin in Example 6) as that in the orange colonies obtained from the other cosmid libraries was successfully synthesized with the lycopene-producing *Escherichia coli* having pAK9, pAK9 was used as a material in the following analyses.

Example 5

Determination of the Nucleotide Sequence in the Orange Pigment Synthesis Gene Cluster A 3.9 kb EcoRI inserted fragment prepared from pAK9 was inserted into the EcoRI site of the *Escherichia coli* vector pBluescript II SK+ to give two plasmids (pAK91 and pAK92) with the opposite directions of the fragment to the vector. The restriction enzyme map of one of the plasmids (pAK92) is illustrated in FIG. 12. When pAK92 was introduced into the lycopene-producing *Escherichia coli*, orange colonies were obtained as a result of the synthesis of astaxanthin (Example 6). However, no ability for synthesizing new pigments was afforded even if pAK91 was introduced into the lycopene-producing *Escherichia coli*. It was thus considered that the pigment synthesis gene cluster in the plasmid pAK92 has the same direction as that of the lac promoter of the vector. Next, each of a 2.7 kb PstI fragment obtained by the PstI digestion of pAK91, a 2.9 kb BamHI fragment obtained by the BamHI digestion of pAK92, and 2.3 kb and 1.6 kb SalI fragments obtained by the SalI digestion of pAK92 was cloned into the vector pBluescript II SK–. The restriction maps of plasmids referred to as pAK94, pAK96, pAK98, pAK910, pAK93, and pAK95 are illustrated in FIG. 12. The plasmids pAK94, pAK96, pAK98 and pAK910 have the pigment synthesis gene cluster in the same direction as that of the lac promoter of the vector, while the plasmids pAK93 and pAK95 have the pigment synthesis gene cluster in the opposite direction to that of the promoter.

It was found that when the plasmid pAK96 having a 2.9 kb BamHI fragment was introduced into the lycopene-producing *Escherichia coli*, the transformant also synthesized astaxanthin as in the case when the plasmid pAK92 having a 3.9 kb EcoRI fragment was introduced (Example 6), so that the DNA sequence of the 2.9 kb BamHI fragment was determined.

The DNA sequence was determined by preparing deletion mutants of the 2.9 kb BamHI fragment from the normal and opposite directions and determining the sequence using clones having various lengths of deletions. The deletion mutants were prepared from the four plasmids pAK96, pAK98, pAK93 and pAK95 according to the following procedure: Each of the plasmids, 10 μg, was decomposed with SacI and XbaI and extracted with phenol/chloroform to recover DNA by ethanol precipitation. Each of DNA was dissolved in 100 μl of ExoIII buffer (50 mM Tris-Hcl, 100 mM NaCl, 5 mM MgCl$_2$, 10 mM 2-mercaptoethanol, pH 8.0), 180 units of ExoIII nuclease was added, and the mixture was maintained at 37° C. A 10 μl portion was sampled at every 1 minute, and two samples were transferred into a tube in which 20 μl of MB buffer (40 mM sodium acetate, 100 mM NaCl, 2 mM ZnCl$_2$, 10% glycerol, pH 4.5) is contained and which is placed on ice. After completion of the sampling, five tubes thus obtained were maintained at 65° C. for 10 minutes to inactivate the enzyme, five units of mung bean nuclease were added, and the mixtures were maintained at 37° C. for 30 minutes. After the reaction, five DNA fragments different from each other in the degrees of deletion were recovered from each plasmid by agarose gel electrophoresis. The DNA fragments thus recovered was blunt ended with the Klenow fragment, subjected to the ligation reaction at 16° C. overnight, and *Escherichia coli* JM109 was transformed. A single stranded DNA was prepared from each of various clones thus obtained with a helper phase M13K07, and subjected to the sequence reaction with a fluorescent primer cycle-sequence kit available from Applied Biosystem (K.K.), and the DNA sequence was determined with an automatic sequencer.

The DNA sequence comprising 2886 base pairs (bp) thus obtained is illustrated in FIGS. 5–9 (SEQ ID NO:7). As a result of examining an open reading frame having a ribosome binding site in front of the initiation codon, three open reading frames which can encode the corresponding proteins (A–B (nucleotide positions 229–864 of SEQ ID NO:7), C–D (nucleotide positions 864–1349), E–F (nucleotide positions 1349–2506) in FIGS. 5–9) were found at the positions where the three xanthophyll synthesis genes crtW, crtZ and crtY are expected to be present. For the two open reading frames of A–B and E–F, the initiating codon is GTG, and for the remaining open reading frame C–D, it is ATG.

Example 6

Identification of the Orange Pigment

The lycopene-producing *Escherichia coli* JM101 having pAK92 or pAK96 introduced thereinto (*Escherichia coli* (pACCRT-EIB, pAK92 or pAK96); exhibiting orange) or the β-carotene-producing *Escherichia coli* JM101 having pAK94 or pAK96K (FIG. 12) introduced thereinto (*Escherichia coli* (pACCAR16ΔcrtX, pAK94 or pAK96K); exhibiting orange) was cultured in 4 liters of a 2YT culture medium (1.6% trypton, 1% yeast extract, 0.5% NaCl) containing 150 μg/ml of ampicillin (Ap, manufactured by Meiji Seika) and 30 μg/ml of chloramphenicol (Cm, manufactured by Sankyo) at 37° C. for 18 hours. Bacterial cells collected from the culture solution was extracted with 600 ml of acetone, concentrated, extracted twice with 400 ml of chloroform/methanol (9/1), and concentrated to dryness. Then, thin layer chromatography (TLC) was conducted by dissolving the residue in a small amount of chloroform/methanol 99/1) and developing on a silica gel plate for preparative TLC manufactured by Merck with chloroform/methanol (15/1). The original orange pigment was separated into three spots at the Rf values of 0.72, 0.82 and 0.91 by TLC. The pigment of the darkest spot at Rf 0.72 corresponding to 50% of the total amount of orange pigment and the pigment of secondly darker spot at Rf 0.82 were scratched off from the TLC plate, dissolved in a small amount of chloroform/methanol (9/1) or methanol, and chromatographed on a Sephadex LH-20 column (15×300 mm) with an eluent of chloroform/methanol (9/1) or methanol to give purified materials in a yield of 3 mg (Rf 0.72 ) and 2 mg (Rf 0.82), respectively.

It has been elucidated from the results of the UV-visible, $^1$H-NMR and FD-MS (m/e 596) spectra that the pigment at Rf 0.72 has the same planar structure as that of astaxanthin. When the pigment was dissolved in diethyl ether:2-propanol:ethanol (5:5:2) to measure the CD spectrum, it was proved to have stereochemical configuration of 3S, 3'S, and thus identified as astaxanthin; see FIG. 11 for the structural formula). Also, the pigment at Rf 0.82 was identified as phoenicoxanthin (see FIG. 11 for the structural formula) from the results of its UV-visible, 1H-NMR and FD-MS (m/e 580) spectra. In addition, the pigment at 0.91 was canthaxanthin (Example 7(2)).

Example 7

Identification of Metabolic Intermediates of Xanthophyll (1) Identification of 4-ketozeaxanthin The zeaxanthin producing *Escherichia coli* was prepared according to the following procedure. That is to say, the plasmid pCAR25 having total carotenoid synthesis gene cluster of *Er. uredovora* (Misawa, N., Nakagawa, M., Kobayashi, K., Yamano, S., Izawa, Y., Nakamura, K., Harashima, K., "Elucidation of the *Erwinia uredovora* Carotenoid Biosynthetic Pathway by Functional Analysis of Gene Products expressed in *Escherichia coli*", J. Bacteriol., 172, p. 6704–6712, 1990; and Japanese Patent Application No. 58786/1991 (Japanese Patent Application No. 53255/1990): "DNA Strands useful for the Synthesis of Carotenoids") was digested with restriction enzyme BstEII, and subjected to the Klenow fragment treatment and ligation reaction to inactivate the crtX gene by reading frame shift, and then a 6.5 kb Asp718 (KpnI)-EcoRI fragment containing the crtE, crtY, crtI, crtB and crtZ genes required for producing zeaxanthin was cut out. This fragment was then inserted into the EcoRV site of the *Escherichia coli* vector pACYC184 to give the aimed plasmid (referred to hereinafter as pACCAR25ΔcrtX).

The zeaxanthin-producing *Escherichia coli* JM101 having pAK910 or pAK916 (FIG. 12) introduced thereinto (*Escherichia coli* (pACCAR25ΔcrtX, pAK910 or pAK916); exhibiting orange) was cultured in 2 liters of a 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 ml of chloroform/methanol (9/1), and concentrated to dryness. Then, thin layer chromatography (TLC) was conducted by dissolving the residue in a small amount of chloroform/methanol (9/1) and developing in a silica gel plate for preparative TLC manufactured by Merck with chloroform/methanol (15/1). The original orange pigment was separated into three spots at the Rf values of 0.54 (46%), 0.72 (53%) and 0.91 (1%) by TLC. The pigment at Rf 0.54 was scratched off from the TLC plate, dissolved in a small amount of chloroform/methanol (9/1) or methanol, and chromatographed on a Sephadex LH-20 column (15×300 mm) with an eluent of chloroform/methanol (9/1) or methanol to give a purified material in a yield of 1.5 mg.

This material was identified as 4-ketozeaxanthin (see FIG. 11 for the structural formula) since its UV-visible spectrum, FD-MS spectrum (m/e 582) and mobility in silica gel TLC (developed with chloroform/methanol (15/1)) accorded perfectly with those of the standard sample of 4-ketozeaxanthin (purified from *Agrobacterium aurantiacus* sp. nov. MK1; Japanese Patent Application No. 70335/1993). In addition, the pigments of Rf0.72 and 0.91 are astaxanthin (Example 6) and canthaxanthin (Example 7 (2)), respectively.

(2) Identification of canthaxanthin

The β-carotene producing *Escherichia coli* JM101 having pAK910 or pAK916 introduced thereinto (*Escherichia coli* (pACCAR16ΔcrtX, pAK910 or pAK916); exhibiting orange) was cultured in 2 liters of a 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 ml of chloroform/methanol (9/1), and concentrated to dryness. Then, thin layer chromatography (TLC) was conducted by dissolving the residue in a small amount of chloroform/methanol (9/1) and developing on a silica gel plate for preparative TLC manufactured by Merck with chloroform/methanol (50/1). The pigment of the darkest spot corresponding to 94% of the total amount of orange pigments was scratched off from the TLC plate, dissolved in a small amount of chloroform/methanol (9/1) or chloroform/methanol (1/1), and chromatographed on a Sephadex LH-20 column (15×300 mm) with an eluent of chloroform/methanol (9/1) or chloroform/methanol (1/1) to give a purified material in a yield of 3 mg.

This material was identified as canthaxanthin (see FIG. 11 for the structural formula) since its UV-visible, $^1$H-NMR, FD-MS (m/e 564) spectra and mobility in silica gel TLC (Rf 0.53 on developing with chloroform/methanol (50/1)) accorded perfectly with those of the standard sample of canthaxanthin (manufactured by BASF). In addition, the pigment corresponding to 6% of the total orange pigments found in the initial extract was considered echinenone (see FIG. 11 for the structural formula) on the basis of its UV-visible spectrum, mobility in silica gel TLC (Rf 0.78 on developing with chloroform/methanol (50/1)), and mobility in HPLC with NOVA PACK HR 6μ C18 (3.9×300 mm; manufactured by Waters) (RT 16 minutes on developing at a flow rate of 1.0 ml/min with acetonitrile/methanol/2-propanol (90/6/4)).

(3) Identification of zeaxanthin

The β-carotene-producing *Escherichia coli* JM101 having pAK96NK introduced thereinto (*Escherichia coli* (pACCAR16ΔcrtX, pAK96NK); exhibiting yellow) was cultured in 2 liters of a 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 m l of chloroform/methanol (9/1), and concentrated to dryness. Then, thin layer chromatography (TLC) was conducted by dissolving the residue in a small amount of chloroform/methanol (9/1) and developing on a silica gel plate for preparative TLC manufactured by Merck with chloroform/methanol (9/1). The pigment of the darkest spot corresponding to 87% of the total amount of yellow pigments was scratched off from the TLC plate, dissolved in a small amount of chloroform/methanol (9/1) or methanol, and chromatographed on a Sephadex LH-20 column (15×300 mm) with an eluent of chloroform/methanol (9/1) or methanol to give a purified material in a yield of 3 mg.

It has been elucidated that this material has the same planar structure as that of zeaxanthin since its UV-visible, $^1$H-NMR, FD-MS (m/e 568) spectra and mobility in silica gel TLC (Rf 0.59 on developing with chloroform/methanol (9/1)) accorded perfectly with those of the standard sample of zeaxanthin (manufactured by BASF). When the pigment was dissolved in diethyl ether:2-propanol:ethanol (5:5:2) to measure the CD spectrum, it was proved to have a stereochemical configuration of 3R, 3'R, and thus identified as zeaxanthin (see FIG. 11 for the structural formula). Also, the pigment corresponding to 13% of the total yellow pigments found in the initial extract was considered β-cryptoxanthin (see FIG. 11 for the structural formula) on the basis of its UV-visible spectrum, mobility in silica gel TLC (Rf 0.80 on developing with chloroform/methanol (9/1)), and mobility in HPLC with NOVA PACK HR 6μ C18 (3.9×300 mm; manufactured by Waters) (RT 19 minutes on developing at a flow rate of 1.0 m/min with acetonitrile/methanol/2-propanol (90/6/4)).

(4) Identification of β-carotene

The lycopene-producing *Escherichia coli* JM101 having pAK98 introduced thereinto (*Escherichia coli* (pACCRT-EIB, pAK98); exhibiting yellow) was cultured in 2 liters of a 2YT culture medium containing 150 μg/ml of Ap and 30 μg/ml of Cm at 37° C. for 18 hours. Bacterial cells collected from the culture solution was extracted with 300 ml of acetone, concentrated, and extracted twice with 200 m l of hexane. The hexane layer was concentrated and chromatographed on a silica gel column (15×300 mm) with an eluent of hexane/ethyl acetate (50/1) to give 3 mg of a purified material.

The material was identified as β-carotene (see FIG. 11 for the structural formula), since all of the data of its UV-visible, FD-MS spectrum (m/e 536) and mobility in HPLC with NOVA PACK HR 6μ C18 (3.9×300 mm; manufactured by Waters) (RT 62 minutes on developing at a flow rate of 1.0 ml/min with acetonitrile/methanol/2-propanol (90/6/4)) accorded with those of the standard sample of β-carotene (all trans type; manufactured by Sigma).

Example 8

Identification of Xanthophyll Synthesis Gene Cluster (1) Identification of a keto group-introducing enzyme gene It is apparent from the results of Example 6 that among the 3.9 kb fragment contained in pAK9 (Example 4) or pAK92, all of the genes required for the synthesis of astaxanthin from lycopene is contained in the 2.9 kb BamHI fragment at the right side (pAK96, FIG. 12). Thus, the 1.0 kb fragment at the left side is not needed. Unique NcoI and KpnI sites are present within the 2.9 kb BamHI fragment of pAK96. It is found from the results of Example 7 (3) that the 1.4 kb fragment (pAK96NK) between the NcoI and KpnI sites has a hydroxyl group-introducing enzyme activity but has not keto group-introducing enzyme activity. Canthaxanthin can also be synthesized from β-carotene with the 2.9 kb BamHI fragment from which a fragment of the right side from unique SalI site between the NcoI and KpnI sites had been removed (pAK910) or with the 2.9 kb BamHI fragment from which a fragment of the right side from the HincII site positioned at the left side of the SalI site had been removed (pAK916), but activity for synthesizing canthazanthin from β-carotene disappeared in the 2.9 kb BamHI fragment of pAK96 from which a fragment of the right side from the NcoI site left of the HincII site had been removed. On the other hand, even if a fragment of the left side from unique BglII site which is present leftward within the 0.9 kb BamHI - HincII fragment of pAK916 was removed, similar activity to that of the aforementioned BamHI - HincII fragment (pAK916) was observed. It is thus considered that a gene encoding a keto group-introducing enzyme having an enzyme activity for synthesizing canthaxanthin from β-carotene as a substrate is present within the 0.74 kg BglII - HincII fragment of paK916, and the aforementioned NcoI site is present within this gene. As a result of determining the nucleotide sequence, an open reading frame which corresponds to the gene and has a ribosome binding site just in front of the initiation codon was successfully detected, it was then designated as the crtW gene. The nucleotide sequence of the crtW gene and the encoded amino acid sequence are illustrated in FIG. 1 (SEQ ID NOS:1–2).

The crtW gene product (CrtW) of *Agrobacterium aurantiacus* sp. nov. MK1 has an enzyme activity for converting a methylene group at the 4-position of a β-ionone ring into a keto group, and one of the specific examples is an enzyme activity for synthesizing canthazanthin from β-carotene as a substrate by way of echinenone (Example 7 (2); see FIG. 1). Furthermore, the crtW gene product also has an enzyme activity for converting a methylene group at the 4-position of a 3-hydroxy-β-ionone ring into a keto group, and one of the specific examples is an enzyme activity for synthesizing astaxanthin from zeaxanthin as a substrate by way of 4-ketozeaxanthin (Example 7 (1); see FIG. 11). In addition, polypeptides having such enzyme activities and DNA strands encoding these polypeptides have not hitherto been known, and the polypeptides and the DNA strands encoding these polypeptides have no overall homology to any polypeptides or DNA strands having been hitherto known. Also, no such informations have hitherto been described that a methylene group of not only a β-ionone ring and a 3-hydroxy-β-ionone ring but also the other compounds is directly converted into a keto group with an enzyme.

(2) Identification of a Hydroxyl Group-Introducing Enzyme Gene

Unique SalI site is present within the 2.9 kb BamHI fragment of pAK96. When the 2.9 kb BamHI fragment is cut into two fragments at the SalI site, these two fragments (pAK910 and pAK98) have no hydroxyl group-introducing activity. That is to say, the left fragment (pAK910) has only a keto group-introducing enzyme activity (Example 7 (2)), and the right fragment (pAK98) has only a lycopene-cyclizing enzyme activity (Example 7 (4)). On the other hand, when a 1.4 kb NcoI - KpnI fragment (pAK96NK) containing the aforementioned SalI site is introduced into a β-carotene-producing *Escherichia coli*, zeaxanthin is synthesized by way of β-cryptoxanthin (Example 7 (3)). It is thus considered that a gene encoding a hydroxyl group-introducing enzyme which has an enzyme activity for synthesizing zeaxanthin from β-carotene as a substrate is present within the 1.4 kb NcoI - KpnI fragment of pAK96NK, and the aforementioned SalI site is present within this gene. As a result of determining the nucleotide sequence, an open reading frame which corresponds to the gene and has a ribosome binding site just in front of the initiation codon was successfully detected, it was then referred to as the crtZ gene. The nucleotide sequence of the crtZ gene and the encoded amino acid sequence are illustrated in FIG. 2 (SEQ ID NOS:3–4).

The crtZ gene product (CrtZ) of *Agrobacterium aurantiacus* sp. nov. MK1 has an enzyme activity for adding a hydroxyl group to the 3-carbon of a β-ionone ring, and one of the specific examples is an enzyme activity for synthesizing zeaxanthin from β-carotene as a substrate by way of β-cryptoxanthin (Example 7 (3); see FIG. 11). Furthermore, the crtZ gene product also has an enzyme activity for adding a hydroxyl group to the 3-carbon of a 4-keto-β-ionone ring, and one of the specific examples is an enzyme activity for synthesizing astaxanthin from canthaxanthin as a substrate by way of phoenicoxanthin (Example 6; see FIG. 11). In addition, polypeptides having the latter enzyme activity and DNA strands encoding these polypeptides have not hitherto been known. Also, the CrtZ of Agrobacterium showed significant homology to the CrtZ of *Erwinia uredovora* (identity of 57%) at the level of amino acid sequence.

(3) Identification of a Lycopene Cyclase Gene

Astaxanthin can be synthesized from β-carotene with the 2.9 kb BamHI fragment from which a fragment of the right side from a KpnI site had been removed (pAK96K) or with the 2.9 kb BamHI fragment from which a fragment right from the PstI site which is placed further right of the KpnI site had been removed (pAK94) (Example 6), but astaxanthin cannot be synthesized from lycopene. On the other hand, when a 1.6 kb SalI fragment (pAK98), which contains a right fragment from unique SalI site present further left than the aforementioned KpnI site within the 2/9 kb BamHI fragment, was introduced into lycopene-producing *Escherichia coli*, β-carotene was synthesized (Example 7 (4)). It is thus considered that a gene encoding lycopene cyclase that has an enzyme activity for synthesizing β-carotene from lycopene as a substrate is present within the 1.6 kb SalI fragment of pAK98, and this gene is present over a range of the KpnI site and the PstI site. As a result of determining the nucleotide sequence, an open reading frame which corresponds to the gene and has a ribosome binding site just in front of the initiation codon was successfully detected, it was then referred to as the crtY gene. The nucleotide sequence of the crtY gene and the amino acid sequence to be encoded are illustrated in FIGS. 3–4 (SEQ ID NO: 3).

The crtY gene product (CrtY) of *Agrobacterium aurantiacus* sp. nov. MK1 has significant homology to the CrtY of *Erwinia uredovora* (identity of 44.3%) at the level of amino acid sequence, and the functions of both enzymes are the same.

Example 9

Southern Blotting Analysis with the Chromosomal DNA of the Other Marine Bacteria Examination was conducted whether a region exhibiting homology with the isolated crtW and crtZ is obtained from a chromosomal DNAs of the other marine microorganisms. The chromosomal DNAs of Alcaligenes sp. PC-1 and Alteromonas sp. SD-402 prepared in Example 1 were digested with restriction enzymes BamHI and PstI, and separated by agarose gel electrophoresis. All of the DNA fragments thus separated were denaturated with an alkali solution of 0.5 N NaOH and 1.5 M NaCl, and transferred on a nylon membrane filter over an overnight period. The nylon membrane filter on which DNAs had been adsorbed was dipped in a hybridization solution (6×Denhardt, 5×SSC, 100 µg/ml ssDNA), and pre-hybridization was conducted at 60° C. for 2 hours. Next, the 1.5 kb DNA fragment cut out from pAK96K with BalI, which contains crtW and crtY, was labelled with a Mega prime™ DNA labelling systems (Amersham) and [α-$^{32}$P]dCTP (~100TBq/mmol) and added to the aforementioned prehybridization solution to conduct hybridization at 60° C. for 16 hours.

After hybridization, the filter was washed with 2×SSC containing 0.1% SDS at 60° C. for 1 hour, and subjected to the detection of signals showing homology by autoradiography. As a result, strong signals were obtained at about 13 kb in the product digested with BamHI and at 2.35 kb in the product digested with PstI in the case of Alcaligenes sp. PC-1, and strong signals were obtained at about 5.6 kb in the product digested with BamHI and at 20 kb or more in the product digested with PstI in the case of Alteromonas sp. SD-4.

Example 10

Acquisition of a Xanthophyll Synthesis Gene Cluster from the Other Marine Bacterium As it was found from the results of Example 9 that the PstI digest of the chromosomal DNA of Alcaligenes sp. PC-1 has a region of about 2.35 kb hybridizing with a DNA fragment containing the crtW and crtZ genes of *Agrobacterium aurantiacus* sp. nov. MK1, the chromosomal DNA of Alcaligenes was digested with PstI, and then DNA fragments of 2–3.5 kb in size was recovered by agarose gel electrophoresis. The DNA fragments thus collected were inserted into the PstI site of a vector pBluescript II SK+, and introduced into *Escherichia coli* DH5α to prepare a partial library of Alcaligenes. When the partial library was subjected to colony hybridization with a 1.5 kb DNA fragment containing the crtW and crtZ genes of Agrobacterium as a probe, a positive colony was isolated from about 5,000 colonies. In this case, colony hybridization was conducted under the same condition as in the Southern blotting analysis shown in Example 9. When plasmid DNA was isolated from the colony thus obtained, and digested with PstI to examine the size of the integrated DNA fragments, it was found that the plasmid contained three different fragments. Thus, a 2.35 kb fragment to be hybridized was selected from the three different DNA fragments by the Southern blotting analysis described in Example 9, the 2.35 kb PstI fragment was recovered by agarose gel electrophoresis and inserted again into the PstI site of pBluescript II SK+ to prepare the plasmids pPC11 and pPC12. In pPC11 and pPC12, the aforementioned 2.35 kb PstI fragment was inserted into the PstI site of pBluescript II SK+ in an opposite direction to each other. The restriction enzyme map of pPC11 is illustrated in FIG. 19.

Example 11

Determination of Nucleotide Sequence of Xanthophyll Synthesis Gene Cluster in Alcaligenes When each of pPC11 and pPC12 was introduced into β-carotene-producing *Escherichia coli*, orange colonies were obtained due to the synthesis of astaxanthin (Example 12) in the former, but no other pigments were newly synthesized in the latter. It was thus considered that the direction of the astaxanthin synthesis gene cluster in the plasmid pPC11 was the same as that of the vector lac promoter. It was also found that pPC11 contained no lycopene cyclizing enzyme genes, since no other pigments were newly produced even if pPC11 was introduced into the lycopene-producing *Escherichia coli*.

It was found that even if a plasmid having a 0.72 kb BstEII - EcoRV fragment positioned at the right side of the PstI fragment had been removed (referred to as pPC17, FIG. 19) was introduced into the β-carotene-producing *Escherichia coli*, the transformant of *Escherichia coli* synthesized astaxanthin and the like (Example 12), same as in the case of *E. coli* into which pPC11 was introduced, so that the nucleotide sequence of the 1.63 kb PstI - BstEII fragment in pPC17 was determined.

Deletion mutants were prepared with pPC17 and pPC12 according to the following procedure. A 10 μg portion of each of pPC17 and pPC12 was digested with KpnI and HindIII or KpnI and EcoRI, extracted with phenol/chloroform, and DNA was recovered by precipitation with ethanol. Each of DNAs was dissolved in 100 μl of ExoIII buffer (50 mM Tris-HCl, 100 mM NaCl, 5 mM $MgCl_2$, 10 mM 2-mercaptoethanol, pH 8.0), 180 units of ExoIII nuclease was added, and the mixture was maintained at 37° C. A 10 μl portion was sampled at every 1 minute, and two samples were transferred into a tube in which 20 μl of an MB buffer (40 mM sodium acetate, 100 mM NaCl, 2 mM $ZnCl_2$, 10% glycerol, pH 4.5) is contained and which is placed on ice. After completion of the sampling, five tubes thus obtained were maintained at 65° C. for 10 minutes to inactivate the enzyme, five units of mung bean nuclease were added, and the mixture was maintained at 37° C. for 30 minutes. After the reaction, ten DNA fragments different from each other in the degrees of deletion were recovered for each plasmid by agarose gel electrophoresis. The DNA fragments thus recovered were blunt ended with the Klenow fragment, subjected to the ligation reaction at 16° C. overnight, and *Escherichia coli* JM109 was transformed. A single stranded DNA was prepared from each of various clones thus obtained with a helper phage M13KO7, and subjected to the sequence reaction with a fluorescent primer cycle-sequence kit available from Applied Biosystem (K.K.), and the DNA sequence was determined with an automatic sequencer.

The DNA sequence comprising 1631 base pairs (bp) thus obtained is illustrated in FIGS. 16–18 (SEQ ID NO: 12). As a result of examining an open reading frame having a ribosome binding site in front of the initiating codon, two open reading frames which can encode the corresponding proteins (A–B (nucleotide positions 99–824 of SEQ ID NO: 7), C–D (nucleotide positions 824–1309) in FIGS. 16–18 7) were found at the positions where the two xanthophyll synthesis genes crtW and crtZ were expected to be present.

Example 12

Identification of Pigments Produced by *Escherichia coli* having an *Alcaligenes xanthophyll* Synthesis Gene Cluster (1) Identification of Astaxanthin and 4-ketozeaxanthin A deletion plasmid (having only crtW) having a deletion from the right BstEII to the nucleotide position 1162 (FIG. 17) (nucleotide position 1162 of SEQ ID NO: 7) among the deletion plasmids from pPC17 prepared in Example 11 was referred to as pPC17-3 (FIG. 19).

The zeaxanthin-producing *Escherichia coli* JM101 (Example 7 (1)) having pPC17-3 introduced thereinto (*Escherichia coli* (pACCAR25ΔcrtX, pPC17-3); exhibiting orange) was cultured in 2 liters of 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 ml of chloroform/methanol (9/1), and concentrated to dryness. Then, thin layer chromatography (TLC) was conducted by dissolving the residue in a small amount of chloroform/methanol (9/1) and developing on a silica gel plate for preparative TLC manufactured by Merck with chloroform/methanol (15/1). The original orange pigment was separated into three spots at the Rf values of 0.54 (ca. 25%), 0.72 (ca. 30%) and 0.91 (ca. 25%). The pigments at the Rf values of 0.54 and 0.72 were scratched off from the TLC plate, dissolved in a small amount of chloroform/methanol (9/1) or methanol, and chromatographed on a Sephadex LH-20 column (15×300 mm) with an eluent of chloroform/methanol (9/1) or methanol to give purified materials in a yield of about 1 mg, respectively.

The materials were identified as 4-ketozeaxanthin (Rf 0.54) and astaxanthin (Rf 0.72), since all of the data of their UV-visible, FD-MS spectra and mobility in TLC (developed with chloroform/methanol (15/1)) accorded with those of the standard samples of 4-ketozeaxanthin and astaxanthin. In addition, the pigment at the Rf value of 0.91 was canthaxanthin (Example 12 (2)).

It was also confirmed by the similar analytical procedures that the β-carotene-producing *Escherichia coli* JM101 having pPC11 or pPC17 introduced thereinto (*Escherichia coli* (pACCAR16ΔcrtX, pPC11 or pPC17) (exhibiting orange) produces astaxanthin, 4-ketozeaxanthin and canthaxanthin. Furthermore, it was also confirmed with the authentic sample of phoenicoxanthin obtained in Example 6 that these *E. coli* transformants produce a trace amount of phoenicoxanthin.

(2) Identification of Canthaxanthin

The β-carotene-producing *Escherichia coli* JM101 having pPC17-3 introduced thereinto (*Escherichia coli* (pACCAR16ΔcrtX, pPC17-3); exhibiting orange) was cultured in 2 liters of 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 ml of chloroform/methanol (9/1), and concentrated to dryness. Then, thin layer chromatography (TLC) was conducted by dissolving the residue in a small amount of chloroform/methanol (9/1) and developing on a silica gel plate for preparative TLC manufactured by Merck with chloroform/methanol (50/1). The darkest pigment corresponding to 40% of the total amount of orange pigments was scratched off from the TLC plate, dissolved in a small amount of chloroform/methanol (9/1) or chloroform/methanol (1/1), and chromatographed on a Sephadex LH-20 column (15×300 mm) with an eluent of chloroform/methanol (9/1) or chloroform/methanol (1/1) to give a purified material in a yield of 2 mg.

The material was identified as canthaxanthin, since all of the data of its UV-visible, FD-MS (m/e 564) spectra and mobility in TLC (developed with chloroform/methanol (50/1)) accorded with those of the standard sample of canthaxanthin (manufactured by BASF). In addition, the pigment of which amount corresponds to 50% of the total amount of the orange pigments observed in the initial extract was considered to be echinenone from its UV-visible spectrum, mobility in silica gel TLC (developed with chloroform/methanol (50/1)), and mobility in HPLC with NOVA PACK HR 6μ C18 (3.9×300 mm; manufactured by Waters) (developed with acetonitrile/methanol/2-propanol (90/6/4)) (Example 7 (2)). In addition, the balance of the extracted pigments, 10%, was unreacted β-carotene.

(3) Identification of Zeaxanthin

A plasmid having a 1.15 kb SalI fragment within pPC11 inserted in the same direction as the plasmid pPC11 into the SalI site of pBluescript II SK+ was prepared (referred to as pPC13, see FIG. 19).

The β-carotene-producing *Escherichia coli* JM101 having pPC13 introduced thereinto (*Escherichia coli* (pACCAR16ΔcrtX, pPC13); exhibiting yellow) was cultured in 2 liters of 2YT culture medium containing 150 μg/ml of Ap and 30 μg/ml of Cm at 37° C. for 18 hours. Bacterial cells collected from the culture solution was extracted with 300 ml of acetone, concentrated, extracted twice with 200 ml of chloroform/methanol (9/1), and concentrated to dryness. Then, thin layer chromatography (TLC) was conducted by dissolving the residue in a small amount of chloroform/methanol (9/1) and developing on a silica gel plate for preparative TLC manufactured by Merck with chloroform/methanol (9/1). The darkest pigment corresponding to 90% of the total amount of orange pigments was scratched off from the TLC plate, dissolved in a small amount of chloroform/methanol (9/1) or methanol, and chromatographed on a Sephadex LH-20 column (15×300 mm) with an eluent of chloroform/methanol (9/1) or methanol to give a purified material in a yield of 3 mg.

The material was identified as zeaxanthin, since all of the data of its UV-visible, FD-MS (m/e 568) spectra and mobility in TLC (developed with chloroform/methanol (9/1)) accorded with those of the standard sample of zeaxanthin (Example 7 (3)). In addition, the pigment of which amount corresponds to 10% of the total amount of the orange pigments observed in the initial extract was considered to be β-cryptoxanthin from its UV-visible spectrum, mobility in silica gel TLC (developed with chloroform/methanol (9/1), and mobility in HPLC with NOVA PACK HR 6μ C18 (3.9×300 mm; manufactured by Waters) (developed with acetonitrile/methanol/2-propanol (90/6/4) (Example 7 (3)).

Example 13

Identification of the *Alcaligenes xanthophyll* Synthesis Gene Cluster (1) Identification of a Keto Group-Introducing Enzyme Gene It is apparent from the results of Examples 11 and 12 (1) that all of the genes required for the synthesis of astaxanthin from β-carotene among the 2.35 kb PstI fragment contained in pPC11 is contained in the 1.63 kb PstI - BstEII fragment (pPC17, FIG. 19) in the left side. Thus, the 0.72 kb BstEII - PstI fragment in the right side is not needed. Unique SmaI and SalI sites are present within the 1.63 kb PstI - BstEII fragment of pPC17 (FIG. 19). It is confirmed by the pigment analysis with a β-carotene-producing *Escherichia coli* having the deletion plasmids introduced thereinto that the keto group-introducing enzyme activity was lost when the 0.65 kb and 0.69 kb fragments at the left side from SmaI and SalI sites were removed. It was also confirmed by the pigment analysis with a β-carotene-producing *Escherichia coli* having the plasmid introduced thereinto that the plasmid having a 0.69 kb PstI - SalI fragment positioned at the left side of the 1.63 kb PstI - BstEII fragment inserted into the PstI - SalI site of pBluescript SK+ has no keto group-introducing enzyme activity. On the other hand, the deletion plasmid pPC17-3 (FIG. 19) in which deletion from the BstEII end at the right end to the nucleotide No. 1162 (nucleotide position 1162 in SEQ ID NO: 12) occurred has a keto group-introducing enzyme activity (Example 12 (1), (2)), so that it is considered a gene encoding a keto group-introducing enzyme having an enzyme activity for synthesizing canthaxanthin or astaxanthin with a substrate of β-carotene or zeaxanthin is present in the 1162 bp fragment in pPC17-3, and the aforementioned SmaI and SalI sites are present within this gene. As a result of determining the nucleotide sequence, an open reading frame which corresponds to the gene and has a ribosome binding site just in front of the initiation codon was successfully detected, so that it was referred to as the crtW gene. The nucleotide sequence of the crtW gene and the encoded amino acid sequence are illustrated in FIGS. 13–14 (SEQ ID NOS: 8–9).

The crtW gene product (CrtW) of Alcaligenes sp. PC-1 has an enzyme activity for converting a methylene group at the 4-position of a β-ionone ring into a keto group, and one of the specific examples in an enzyme activity for synthesizing canthaxanthin from β-carotene as a substrate by way of echinenone (Example 12 (2); see FIG. 11). Furthermore, the crtW gene product also has an enzyme activity for converting a methylene group at the 4-position of a 3-hydroxy-β-ionone ring into a keto group, and one of the specific examples is an enzyme activity for synthesizing astaxanthin from zeaxanthin as a substrate by way of 4-ketozeaxanthin (Example 12 (1); see FIG. 11). In addition, polypeptides having such enzyme activities and DNA strands encoding these polypeptides have not hitherto been known, and the polypeptides and the DNA strands encoding these polypeptides have no total homology to any polypeptides or DNA strands having been hitherto known. Also, the crtW gene products (crtW) of *Agrobacterium aurantiacus* sp. nov. MK1 and Alcaligenes sp. PC-1 share high homology (identify of 83%) at the level of amino acid sequence, and the functions of both enzymes are the same. The amino acid sequence in the region of 17% having no identity among these amino acid sequences is considered not so significant to the functions of the enzyme. It is thus considered particularly in this region that a little amount of substitution by the other amino acids, deletion, or addition of the other amino acids will not affect the enzyme activity.

It can be said the keto group-introducing enzyme gene crtW of marine bacteria encodes the β-ionone or 3-hydroxy-β-ionone ring ketolase which converts directly the methylene group at the 4-position into a keto group irrelative to whether a hydroxyl group is added to the 3-position or not. In addition, no such informations have hitherto been described that a methylene group of not only a β-ionone ring and a 3-hydroxy-β-ionone ring but also the other compounds is directly converted into a keto group with one enzyme.

(2) Identification of a Hydroxy Group-Introducing Enzyme Gene

All of the genes required for the synthesis of astaxanthin from β-carotene is contained in the 1.63 kb PstI - BstEII fragment (FIG. 19) of pPC17. One SalI site is present within the 1.63 kb PstI - BstEII fragment of pPC17. It is apparent from the results of Example (12(3)) that a hydroxyl group-introducing enzyme activity is present in a fragment at the right side from the SalI site. It is thus understood that the hydroxyl group-introducing enzyme activity is present in the 0.94 kb SalI - BstEII fragment which is the right fragment in the 1.63 kb PstI - BstEII fragment. As a result of determining the nucleotide sequence, an open reading frame which corresponds to the gene and has a ribosome binding site just in front of the initiation codon was successfully detected, it was referred to as the crtZ gene. The nucleotide sequence of the crtZ gene and the encoded amino acid sequence are illustrated in FIG. 15 (SEQ ID NOS: 10–11).

The crtZ gene product (CrtZ) of Alcaligenes sp. PC-1 has an enzyme activity for adding a hydroxyl group to the 3-carbon of a β-ionone ring, and one of the specific examples is an enzyme activity for synthesizing zeaxanthin from β-carotene as a substrate by way of β-cryptoxanthin (Example 12 (3); see FIG. 11). Furthermore, the crtZ gene product also has an enzyme activity for adding a hydroxyl group to the 3-carbon of a 4-keto-β-ionone ring, and one of the specific examples is an enzyme activity for synthesizing astaxanthin from canthaxanthin as a substrate by way of phoenicoxanthin (Example 12 (1); see FIG. 11). In addition, polypeptides having the latter enzyme activity and DNA strands encoding these polypeptides have not hitherto been known. Also, the CrtZ of Alcaligenes sp. PC-1 showed significant homology to the CrtZ of *Erwinia uredovora* (identity of 58%) at the level of amino acid sequence. In addition, the crtZ gene products (CrtZ) of *Agrobacterium aurantiacus* sp. nov. MK1 and Alcaligenes sp. PC-1 have high homology (identity of 90%) at the level of amino acid sequence, and the functions of both enzymes are the same. The amino acid sequence in the region of 10% having no identity among these amino acid sequences is considered not so significant to the functions of the enzyme. It is thus considered particularly in this region that a little amount of substitution by the other amino acids, deletion, or addition of the other amino acids will not affect the enzyme activity.

(3) Consideration on Minor Biosynthetic Pathways of Xanthophylls

It has been elucidated by our studies with carotenoid synthesis genes of the epiphytic bacterium Erwinia or the photosynthetic bacterium Rhodobacter that carotenoid biosynthesis enzymes generally act by recognizing the half of a carotenoid molecule as a substrate. By way of example, the lycopene cyclase gene of Erwinia, crtY, recognizes the halves of the lycopene molecule to cyclize it. When the phytoene desaturase gene crtI of Rhodobacter was used for the synthesis of neurosporene in place of lycopene in *Escherichia coli* and crtY of Erwinia was allowed to work on it, the crtY gene product recognizes the half molecular structure common to lycopene to produce a half cyclized β-zeacarotene (Linden, H., Misawa, N., Chamovits, D., Pecher, I., Hirschberg, J., Sandmann, G., "Functional Complementation in *Escherichia coli* of Different Phytoene Desaturase Genes and Analysis of Accumulated Carotenes", Z. Naturforsch., 46c, p. 1045–1051, 1991). Also, in the present invention, when CrtW is allowed to work on β-carotene or zeaxanthin, echinenone or 4-ketozeaxanthin in which one keto group has been introduced is first synthesized, and when CrtZ is allowed to work on β-carotene or canthaxanthin, β-cryptoxanthin or phoenicoxanthin in which one hydroxyl group has been introduced is first synthesized. It can be considered because these enzymes recognize the half molecule of the substrate. Thus, while *Escherichia coli* having the crtE, crtB, crtI and crtY genes of Erwinia and the crtZ gene of a marine bacterium produces zeaxanthin as described above, β-cryptoxanthin which is β-carotene having one hydroxyl group introduced thereinto can be detected as an intermediate metabolite. It can be thus considered that if CrtW is present, 3'-hydroxyechinenone or 3-hydroxyechinenone can be synthesized from β-cryptoxanthin as a substrate, and that phoenicoxanthin can be further synthesized by the action of CrtW on these intermediates. The present inventors have not identified these ketocarotenoids in the culture solutions, and the reason is considered to be that only a trace amount of these compounds is present under the conditions carried out in the present experiments. In fact, it was described that 3-hydroxyechinenone or 3'-hydroxyechinenone was detected as a minor intermediate metabilite of astaxanthin in a marine bacterium *Agrobacterium aurantiacus* sp. nov. MK1 as a gene source (Akihiro Yokoyama ed., "For the biosynthesis of astaxanthin in marine bacteria", Nippon Suisan Gakkai, Spring Symposium, 1994, Abstract, p. 252, 1994). It can be considered from the above descriptions that minor metabolic pathways shown in FIG. 20 are also present in addition to the main metabolic pathways of astaxanthin shown in FIG. 11.

INDUSTRIAL APPLICABILITY

According to the present invention, the gene clusters required for the biosynthesis of keto group-containing xanthophylls such as astaxanthin, phoenicoxanthin, 4-ketozeaxanthin, canthaxanthin and echinenone have successfully been obtained from marine bacteria, and their structures, nucleotide sequences, and functions have been elucidated. The DNA strands according to the present invention are useful as genes capable of affording the ability of biosynthesis of keto group-containing xanthophylls such as astaxanthin to microorganisms such as *Escherichia coli* and the like.

We claim:

1. An isolated first or second DNA strand,
wherein the first DNA strand encodes a polypeptide capable of converting the methylene group at the 4-position of a β-ionone ring into a keto group,
wherein the second DNA strand is the complement of the first DNA strand, and
wherein the polypeptide is found in Agrobacterium or Alcaligenes.

2. The first or second DNA strand of claim 1, wherein the polypeptide comprises the amino acid sequence encoded by the nucleotide sequence of SEQ ID NO:1 or SEQ ID NO:8.

3. The first or second DNA strand of claim 1, wherein the polypeptide is capable of converting β-carotene into canthaxanthin by way of echinenone.

4. The first or second DNA strand of claim 1, wherein the polypeptide is capable of converting zeaxanthin into astaxanthin by way of 4-ketozeaxanthin.

5. The first or second DNA strand of claim 1, wherein the β-ionone ring is a 3-hydroxy-β-ionone ring.

6. An isolated first or second DNA strand,
wherein the first DNA strand encodes a polypeptide capable of converting the methylene group at the 4-position of a β-ionone ring into a keto group,
wherein the second DNA strand is the complement of the first DNA strand,
wherein the first DNA strand hybridizes to the complement of a third DNA strand comprising the nucleotide sequence of SEQ ID NO:1 or SEQ ID NO:8 to form a hybrid if the first DNA strand and the complement of the third DNA strand are held together in a solution comprising 5×SSC and 6×Denhardt for 16 hours at 60° C., and
wherein the first DNA strand and the complement of the third DNA strand remain hybridized to each other after contacting the hybrid with a solution comprising 2×SSC and 0.1% SDS for 1 hour at 60° C.

7. The first or second DNA strand of claim 6, wherein the polypeptide comprises the amino acid sequence encoded by the nucleotide sequence of SEQ ID NO:1 or SEQ ID NO:8.

8. The first or second DNA strand of claim 6, wherein the polypeptide is capable of converting β-carotene into canthaxanthin by way of echinenone.

9. The first or second DNA strand of claim 6, wherein the polypeptide is capable of converting zeaxanthin into astaxanthin by way of 4-ketozeaxanthin.

10. The first or second DNA strand of claim 6, wherein the β-ionone ring is a 3-hydroxy-β-ionone ring.

11. An isolated first or second DNA strand,
wherein the first DNA strand encodes a polypeptide capable of adding a hydroxyl group to the 3-carbon of a 4-keto-β-ionone ring.
wherein the second DNA strand is the complement of the first DNA strand, and
wherein the polypeptide is found in Agrobacterium or Alcaligenes.

12. The first or second DNA strand of claim 11, wherein the polypeptide comprises the amino acid sequence encoded by the nucleotide sequence of SEQ ID NO:3 or SEQ ID NO:10.

13. The first or second DNA strand of claim 11, wherein the polypeptide is capable of converting canthaxanthin into astaxanthin by way of phoenicoxanthin.

14. An isolated first or second DNA strand,
wherein the first DNA strand encodes a polypeptide capable of adding a hydroxyl group to the 3-carbon of a 4-keto-β-ionone ring.
wherein the second DNA strand is the complement of the first DNA strand,
wherein the first DNA strand hybridizes to the complement of a third DNA strand comprising the nucleotide sequence of SEQ ID NO:3 or SEQ ID NO:10 to form a hybrid if the first DNA strand and the complement of the third DNA strand are held together in a solution comprising 5×SSC and 6×Denhardt for 16 hours at 60° C., and
wherein the first DNA strand and the complement of the third DNA strand remain hybridized to each other after contacting the hybrid with a solution comprising 2×SSC and 0.1% SDS for 1 hour at 60° C.

15. The first or second DNA strand of claim 14, wherein the polypeptide comprises the amino acid sequence encoded by the nucleotide sequence of SEQ ID NO:3 or SEQ ID NO:10.

16. The first or second DNA strand of claim 14, wherein the polypeptide is capable of converting canthaxanthin into astaxanthin by way of phoenicoxanthin.

17. An isolated DNA strand comprising the nucleotide sequence of SEQ ID NO:1, SEQ ID NO:3, SEQ ID NO:8, or SEQ ID NO:10.

18. A vector comprising the isolated DNA strand of claim 17.

19. A host cell comprising the recombinant vector of claim 18.

* * * * *